(12) United States Patent
Wagner et al.

(10) Patent No.: US 6,355,415 B1
(45) Date of Patent: Mar. 12, 2002

(54) COMPOSITIONS AND METHODS FOR THE USE OF RIBOZYMES TO DETERMINE GENE FUNCTION

(75) Inventors: Thomas E. Wagner, Greenville, SC (US); Yuefeng Xie, Gaitersburg, MD (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 08/939,366

(22) Filed: Sep. 29, 1997

(51) Int. Cl.$^7$ ............................................. C12Q 1/68
(52) U.S. Cl. .................................................. 435/6
(58) Field of Search ............................ 435/6; 536/23.2

(56) References Cited

U.S. PATENT DOCUMENTS

| | | | |
|---|---|---|---|
| 4,683,195 A | 7/1987 | Mullis et al. | 475/6 |
| 4,683,202 A | 7/1987 | Mullis | 435/91 |
| 4,940,838 A | 7/1990 | Schilperoort et al. | 800/205 |
| 4,965,188 A | 10/1990 | Mullis et al. | 435/6 |
| 5,144,019 A | 9/1992 | Rossi et al. | 536/27 |
| 5,225,347 A | 7/1993 | Goldberg et al. | 435/320.1 |
| 5,246,921 A | 9/1993 | Reddy et al. | 514/44 |
| 5,436,330 A * | 7/1995 | Taira et al. | 536/23.2 |
| 5,496,698 A * | 3/1996 | Draper et al. | 435/6 |
| 5,500,357 A | 3/1996 | Taira et al. | 435/91.31 |
| 5,527,895 A | 6/1996 | Hampel et al. | 536/23.2 |
| 5,584,807 A | 12/1996 | McCabe | 604/71 |
| 5,591,601 A | 1/1997 | Wagner et al. | 435/69.1 |

OTHER PUBLICATIONS

Celera compiles DNA sequence covering 90% of the human genome. http://www.pecorporation.com/press/prccorp011000.html, Jan. 2000.*

Genomics 101. wysiwyg://21//http://www.celera.com/Genomics101/TheBasicsofGenomics.shtm, Feb. 2000.*

Watson et al. Recombinant DNA, 2nd edition, pp. 266–267, 1992.*

Levine et al. Human DNA sequences homologous to a protein coding region conserved between homoeotic genes of Drosophila. Cell 38(3):667–674, 1984.*

Xie et al. A ribozyme–mediated, gene "knockdown" strategy for the identification of gene function in zebrafish. Proc. Natl. Acad. Sci. USA 94:13,777–13,781, Dec. 1997.*

Zhao et al. Generating loss–of–function phenotypes of the fushi tarazu gene with a targeted ribozyme in Drosophila. Nature 365:448–451, Sep. 1993.*

Cox et al. (1994) "Assessing Mapping Progress in the Human Genome Project," Science 265:3031–2032.

Guyer et al. (1995) "How is the Human Genome Project doing, and what have we learned so far?" Proc. Natl. Acad. Sci.92:10841–10848.

Capecchi et al. (1989) "Altering the Genome by Homologous Recombination," Science 244:1288–1292.

Hasty et al. (1991) "Introduction of a subtle mutation into the Hox–2.6 locus in embryonic stem cells," Nature 350:243–246.

Shastry (1994) "More to learn from gene knockouts," Mol. Cell. Biochem. 136:171–182.

Galli–Taliadoros et al. (1995) "Gene knock–out technology: a methodological overview for the interested novice," J. Immunol. Methods 181:1–15.

Maniatis et al. (1987) "Regulation of Inducible and Tissue–Specific Gene Expression," Science 236:1237–1244.

Sambrook et al. (1989) *Molecular Cloning: A Laboratory Manual,* 2nd ed., Cold Spring Harbor Laboratory Press, NY, pp. 16.7–16.8.

Sambrook et al. (1989) *Molecular Cloning: A Laboratory Manual,* 2nd ed., Cold Spring Harbor Laboratory Press, NY, pp. 9.31–9.58.

Sullivan (1994) "Development of Ribozymes For Gene Therapy," J. Invest. Derma. 103:85S–89S.

Xing et al. (1992) "Ribozymes Which Cleave Arenavirus RNAs: Identification of Susceptible Target Sites and Inhibition by Target Site Secondary Structure," J. Virol. 66:1361–1369.

Puttaraju et al. (1993) "A circular trans–acting hepatitis delta virus ribozyme," Nucl. Acids Res. 21: 4253–4258.

Steinecke et al. (1992) "Expression of a chimeric ribozyme gene results in endonucleolytic cleavage of target mRNA and a concomitant reduction of gene expression in vivo," EMBO J. 11:1525–1530.

Lieber and Strauss (1995) "Selection of Efficient Cleavage Sites in Target RNAs by Using a Ribozyme Expression Library," Mol. Cell. Biol. 15(1): 540–551.

Kruger et al. (1982) "Self–Splicing RNA: Autoexcision and Autocyclization of the Ribosomal RNA Intervening Sequence of Tetrahymena," Cell 31: 147–157.

Zaug et al. (1986) "The Tetrahymena ribozyme acts like an RNA restriction endonuclease," Nature 324:429–433.

Guerrier–Takada et al. (1983) "The RNA Moiety of Ribonuclease P is the Catalytic Subunit of the Enzyme," Cell 35: 849–857.

Feldstein et al. (1989) "Two sequences participating in the autolytic processing of satellite tobacco ringspot virus complementary RNA," Gene 82:53–61.

(List continued on next page.)

*Primary Examiner*—Karen Cochrane Carlson
(74) *Attorney, Agent, or Firm*—Medlen & Carroll, LLP

(57) ABSTRACT

The present invention provides nucleic acid sequences and methods to define gene function. In particular, the present invention relates to reducing the levels of RNA encoded by a DNA sequence of interest using ribozymes. The present invention further relates to ribozyme sequences, recombinant expression vectors encoding ribozymes as well as host cells and transgenic organisms comprising such expression vectors, and the use of these compositions for the determination of gene function.

26 Claims, 15 Drawing Sheets

OTHER PUBLICATIONS

Wu et al. (1989) "Reversible Cleavage and Ligation of Hepatitis Delta Virus RNA," Science 243:652–655.

Hofacker et al. (1994) "Fast Folding and Comparison of RNA Secondary Structures," Monatshsefte F. Chemie 125:167–188.

McCaskill (1990) "The Equilibrium Partition Function and Base Pair Binding Probabilities for RNA Secondary Structure," Biopolymers 29:1105–1119.

Sioud and Drlica (1991) "Prevention of human immunodeficiency virus type 1 integrase expression in *Escherichia coli* by a ribozyme," Proc. Natl. Acad. Sci. 88:7303–7307.

"Molecular and Cellular Biology," Stephen L. Wolfe (Ed.), Wadsworth Publishing Company (1993) p. 575.

Klee et al. (1987) "Agrobacterium–Mediated Plant Transformation and Its Further Applications to Plant Biology," Ann. Rev. Plant Phys. 38:467–486.

Nan et al. (1995) "II.2 Genetic Transformation in Dendrobium (Orchid)," in *Biotechnology in Agriculture and Forestry*, Ed. Y.P.S. Bajaj, Springer–Verlag Berlin Heidelberg, vol. 34:145–155.

Griesbach (1992) "Incorporation of the Gus Gene Into Orchids via Embryo Electrophoresis," HortScience 27:620 (Abstr. 347).

Fraley et al. (1982) "Liposome–mediated delivery of tobacco mosaic virus RNA into tobacco protoplasts: A sensitive assay for monitoring liposome–protoplast interactions," Proc. Natl. Acad. Sci. 79:1859–1863.

Krens et al. (1982) In vitro transformation of plant protoplasts with Ti–plasmid DNA,Nature 296:72–74.

Schulte–Merker et al. (1992) "The protein product of the zebrafish homologue of the mouse T gene is expressed in nuclei of the germ ring and the notochord of the early embryo," Development 116:1021–1032.

Herrmann et al. (1990) "Cloning of the T gene required in mesoderm formation in the mouse," Nature 343:617–622.

Smith et al.(1990) "Expression of a Xenopus Homolog of Brachyury (T) Is an Immediate–Early Response to Mesoderm Induction," Cell 67:79–87.

Blum et al. (1992) "Gastrulation in the Mouse: The Role of the Homeobox Gene goosecoid," Cell 69:1097–1106.

Izpisua–Belmonte et al. (1993) "The Homeobox Gene goosecoid and the Origin of Organizer Cells in the Early Chick Blastoderm," Cell 76:645–659.

Blumberg et al. (1991) "Organizer–Specific Homeobox Genes in *Xenopus laevis* Embryos," Science 253:194–196.

Stachel et al. (1993) "Lithium perturbation and goosecoid expression identify a dorsal specification pathway in the pregastrula zebrafish," Development 117:1261–1274.

Inoue et al. (1989) "Stage–dependent expression of the chicken δ–crystallin gene in transgenic fish embryos," Cell Differen. & Develop. 27:57–68.

Xie et al. (1993) "Gene transfer via electroporation in fish," Aquaculture 111: 207–213.

Müller et al. (1993) "Efficient transient expression system based on square pulse electroporation and in vivo luciferase assay of fertilized fish eggs," FEBS 324:27–32.

Patil et al. (1996) "Nuclear Internalization of Foreign DNA by Zebrafish Spermatozoa and Its Enhancement by Electroporation," J. Exp. Zool. 274:121–129.

Lin et al. (1994) "Integration and Germ–Line Transmission of a Pseudotyped Retroviral Vector in Zebrafish," Science 265:666–669.

Gaiano et al. (1996) "Highly efficient germ–line transmission of proviral insertions in zebrafish," Proc. Natl. Acad. Sci. 93:7777–7782.

Schulte–Merker et al. (1994) "no tail (ntl) is the zebrafish homologue of the mouse T (Brachyury) gene," Development 120:1009–1015.

Halpern et al. (1993) "Induction of Muscle Pioneers and Floor Plate Is Distinguished by the Zebrafish no tail Mutation," Cell 75:99–111.

Production of a Subtracted cDNA Library in *Current Protocols in Molecular Biology* (1992) Section 5.8.9.

Haag et al. (1994) "Effects of Primer Choice and Source of Taq DNA Polymerase on the Banding Patterns of Differential Display RT–PCR," Biotechniques 17:226–228.

Ikonomov et al. (1996) "Differential Display Protocol With Selected Primers That Preferentially Isolates mRNAs of Moderate to Low Abundance in a Microscopic System," Biotechniques 20:1030–1042.

Moss et al. (1990) "New mammalian expression vectors," Nature 348:91–92.

Chen et al. (1994) "A self–initiating eukaryotic transient gene expression system based on cotransfection of bacteriophage T7 RNA polymerase and DNA vectors containing a T7 autogene," Nucleic Acids Res. 22:2114–2120.

Chomcynski and Sacchi (1987) "Single–Step Method of RNA Isolation by Acid Guanidinium Thiocyantate–Phenol–Chloroform Extraction," Anal. Biochem. 162:156–159.

Uyttendaele et al. (1996) "Notch4/int–3, a mammary proto–oncogene, is an endothelial cell–specific mammalian Notch gene," Development 122:2251–2259.

Barinaga (1993) "Ribozymes: Killing the messenger," Science 262:1512–1514. Barinaga reviews the discovery of ribozymes, their structures, activities, targeting and delivery, and their potential uses in gene therapy as anti–infectives.

Burke (1997) "Clearing the way for ribozymes," Nature Bio. 15:414–415.

Chen et al. (1997) "Efficient hammerhead ribozyme and antisense RNA targeting in a slow ribosome *Escherichia coli* mutant," Nature Bio. 15:432–435.

Collodi et al. (1992) "Culture of cells from zebrafish (*Brachydanio rerio*) embryo and adult tissues," Cell Biol. Toxicol. 8:43–61.

Cotten and Birnstiel S(1989) "Ribozyme mediated destruction of RNA in vivo,"0 EMBO J. 8:3861–3866.

Crisell et al. (1993) "Inhibition of HIV–1, replication by ribozymes that show poor activity in vitro," Nucl. Acids Res. 21:5251–5255.

Dolganov et al. (1996) "Human Rad50 Is Physically Associated with Human Mre11: Identification of a Conserved Multiprotein Complex Implicated in Recombinatorial DNA Repair," Mol. Cell. Biol. 16:4832–4841.

Ellis and Rogers (1993) "Design and specificity of hammerhead ribozymes against calretinin mRNA," Nucl. Acids Res. 21:5171–5178.

Ge et al. (1995) "Gene therapeutic approaches to primary and metastatic brain tumors: II. Ribozyme–mediated suppression of CD44 expression," J. Neuro–Oncol. 26:251–257.

Haseloff and Gerlach (1988) "Simple RNA enzymes with new and highly specific endoribonuclease activities," Nature 334:585–591.

Huang and Carmichael (1996) "Role of polyadenylation in nucleocytoplasmic transport of mRNA," Mol. Cell. Biol. 16:1534–1542.

Jeffries and Symons (1989) "A catalytic 13–mer ribozyme," Nucl. Acids Res. 17:1371–1377.

Larsson et al. (1994) "Reduced β–macroglobulin mRNA levels in transgenic mice expressing a designed hammerhead ribozyme," Nucl. Acids Res. 22:2242–2248.

Lieber and Kay (1996) "Adenovirus–mediated expression of ribozymes in mice," J. Virol. 70:3153–3158.

Mazzolini et al. (1992) "Assaying synthetic ribozymes in plants: High–level expression of a functional hammerhead structure fails to inhibit target gene activity in transiently transformed protoplasts," Plant Mol. Biol. 20:715–731.

Mei et al. (1989) "A computational approach to the mechanism of self–cleavage of hammerhead RNA," Proc. Natl. Acad. Sci. 86:9727–9731.

Ohkawa et al. (1993) "Importance of independence in ribozyme reactions. Kinetic behavior of trimmed and of simply connected multiple ribozymes with potential activity against human immunodeficiency virus," Proc. Natl. Acad. Sci. 90:11302–11306.

Sarver et al. (1990) "Ribozymes as potential anti–HIV–1 therapeutic agents," Science 247:1222–1225.

Stuart et al. (1988) "Replication, integration and stable germ–line transmission of foreign sequences injected into early zebrafish embryos," Develop. 103:403–412.

Stuart et al. (1990) "Stable lines of transgenic zebrafish exhibit reproducible patterns of transgene expression," Develop. 109:577–584.

Sullenger and Cech (1993) "Tethering ribozymes to a retroviral packaging signal for destruction of viral RNA," Science 262:1566–1659.

Ventura et al. (1994) "Ribozyme targeting of HIV–1 LTR," Biochem. Biophys. Res. Commun. 203:889–898.

Xie (1996) "The Establishment of a Model System for Gene Inactivation in the Early Zebrafish Embryos by Transient Expression of a Ribozyme Directed Against Zebrafish ntl Gene," Research Proposal.

Yu et al. (1993) "A hairpin ribozyme inhibits expression of diverse strains of human immunodeficiency virus type 1," Proc. Natl. Acad. Sci. 90:6340–6344.

Yuyama et al. (1992) "Construction of a tRNA–embedded–ribozyme trimming plasmid," Biochem. Biophys. Res. Commun. 186:1271–1279.

* cited by examiner

```
GAATTCCCGC TGTCAAAGCA ACAGTATCCA ACGGGAGTTA GTAGGATCGT CGGACTTATC       60

TCAAGCTTTA TTTGATCGGA AAT ATG TCT GCC TCA AGT CCC GAC CAG CGC          110
                         Met Ser Ala Ser Ser Pro Asp Gln Arg
                          1                   5

CTG GAT CAT CTC CTT AGC GCC GTG GAG AGC GAA TTT CAG AAG GGC AGC        158
Leu Asp His Leu Leu Ser Ala Val Glu Ser Glu Phe Gln Lys Gly Ser
 10              15                  20                  25

GAG AAA GGG GAC GCG TCC GAG CGG GAT ATT AAA CTT TCG CTT GAA GAC        206
Glu Lys Gly Asp Ala Ser Glu Arg Asp Ile Lys Leu Ser Leu Glu Asp
                 30                  35                  40

GCG GAG TTG TGG ACC AAA TTT AAA GAG CTC ACC AAT GAA ATG ATT GTC        254
Ala Glu Leu Trp Thr Lys Phe Lys Glu Leu Thr Asn Glu Met Ile Val
             45                  50                  55

ACC AAG ACT GGG AGA CGA ATG TTT CCC GTG CTC AGA GCC AGT GTC ACC        302
Thr Lys Thr Gly Arg Arg Met Phe Pro Val Leu Arg Ala Ser Val Thr
                 60                  65                  70

GGT CTC GAC CCT AAT GCA ATG TAC TCG GTC CTG CTG GAT TTT GTG GCG        350
Gly Leu Asp Pro Asn Ala Met Tyr Ser Val Leu Leu Asp Phe Val Ala
 75                  80                  85

GCC GAT AAT AAT CGG TGG AAA TAC GTG AAC GGT GAA TGG GTG CCC GGT        398
Ala Asp Asn Asn Arg Trp Lys Tyr Val Asn Gly Glu Trp Val Pro Gly
 90                  95                  100                 105

GGG AAA CCC GAA CCC CAA AGC CCG AGC TGC GTC TAC ATC CAC CCG GAC        446
Gly Lys Pro Glu Pro Gln Ser Pro Ser Cys Val Tyr Ile His Pro Asp
                 110                 115                 120

TCA CCC AAC TTC GGC GCG CAC TGG ATG AAA GCA CCC GTA TCT TTC AGC        494
Ser Pro Asn Phe Gly Ala His Trp Met Lys Ala Pro Val Ser Phe Ser
                 125                 130                 135

AAA GTC AAA CTC TCC AAT AAA CTC AAC GGA GGA GGA CAG ATT ATG TTA        542
Lys Val Lys Leu Ser Asn Lys Leu Asn Gly Gly Gly Gln Ile Met Leu
         140                 145                 150

AAC TCA TTG CAC AAA TAC GAA CCC AGG ATA CAC ATC GTG AAA GTC GGT        590
Asn Ser Leu His Lys Tyr Glu Pro Arg Ile His Ile Val Lys Val Gly
 155                 160                 165

GGG ATT CAG AAA ATG ATC AGC AGT CAG TCT TTT CCT GAG ACA CAG TTT        638
Gly Ile Gln Lys Met Ile Ser Ser Gln Ser Phe Pro Glu Thr Gln Phe
170                 175                 180                 185

ATT GCA GTC ACA GCA TAT CAG AAT GAA GAG ATT ACC GCT CTG AAA ATC        686
Ile Ala Val Thr Ala Tyr Gln Asn Glu Glu Ile Thr Ala Leu Lys Ile
                 190                 195                 200

AAA CAC AAT CCT TTT GCC AAA GCT TTC CTC GAT GCC AAA GAG AGA AGT        734
Lys His Asn Pro Phe Ala Lys Ala Phe Leu Asp Ala Lys Glu Arg Ser
                 205                 210                 215

GAC CAC AAG GAA GTC CCA GAC CAC AGC ACT GAC AAC CAG CAA TCT GGA        782
Asp His Lys Glu Val Pro Asp His Ser Thr Asp Asn Gln Gln Ser Gly
```

FIG. 1A

```
              220                    225                    230
TAT TCA CAA CTC GGT GGC TGG TTC CTG CCC AGT AAC GGC CCC ATG GGC        830
Tyr Ser Gln Leu Gly Gly Trp Phe Leu Pro Ser Asn Gly Pro Met Gly
    235                 240                 245

CCC AGC AGC AGC CCT CCT CAG TTC ATT GGG GCC CCT GTT CAC TCC TCG        878
Pro Ser Ser Ser Pro Pro Gln Phe Ile Gly Ala Pro Val His Ser Ser
250                 255                 260                 265

GGT TCG TAC TGT GAG AGA TAC TCC AGC TTG AGG AAC CAC AGA GCT GCT        926
Gly Ser Tyr Cys Glu Arg Tyr Ser Ser Leu Arg Asn His Arg Ala Ala
                270                 275                 280

CCA TAT CCC AGC CAT TAC TCC CAC CGC AGC ACT ACC ACC AAT AAC TAC        974
Pro Tyr Pro Ser His Tyr Ser His Arg Ser Thr Thr Thr Asn Asn Tyr
            285                 290                 295

ATG GAC AAC TCT TCC GGA AGT CTT GCG TCT CAT GAC AGC TGG TCA GCC       1022
Met Asp Asn Ser Ser Gly Ser Leu Ala Ser His Asp Ser Trp Ser Ala
        300                 305                 310

CTG CAG ATC CCC AAC TCC AGC GGG ATG GGA ACC CTG GCC CAC ACC ACA       1070
Leu Gln Ile Pro Asn Ser Ser Gly Met Gly Thr Leu Ala His Thr Thr
    315                 320                 325

AAC ACT ACC TCC AAC ACC AGT CAG TAC CCA AGT CTG TGG TCA GTT GCA       1118
Asn Thr Thr Ser Asn Thr Ser Gln Tyr Pro Ser Leu Trp Ser Val Ala
330                 335                 340                 345

GGG ACG ACT CTC ACC CCA TCA GGC TCA GCA TCG GGC TCC ATT ACA GGT       1166
Gly Thr Thr Leu Thr Pro Ser Gly Ser Ala Ser Gly Ser Ile Thr Gly
                350                 355                 360

GGC CTG ACA TCT CAG TTC CTA CGC GGT TCT TCG ATG TCC TAC TCG GGT       1214
Gly Leu Thr Ser Gln Phe Leu Arg Gly Ser Ser Met Ser Tyr Ser Gly
            365                 370                 375

CTG ACC TCC TCG CTG CCT GTG TCC TCT CCC TCT TCA ATG TAC GAT CCA       1262
Leu Thr Ser Ser Leu Pro Val Ser Ser Pro Ser Ser Met Tyr Asp Pro
        380                 385                 390

GGC CTA AGC GAG GTT GGC GTT GGA GAT GCC CAG TTC GAG AGC TCC ATC       1310
Gly Leu Ser Glu Val Gly Val Gly Asp Ala Gln Phe Glu Ser Ser Ile
    395                 400                 405

GCC CGG CTC ACA GCA TCA TGG GCG CCT GTG GCT CAG AGC TAC               1352
Ala Arg Leu Thr Ala Ser Trp Ala Pro Val Ala Gln Ser Tyr
410                 415                 420

TGAGATCGCT TCACATTTAA GGACTGATGC TGCAGTTATG GACTTGATCT TGGCTTCAGG     1412

AGGAAATCTA GAAGAGCTTC TTGATTTGAC AATCAGAAAA CGGGTTGATT TACTATAAAA     1472

GTCACATCTG TATCATACCG AGGCATACGT ATTTACAATC AAGATGAGAG ACAATCAATT     1532

AAAGGGTTAG TTCTTGCAAA AAAGAAAATT TTGACATCAT TTACTCACCT TTGTTTTAAA     1592

CATTGTTAAG TTTTTATTCT GTTAAACACA AAGAAGATA TTTTGAAGAA TGTTCAAAAC     1652
```

FIG. 1B

```
TGGTAACCAT TGCATAGAAG CTGTTTTACT TATGGAAGTA AATGGTTACA GGTTATCAGC    1712
ATTTTTTTAA ATATATTTTT TAGTTCAACA GAAGAAAGAA ACTCTTTAAA GTTTGGAACA    1772
ACTTGAGGGT GAGTAAATTG AGTAAAAGTA CGTTTTTGGG TTAACTATCC CTTTAACTAT    1832
CAGATTTTAG CCATACATTT TGGGGCAATT ATAGTGTTTA TTCTTGATAA TATTATCTAA    1892
AAGATTAATA AAATCAAAAT TGTGCTGTTG ACTCACTAAA AGTGTATATG TGTGTAAATA    1952
AATAGAAATT AACGTCCGGT TCATTGTAT CACAGAAGAA TGTAACAGTC TTACATGTGC     2012
TTTCTGTAGA ACGAGAGAAA GACAGACTTT GCTGTTTCGT TTGAGAAAGT GAATACGCTT    2072
TGAAAAGTGA CCGTATAGTT TTGTCTGCTA TTCGTCCTAT AGAGAAACCA TTTGTACATA    2132
TCTATCTATT TGTATTTGTT GGGCTCTTTG AGTTTTATTT ATGTCATTTT AATAATAAAT    2192
TAAATTTCTT TTTTTTTTCT GTCAAAAAAA AGGAGTTCCG GAATTC                   2238
```

FIG. 1C

A
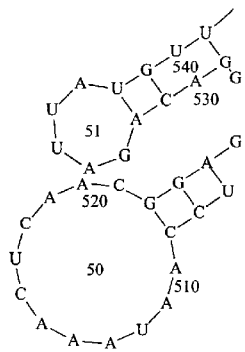
B
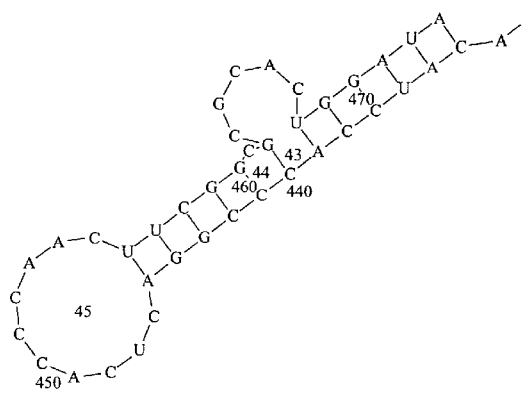
C
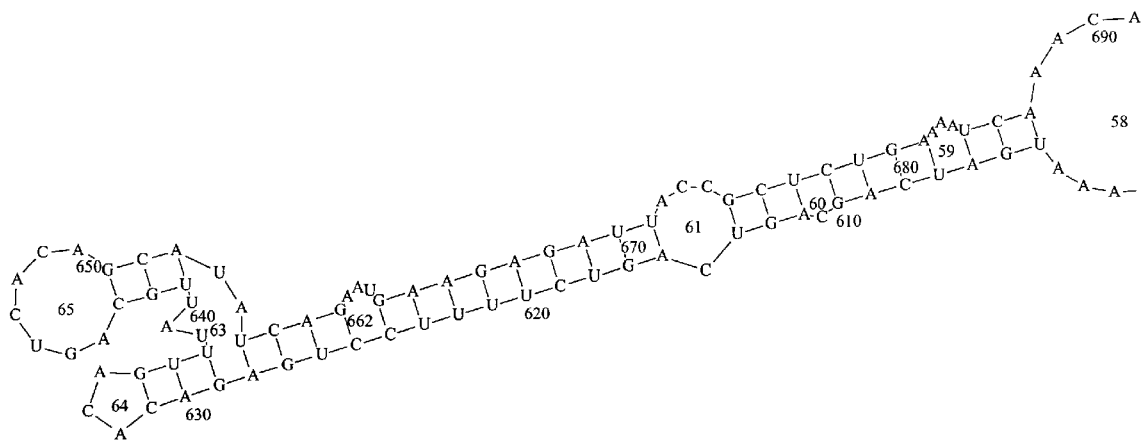
FIG. 3

A
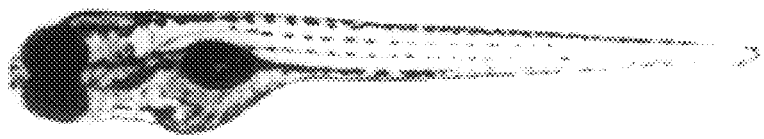
B
C  D 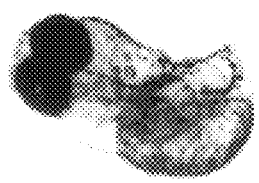
FIG. 6

A
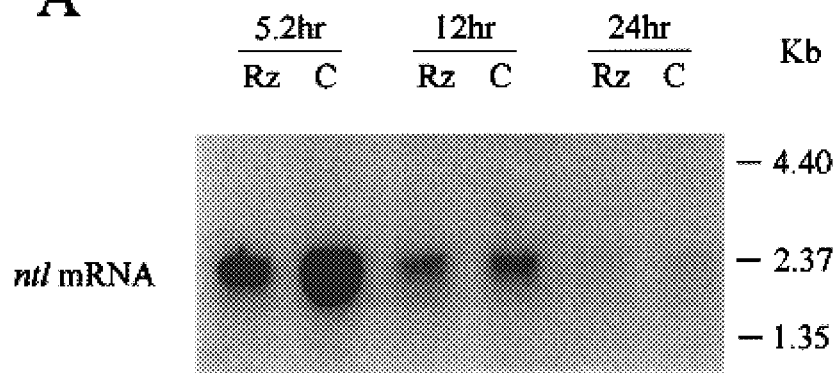
*ntl* mRNA
B
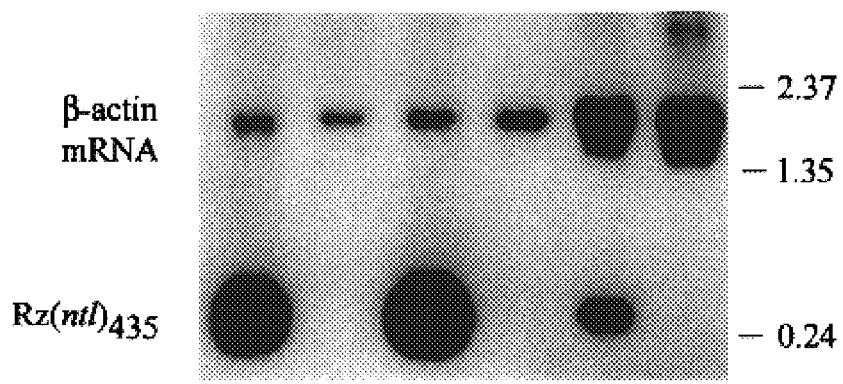
β-actin mRNA
Rz(*ntl*)$_{435}$
FIG. 7

| | | | | | |
|---|---|---|---|---|---|
| CGTCGACTGC | TGCAGTGCAG | CGTGTGGACC | CAACGACACG | CGGGCGGTAA | CCGACGTCAG | 60 |
| ACAACGGGGG | AGCGCTCCTT | TTGGCTTCCT | TCCAGGCGCG | GCGGCTGCTG | CGCTAGCTTT | 120 |
| TTTGGCCACT | GGCCGCGCGC | GGCGTAAGCG | GTTAGGCTGG | AAAGCGAAAG | CATTAAGTGG | 180 |
| CTCGCTCCCT | GTAGCCGGAG | GGTTATTTTC | CAAGGGTTGA | GTCGCAGGAC | CCCCGGTTCG | 240 |
| AGTCTCGGGC | CGGCCGGACT | GCGGCGAACG | GGGGTTTGCC | TCCCCGTCAT | GCAAGACCCC | 300 |
| GCTTGCAAAT | TCCTCCGGAA | ACAGGGACGA | GCCCCTTTTT | TGCTTTTCCC | AGATGCAGGC | 360 |
| ATGCAAGCTT | GGATCCGGAG | AGCTCCCAAC | GCGTTGGATG | CATAGCTTGA | GTATTCTATA | 420 |
| GTGTCACCTA | AATAGCTTGG | CGTAATCATG | GTCATAGCTG | TTTCCTGTGT | GAAATTGTTA | 480 |
| TCCGCTCACA | ATTCCACACA | ACATACGAGC | CGGAAGCATA | AAGTGTAAAG | CCTGGGGTGC | 540 |
| CTAATGAGTG | AGCTAACTCA | CATTATTTGC | GTTGCGCTCA | CTGCCCGCTT | TCCAGTCGGG | 600 |
| AAACCTGTCG | TGCCAGCTGC | ATTAATGAAT | CGGCCAACGC | GCGGGAGAG | GCGGTTTGCG | 660 |
| TATTGGGCGC | TCTTCCGCTT | CCTCGCTCAC | TGACTCGCTG | CGCTCGGTCG | TTCGGCTGCG | 720 |
| GCGAGCGGTA | TCAGCTCACT | CAAAGGCGGT | AATACGGTTA | TCCACAGAAT | CAGGGGATAA | 780 |
| CGCAGGAAAG | AACATGTGAG | CAAAAGGCCA | GCAAAAGGCC | AGGAACCGTA | AAAAGGCCGC | 840 |
| GTTGCTGGCG | TTTTTCGATA | GGCTCCGCCC | CCCTGACGAG | CATCACAAAA | ATCGACGCTC | 900 |
| AAGTCAGAGG | TGGCGAAACC | CGACAGGACT | ATAAAGATAC | CAGGCGGTTC | CCCCTGGAAG | 960 |
| CTCCCTCGTG | CGCTCTCCTG | TTCCGACCCT | GCCGCTTACC | GGATACCTGT | CCGCCTTTCT | 1020 |
| CCCTTCGGGA | AGCGTGGCGC | TTTCTCATAG | CTCACGCTGT | AGGTATCTCA | GTTCGGTGTA | 1080 |
| GGTCGTTCGC | TCCAAGCTGG | GCTGTGTGCA | CGAACCCCCC | GTTCAGCCCG | ACCGCTGCGC | 1140 |
| CTTATCCGGT | AACTATCGTC | TTGAGTCCAA | CCCGGTAAGA | CACGACTTAT | CGCCACTGGC | 1200 |
| AGCAGCCACT | GGTAACAGGA | TTAGCAGAGC | GAGGTATGTA | GGCGGTGCTA | CAGAGTTCTT | 1260 |
| GAAGTGGTGG | CCTAACTACG | GCTACACTAG | AAGGACAGTA | TTTGGTATCT | GCGCTCTGCT | 1320 |
| GAAGCCAGTT | ACCTTCGGAA | AAAGAGTTGG | TAGCTCTTGA | TCCGGCAAAC | AAACCACCGC | 1380 |
| TGGTAGCGGT | GGTTTTTTTG | TTTGCAAGCA | GCAGATTACG | CGCAGAAAAA | AAGGATCTCA | 1440 |
| AGAAGATCCT | TTGATCTTTT | CTACGGGGTC | TGACGCTCAG | TGGAACGAAA | ACTCACGTTA | 1500 |
| AGGGATTTTG | GTCATGAGAT | TATCAAAAAG | GATCTTCACC | TAGATCCTTT | TAAATTAAAA | 1560 |
| ATGAAGTTTT | TAATCAATCT | AAAGTATATA | TGAGTAAACT | TGGTCTGACA | GTTACCAATG | 1620 |
| CTTAATCAGT | GAGGCACCTA | TCTCAGCGAT | CTGTCTATTT | CGTTCATCCA | TAGTTGCCTG | 1680 |
| ACTCCCCGTC | GTGTAGATAA | CTACGATACG | GGAGGGCTTA | CCATCTGGCC | CCAGTGCTGC | 1740 |
| AATGATACCG | CGAGACCCAC | GCTCACCGGC | TCCAGATTTA | TCAGCAATAA | ACCAGCCAGC | 1800 |
| CGGAAGGGCC | GAGCGCAGAA | GTGGTCCTGC | AACTTTATCC | GCCTCCATCC | AGTCTATTAA | 1860 |

FIG. 8A

| | | | | | | |
|---|---|---|---|---|---|---|
| TTGTTGCCGG | GAAGCTAGAG | TAAGTAGTTC | GCCAGTTAAT | AGTTTGCGCA | ACGTTGTTGG | 1920 |
| CATTGCTACA | GGCATCGTGG | TGTCACGCTC | GTCGTTTGGT | ATGGCTTCAT | TCAGCTCCGG | 1980 |
| TTCCCAACGA | TCAAGGCGAG | TTACATGATC | CCCATGTTG | TGCAAAAAAG | CGGTTAGCTC | 2040 |
| CTTCGGTCCT | CCGATCGTTG | TCAGAAGTAA | GTTGGCCGCA | GTGTTATCAC | TCATGGTTAT | 2100 |
| GGCAGCACTG | CATAATTCTC | TTACTGTCAT | GCCATCCGTA | AGATGCTTTT | CTGTGACTGG | 2160 |
| TGAGTACTCA | ACCAAGTCAT | TGTGAGAATA | CCGCGCCCGG | CGACCGAGTT | GCTCTTGCCC | 2220 |
| GGCGTCAATA | CGGGATAATA | GTGTATGACA | TAGCAGAACT | TTAAAAGTGC | TCATCATTGG | 2280 |
| AAAACGTTCT | TCGGGGCGAA | AACTCTCAAG | GATCTTACCG | CTGTTGAGAT | CCAGTTCGAT | 2340 |
| GTAACCCACT | CGTGCACCCA | ACTGATCTTC | AGCATCTTTT | ACTTTCACCA | GCGTTTCTGG | 2400 |
| GTGAGCAAAA | ACAGGAAGGC | AAAATGCCGC | AAAAAAGGGA | ATAAGGGCGA | CACGGAAATG | 2460 |
| TTGAATACTC | ATACTCTTCC | TTTTTCAATA | TTATTGAAGC | ATTTATCAGG | GTTATTGTCT | 2520 |
| CATGAGCGGA | TACATATTTG | AATGTATTTA | GAAAAATAAA | CAAATAGGGG | TTCCGCGCAC | 2580 |
| ATTTCCCCGA | AAAGTGCCAC | CTGTATGCGG | TGTGAAATAC | CGCACAGATG | CTGAAGGAGA | 2640 |
| AAATACCGCA | TCAGGCGAAA | TTGTAAACGT | TAATATTTTG | TTAAAAATCG | CGTTAAATAT | 2700 |
| TTGTTAAATC | AGCTCATTTT | TTAACCAATA | GGCCGAAATC | GGCAAAATCC | CTTATAAATC | 2760 |
| AAAAGAATAG | ACCGAGATAG | GGTTGAGTGT | TGTTCCAGTT | TGGAACAAGA | GTCCACTATT | 2820 |
| AAAGAACGTG | GACTCCAACG | TCAAAGGGCG | AAAAACCGTC | TATCAGGGCG | ATGGCCCACT | 2880 |
| ACGTGAACCA | TCACCCAAAT | CAAGTTTTTT | GCGGTCGAGG | TGCCGTAAAG | CTCTAAATCG | 2940 |
| GAACCCTAAA | GGGAGCCCCC | GATTTAGAGC | TTGACGGGGA | AAGCCGGCGA | ACTGGGCGAG | 3000 |
| AAAGGAAGGG | AAGAAAGCGA | AAGGAGCGGG | CGCTAGGGCG | CTGGCAAGTG | TAGCGGTCAC | 3060 |
| GCTGCGCTGA | ACCACCACAC | CCGCCGCGCT | TAATTGCGCC | GTACAGGGCG | CGTCCATTCG | 3120 |
| CCATTCAGGC | TGCGCAACTG | TTGGGAAGGG | CGATCGGTGC | GGGCCTCTTC | GCTATTACCC | 3180 |
| AGCTGGCCAA | AGGGGGATGT | GCTGCAAGGC | GATTAAGTTG | GGTAACGCCA | GGGTTTTCCC | 3240 |
| AGTCACGACG | TTGTAAACGA | CGGCCAGTGA | ATTGTAATAC | GACTCACTAT | AGGGCGAATT | 3300 |
| GGGCCCGACG | TCGCATGCTC | CTCTAGACCG | TGCAAAAGGA | GAGCCTGTAA | GGGCACTCTT | 3360 |
| CCGTGGTCTG | GTGGATAAAT | TCGCAAGGGT | ATCATGGCGG | ACGACCGGGG | TTCGAACCCC | 3420 |
| GGATCCGGCC | GTCCGCCGTG | ATCCATGCGG | TTACCGCCCG | CGTGTCGAAC | CCAGGTGTGC | 3480 |
| GACGT | | | | | | 3485 |

FIG. 8B

```
GGGAAAACAG GTGTGTTTCT GCCTTTTACT TCTAACTTGG AATACCTTAC CCAATCCCAG    60
TTCTTCATCT CCTCTGAGAA GTTATAGGGT TAAAAATATT GTCTTCTTAC ATCAGCAGAT   120
ATATGACAAG GGAAGAGATC CTTTGGTCAG CTCTAGTAAT CTGGCTTTGT CCCCCTTAGG   180
GAATAGACTT TGGCCTGAGG GAACAGCTCA GACTGAGGCG TGCAGCAGGC TCAGGAGGAA   240
GAAGGGCGGT AGAAGCAGAG GAAGTGGCCT TGCCTGGCCA CAAGGGCTCT GAGGGTCCCT   300
GCCTGAAGAG GGAGAGGAGA TCCGGGCCAG GGCAGGTGC TCTGGAATGC AGCCCCAGTT    360
GCTGCTGCTG CTGCTCTTGC CACTCAATTT CCCTGTCATC CTGACCAGAG AGCTTCTGTG   420
TGGAGGATCC CCAGAGCCCT GTGCCAACGG AGGCACCTGC CTGAGGCTAT CTCGGGGACA   480
AGGGATCTGC CAGTGTGCCC CTGGATTTCT GGGTGAGACT TGCCAGTTTC CTGACCCCTG   540
CAGGGATACC CAACTCTGCA AGAATGGTGG CAGCTGCCAA GCCCTGCTCC CCACACCCCC   600
AAGCTCCCGT AGTCCTACTT CTCCACTGAC CCTCACTTC TCCTGCACCT GCCCTCTGG    660
CTTCACCGGT GATCGATGCC AAACCCATCT GGAAGAGCTC TGTCCACCTT CTTTCTGTTC   720
CAACGGGGGT CACTGCTATG TTCAGGCCTC AGGCCGCCCA CAGTGCTCCT GCGAGCCTGG   780
GTGGACAGGT GAGCAATGCC AGCTCCGAGA CTTCTGCTCA GCCAACCCCT GTGCCAACGG   840
AGGCGTGTGC CTGGCCACAT ACCCCCAGAT CCAGTGCCGC TGTCCACCTG GGTTCGAGGG   900
TCACACCTGT GAACGCGACA TCAACGAGTG CTTCCTGGAG CCGGGACCCT GCCCTCAGGG   960
CACCTCCTGC CATAACACCT TGGGTTCCTA CCAGTGTCTC TGCCCTGTGG GGCAGGAACG  1020
TCCCCAGTGC AAGCTCAGGA AGGGAGCCTG CCCTCCTGGA AGCTGTCTCA ATGGGGGCAC  1080
CTGCCAGCTG GTCCCAGAGG GACACTCCAC CTTTCATCTC TGCCTCTGTC CCCCAGGTTT  1140
CACGGGGCTG GACTGTGAGA TGAACCCAGA TGACTGTGTC AGGCACCAGT GTCAGAACGG  1200
GGCCACCTGT CTGGATGGGC TGGATACCTA CACCTGCCCC TGCCCCAAGA CATGGAAGGG  1260
CTGGGACTGC TCTGAAGATA TAGATGAATG TGAAGCCCGG GGTCCCCCTC GCTGCAGGAA  1320
CGGTGGCACC TGCCAGAACA CAGCTGGCAG CTTTCACTGT GTGTGCGTGA GTGGCTGGGG  1380
AGGTGCAGGC TGTGAGGAGA ACCTGGATGA CTGTGCAGCT GCCACCTGTG CCCCGGGATC  1440
CACCTGCATC GACCGTGTGG GCTCTTTCTC CTGCCTCTGC CCACCTGGAC GCACAGGCCT  1500
CCTGTGCCAC CTGGAAGACA TGTGTTTGAG TCAGCCGTGC ACGTGAATG CCCAGTGCAG    1560
CACCAACCCT CTGACAGGCT CCACCCTCTG CATATGCCAG CCTGGCTACT CAGGATCCAC  1620
CTGTCACCAA GATCTGGATG AGTGCCAAAT GGCCCAGCAA GGACCCAGTC CTGCGAACA    1680
TGGGGGGTCC TGCATCAACA CCCTGGCTC CTTCAACTGC CTCTGCCTGC CTGGTTACAC   1740
GGGCTCCCGC TGTGAAGCTG ACCACAATGA GTGCCTGTCA CAGCCCTGCC ACCCAGGCAG  1800
CACCTGCCTG GACCTGCTTG CAACCTTCCA CTGCCTCTGC CCACCAGGCT GGAAGGGAG   1860
```

FIG. 9A

```
ACTCTGTGAG GTGGAGGTCA ATGAGTGCAC CTCTAATCCC TGCCTGAACC AAGCTGCCTG   1920
CCATGACCTG CTCAACGGCT TCCAGTGCCT CTGCCTTCCT GGATTCACCG GCGCCCGATG   1980
TGAGAAAGAC ATGGACGAGT GTAGCAGCAC CCCCTGTGCC AATGGGGGC GCTGCCGAGA    2040
CCAGCCTGGA GCCTTCTACT GCGAGTGTCT CCCAGGCTTT GAAGGGCCAC ACTGTGAGAA   2100
AGAAGTGGAC GAATGTCTGA GTGACCCCTG TCCCGTGGGA GCCAGCTGTC TTGATCTCCC   2160
CGGAGCATTC TTCTGTCTCT GCCGTCCTGG TTTCACAGGT CAACTTTGTG AGGTTCCCTT   2220
GTGCACCCCC AACATGTGCC AACCTGGACA GCAATGCCAA GGTCAGGAAC ACAGAGCCCC   2280
CTGCCTCTGC CCTGACGGAA GTCCTGGCTG TGTTCCTGCC GAGGACAACT GCCCCTGTCA   2340
CCATGGCCAT TGCCAGAGAT CCTTGTGTGT GTGTGATGAG GCTGGACTG GACCAGAATG    2400
CGAGACAGAA CTGGGTGGCT GCATCTCCAC ACCCTGTGCC CATGGGGGA CCTGCCACCC    2460
ACAGCCATCT GGCTACAACT GTACCTGCCC TGCAGGCTAC ATGGGGTTGA CCTGTAGTGA   2520
GGAGGTGACA GCTTGTCACT CAGGGCCCTG TCTCAATGGT GGCTCCTGCA GCATCCGTCC   2580
TGAGGGCTAT TCCTGCACCT GCCTTCCAAG TCACACAGGT CGCCACTGCC AGACTGCCGT   2640
GGACCACTGT GTGTCTGCCT CGTGCCTCAA TGGGGTACC TGTGTGAACA AGCCTGGCAC    2700
TTTCTTCTGC CTCTGTGCCA CTGGCTTCCA GGGGCTGCAC TGTGAGGAGA AGACTAACCC   2760
CAGCTGTGCA GACAGCCCCT GCAGGAACAA GGCAACCTGC CAAGACACAC CTCGAGGGGC   2820
CCGCTGCCTC TGCAGCCCTG GCTATACAGG AAGCAGCTGC CAGACTCTGA TAGACTTGTG   2880
TGCCCGGAAG CCCTGTCCAC ACACTGCTCG ATGCCTCCAG AGTGGGCCCT CGTTCCAGTG   2940
CCTGTGCCTC CAGGGATGGA CAGGGGCTCT CTGTGACTTC CCACTGTCCT GCCAGAAGGC   3000
CGCGATGAGC CAAGGCATAG AGATCTCTGG CCTGTGCCAG AATGGAGGCC TCTGTATTGA   3060
CACGGGCTCC TCCTATTTCT GCCGCTGCCC TCCTGGATTC AAGGCAAGT TATGCCAGGA    3120
TAATGTGAAC CCCTGCGAGC CAATCCCTG CCATCACGGG TCTACCTGTG TGCCTCAGCC    3180
CAGTGGCTAT GTCTGCCAGT GTGCCCCAGG CTATGAGGGA CAGAACTGCT CAAAAGTACT   3240
TGACGCTTGT CAGTCCCAGC CCTGCCACAA CCACGGAACC TGTACCTCCA GGCCTGGAGG   3300
CTTCCACTGT GCCTGCCCTC AGGCTTCGT GGGACTGCGC TGTGAGGGAG ATGTGGATGA    3360
GTGTCTGGAC CGGCCCTGTC ACCCCTCGGG CACTGCAGCT TGCCACTCTT TAGCCAACGC   3420
CTTCTACTGC CAGTGTCTGC CTGGGCACAC AGGCCAGCGG TGTGAGGTGG AGATGGACCT   3480
CTGTCAGAGC CAACCCTGCT CCAATGGAGG ATCCTGTGAG ATCACAACAG GCCACCCCC   3540
TGGCTTCACC TGTCACTGCC CAAGGGTTT TGAAGGCCCC ACCTGCAGCC ACAAAGCCCT    3600
TTCCTGCGGC ATCCATCACT GCCACAATGG AGGCCTATGT CTGCCCTCCC CTAAGCCAGG   3660
```

FIG. 9B

```
GTCACCACCG CTCTGTGCCT GCCTCAGTGG TTTTGGGGGC CCTGACTGTC TGACACCTCC    3720
AGCTCCACCG GGCTGCGGTC CCCCCTCACC CTGCCTGCAC AATGGTACCT GCACTGAGAC    3780
CCCTGGGTTG GGCAACCCGG GCTTTCAATG CACCTGCCCT CCTGACTCTC CAGGGCCCCG    3840
GTGTCAAAGG CCAGGGGCAA GTGGGTGTGA GGGCCGAGGT GGTGATGGGA CCTGCGATGC    3900
TGGCTGCAGT GGCCCAGGAG GAGACTGGGA TGGAGGGGAC TGTTCCCTGG GGGTCCCAGA    3960
CCCCTGGAAG GGCTGTCCCC CGCATTCCCA GTGCTGGCTT CTGTTCCGGG ACGGACGGTG    4020
TCACCCGCAG TGTGACTCTG AGGAGTGTCT CTTTGATGGC TACGACTGTG AAATCCCTCC    4080
AACCTGCATC CCAGCCTATG ACCAGTACTG CCGAGATCAC TTCCACAACG GCACTGTGA    4140
GAAAGGCTGC AATAACGCTG AATGTGGCTG GACGGGGGA GACTGCAGAC CAGAAGGGGA    4200
AGACTCAGAG GGGAGGCCCT CCCTGGCCCT GCTGGTGGTG CTGAGGCCCC CAGCCCTGGA    4260
TCAGCAGCTG CTTGCCCTGG CACGAGTGCT GTCCCTGACT CTGAGGGTCG GTCTCTGGGT    4320
GAGGAAGGAC AGTGAAGGCA GGAACATGGT GTTCCCCTAT CCTGGGACCC GGGCCAAAGA    4380
GGAGCTGAGT GGAGCTAGGG ATTCCTCTTC ATGGGAAAGA CAAGCCCCTC CCACTCAGCC    4440
CCTGGGCAAG GAGACAGAGT CTCTTGGTGC AGGGTTTGTG GTAGTGATGG GAGTGGATCT    4500
GTCCCGCTGT GGTCCGGAAC ATCCTGCGTC CCGCTGCCCC TGGGACTCTG GACTCCTGCT    4560
GCGCTTCCTT GCAGCAATGG CAGCAGTGGG AGCTCTGGAG CCCCTGCTGC CTGGACCCTT    4620
GCTGGCGGCT CACCCTCAAG CAGGGACCAG GCCCCCTGCC AACCAGCTTC CCTGGCCCAT    4680
TCTATGTTCA CCAGTGGTTG GGGTGCTTCT CCTGGCCCTT GGGGCCCTTC TCGTCCTCCA    4740
GCTCATTCGG CGACGGCGAC GAGAACATGG GGCCCTGTGG CTGCCCCCTG GTTTCATTCG    4800
AAGGCCTCAG ACACAGCAGG CACCCCACCG GCGGAGGCCC CCACTGGGCG AGGACAACAT    4860
TGGTCTTAAG GCACTGAAGC CAGAGGCCGA AGTGGATGAG GATGGAGTGG CCATGTGCTC    4920
GGGCCCTGAA GAGGGAGAGG CTGAAGAAAC AGCCTCAGCC TCCAGGTGCC AGCTTTGGCC    4980
GCTCAACAGC GGCTGTGGAG AGCTCCCCCA GGCAGCCATG CTGACCCCTC CTCAGGAGTG    5040
TGAATCGGAG GTTCTGGATG TGGACACCTG TGGACCTGAT GGGGTGACAC CCCTGATGTC    5100
AGCCGTCTTC TGTGGGGGAG TGCAGTCCAC GACTGGGGCT AGTCCACAGA GACTGGGGCT    5160
AGGAAATCTG GAACCCTGGG AACCACTGCT GGATAGAGGG GCCTGCCCCC AGGCTCACAC    5220
TGTGGGCACT GGAGAGACGC CTCTGCACCT AGCTGCCAGA TTCTCTCGGC CAACCGCTGC    5280
CCGCCGCCTC CTTGAGGCTG GAGCCAACCC CAACCAGCCA GACCGCGCTG GGCGCACCCC    5340
ACTTCACACT GCTGTGGCTG CCGACGCTCG GGAGGTTTGC CAGCTCCTAT TGGCCAGCAG    5400
ACAGACTACG GTGGACGCCC GCACAGAGGA CGGGACTACA CCTTTGATGC TGGCTGCCAG    5460
```

FIG. 9C

```
GCTGGCCGTG GAGGACCTGG TTGAAGAATT GATCGCAGCC CGAGCAGATG TAGGAGCCAG     5520
GGATAAAAGG GGAAAAACTG CACTGCACTG GCCGCTGCT  GTGAACAACG CCCGAGCCGC     5580
CCGCTCTCTC CTCCAGGCTG GAGCGGATAA AGATGCCCAG GACAGTAGGG AACAGACGCC     5640
GCTTTTCCTG GCAGCGCGCG AAGGAGCCGT GGAGGTGGCG CAGCTGTTGC TGGAGCTCGG     5700
GGCGGCCCGG GGACTGCGAG ACCAGGCCGG GCTGGCCCCA GGAGATGTGG CCCGCCAGCG     5760
CAGTCACTGG GACCTGCTAA CGCTGCTGGA AGGGCTGGA  CCGACTACGC AGGAGGCCCG     5820
TGCGCACGCA CGCACCACGC CGGGGGGCGG GTCCGCCCCG CGCTGCCGGA CGCTGTCTGC     5880
GGGAGCGCGC CCGCGCGGGG GCGGAGCCTG TCTGCAGGCT CGCACTTGGT CGGTGGACTT     5940
GGGAGCGCGC GGAGGGAAGG TGTATGCTCG CTGCCGGAGC CGATCTGGAA GCTGCGGAGG     6000
CCCCACCACG CGCGGCCGCA GGTTCTCCGC GGGCTCCCGT GGACGACGCG GGGCTAGGGC     6060
ATCACAGGAT GACTGGCCTC GCGACTGGGT GGCCCTGGAA GCCTGCGGCT CCGCCTGCAG     6120
TGCGCCGATC CCGCCTCCCA GCCTGACCCC GTCCCAGAA  CGTGGATCCC CTCAAGTTGC     6180
CTGGGGTCTT CCAGTTCACC AAGAGATTCC CTTAAACTCG GTTGTAAGAA ATCTGAACTA     6240
GGCAGCTGCG TGAAGGAAG  GAAGCGACAC GTACGAGTCT GGAAGACTCC GGACTTTTAA     6300
GGCCAAAATA ACCGTTAAGC TCACTTGTCT CCCCCATAGA GTATGCACAG CAATGGGAAG     6360
AGGGTTTAGG ATGTCCGGTT GAGATAGACC GTGATTTTCC TGGAAAATAG GGCAGCTTCA     6420
AGAGGACAAA GTTGATTTCG AGAATCCCTA AACTCTGGAA CCAAGAACTG TGGGCGAATT     6480
GGGTGTAAAA TGTTTCTTGT GTATGGTTTC CCAAAAGGAG CCTCTGCTAT CTACTGCCCA     6540
CAAGTAGCTG GCAACTATTT ATTAAGCACC TACGATGTGC CGGGTGTTGT GTAGATGAAC     6600
AGTAAGTAAC CAGTGGCCCA TCCAGCTGAT GACTCCTTGC CCTCTCTCTG CCTCCCCACA     6660
AGGACACTGG TGCAGGG                                                    6677
```

COMPOSITIONS AND METHODS FOR THE USE OF RIBOZYMES TO DETERMINE GENE FUNCTION

FIELD OF THE INVENTION

The present invention provides nucleic acid sequences and methods to determine gene function. In particular, the present invention relates to reducing the levels of RNA encoded by a DNA sequence of interest using ribozymes. The present invention further relates to ribozyme sequences, recombinant expression vectors encoding ribozymes as well as host cells and transgenic animals comprising such expression vectors.

BACKGROUND OF THE INVENTION

The human genome project and allied interests will soon have elucidated the sequence of the entire human genome [Cox et al (1994) *Science* 265:2031–2031; Guyer et al (1995) *Proc. Natl. Acad. Sci. USA* 92:10841–10848]. While this anticipated advance is exciting, it is also misleading since knowledge of the sequences of open reading frames and genetic coding regions, without a knowledge of the function of the gene products of this vast array of putative genes, provides only very limited insight into the human genome. Full knowledge of the genome requires knowledge of the function of each of the gene products of the putative genetic coding sequences. While gene function determination is ongoing within the field of molecular genetics, the rate at which the function of a gene can be determined is many orders of magnitude slower than the rate at which a gene can be sequenced. Therefore, a massive backlog of genetic sequences in search of a function looms on the horizon.

One of the traditionally used means of determining gene function is by "knocking out" or disrupting the coding sequence in an animal model and observing which structure (s) or function(s) is deleted in the resulting "knock out" model [Capecchi et al (1989) *Science* 244:1288–1292; Hasty et al (1991) *Nature* 350:243–246]. Gene knockouts are presently accomplished by homologous recombination in embryonic stem (ES) cells with a targeting vector, production of mosaic animals (in particular, mice) with a single disrupted allele in some of their germ cells, breeding to mice which are heterozygous for the disrupted gene, and finally inbreeding to venerate homozygous mice where the targeted gene disruption is present in each allele so that the full gene complement is rendered non-functional [Shastry et al (1994) *Mol. Cellul. Biochem.* 136:171–182; Galli-Taliadoros et al (1995) *J. Immunol. Methods* 181:1–15]. Only when each of these very time consuming steps has been successfully accomplished will a gene knockout mouse, which will show the phenotype associated with deletion of the targeted gene, be available for further determination of the function of the deleted gene. Clearly, this is a complex and slow method for gene function determination and cannot be expected, in a reasonable time, to yield the function of the many tens of thousands of coding sequences elucidated by the present flurry of genetic sequencing.

Therefore, there remains a need for a rapid and specific means for the determination of gene function.

SUMMARY OF THE INVENTION

The present invention provides methods for the identification of one or more functions of a nucleotide sequence in an organism which are useful for the rapid identification of, for example, disease related genes which may be targeted for the treatment or prevention of disease. The invention further provides recombinant expression vectors which encode ribozyme sequences, transgenic host cells, transgenic embryos and transgenic organisms which express a ribozyme sequence that is capable of cleaving mRNA encoded by the nucleotide sequence whose function is sought to be determined. The ribozyme sequences, recombinant expression vectors, transgenic host cells, transgenic embryos and transgenic organisms provided by the present invention are useful in identifying the function of any sequence of interest in an organism.

In one embodiment, the invention provides a ribozyme sequence capable of cleaving RNA, wherein the RNA is encoded by SEQ ID NO:5. While not restricted to any particular ribozyme sequence, in one preferred embodiment, the ribozyme sequence is selected from the group consisting of SEQ ID NO:19, SEQ ID NO:20 and SEQ ID NO:21.

In another embodiment, the invention contemplates a DNA sequence encoding a ribozyme sequence capable of cleaving RNA encoded by a nucleic acid sequence selected from the group consisting of SEQ ID NO:5 and SEQ ID NO:27. Although it is not intended that the DNA sequence be limited to any particular sequence, in one preferred embodiment, the DNA sequence is selected from the group consisting of DNA sequences encoding SEQ ID NO:19, SEQ ID NO:20, and SEQ ID NO:21.

In yet another embodiment, the invention provides a recombinant expression vector comprising a DNA sequence encoding a ribozyme sequence capable of cleaving RNA encoded by SEQ ID NO:5. While not restricted to any ribozyme sequence, in a preferred embodiment, the ribozyme sequence is selected from the group consisting of SEQ ID NO:19, SEQ ID NO:20 and SEQ ID NO:21. In an alternative embodiment, it is preferred, though not required, that the recombinant expression vector is selected from the group consisting of $pT_7vaRz_{435}$, $pT_7vaRz_{365}$, and $pT_7vaRz_{564}$. In a particularly preferred embodiment, the recombinant expression vector is selected from the group consisting of $pT_7GaRz_{435}$, $pT_7GaRz_{365}$ and $pT_7GaRz_{564}$.

Also provided by the invention is a host cell comprising a recombinant expression vector wherein the recombinant expression vector comprises a DNA sequence encoding a ribozyme sequence capable of cleaving RNA encoded by a nucleic acid sequence selected from the group consisting of SEQ ID NO:5 and SEQ ID NO:27. While not restricted to a particular host cell, one preferred embodiment contemplates that the host cell is a fertilized egg.

The invention further provides a transgenic zebrafish cell comprising a heterologous ribozyme sequence capable of cleaving an RNA sequence comprised in the zebrafish cell. In one preferred embodiment, the transgenic zebrafish cell is a fertilized egg. In an alternative embodiment, the transgenic zebrafish cell is an embryonic cell. In yet another alternative embodiment, the transgenic zebrafish cell is an adult cell.

The present invention further provides a method for identifying one or more functions of a DNA sequence of interest comprised in a genome of an organism, comprising: a) providing: i) a cell derived from the organism, wherein the cell comprises the DNA sequence of interest encoding RNA sequence; and ii) a ribozyme sequence capable of cleaving the RNA sequence; b) introducing the ribozyme sequence into the derived cell to generate a manipulated cell, wherein the introducing is under conditions such that the RNA sequence is cleaved by the ribozyme sequence; and c) detecting one or more changes in the manipulated cell relative to the derived cell thereby identifying one or more functions of the DNA sequence in the organism.

The present invention also provides a method for identifying one or more functions of a DNA sequence of interest comprised in a genome of an organism, comprising: a) providing: i) a cell derived from the organism, wherein the cell comprises the DNA sequence of interest encoding RNA sequence; and ii) a ribozyme sequence capable of cleaving the RNA sequence; b) introducing the ribozyme sequence into the derived cell to generate a manipulated cell, wherein the introducing is under conditions such that the RNA sequence is cleaved by the ribozyme sequence; c) permitting the manipulated cell to generate progeny cells; and d) detecting one or more changes in at least one of the progeny cells relative to the derived cell thereby identifying one or more functions of the DNA sequence of interest in the organism.

Also provided by the present invention is a method for identifying one or more functions of a first DNA sequence of interest comprised in a genome of a first organism, comprising: a) providing: i) a cell derived from a second organism, wherein the derived cell comprises a genome comprising a second DNA sequence homologous to the first DNA sequence, and wherein the second DNA sequence encodes RNA sequence; and ii) an expression vector comprising a third DNA sequence encoding a ribozyme sequence capable of cleaving a substrate cleavage sequence in the encoded RNA sequence, wherein the third DNA sequence is operably linked to a promoter sequence; b) introducing the expression vector into the derived cell to generate a manipulated cell, wherein the introducing is under conditions such that the ribozyme sequence is expressed and wherein the encoded RNA sequence is cleaved by the expressed ribozyme sequence; c) permitting the manipulated cell to generate progeny cells; and d) detecting one or more changes in at least one of the progeny cells relative to the derived cells thereby identifying one or more functions for the first DNA sequence of interest in the first organism.

The present invention additionally a method for identifying one or more functions of a first DNA sequence comprised in a genome of a first organism, comprising: a) providing: i) a cell derived from a second organism, wherein the cell comprises a genome comprising a second DNA sequence homologous to the first DNA sequence; ii) a first expression vector comprising a DNA sequence encoding, a ribozyme sequence capable of cleaving a substrate cleavage sequence in the second DNA sequence wherein the DNA sequence is operably linked to a promoter sequence: and iii) a second expression vector comprising a coding sequence for an RNA polymerase operably linked to a cognate promoter of the RNA polymerase; iv) the RNA polymerase; b) introducing the first expression vector, the second expression vector, and the RNA polymerase into the derived cell to generate a manipulated cell, wherein the introducing is under conditions such that the ribozyme sequence is expressed and wherein the second DNA sequence is cleaved by the expressed ribozyme sequence; c) permitting the manipulated cell to generate progeny cells; and d) detecting one or more changes in at least one of the progeny cells relative to the derived cell thereby identifying one or more functions for the first DNA sequence in the first organism.

The present invention also provides a method for identifying one or more functions of a first DNA sequence comprised in a genome of a first organism, comprising: a) providing: i) a cell derived from a second organism, wherein the derived cell comprises a genome comprising a second DNA sequence homologous to the first DNA sequence, and wherein the second DNA sequence encodes an RNA sequence; and ii) a ribozyme sequence capable of cleaving the RNA sequence; b) introducing the ribozyme sequence into the derived cell to generate a manipulated cell, wherein the introducing is under conditions such that the RNA sequence is cleaved by the ribozyme sequence; and c) detecting one or more changes in the manipulated cell relative to the derived cell thereby identifying at least one function for the first DNA sequence in the first organism.

While not limited to any particular organism, in one preferred embodiment, the first organism is human and the second organism is zebrafish. In an alternative preferred embodiment, the organism is human and the second organism is murine.

Although it is not contemplated that the ribozyme is restricted to any particular sequence, in one embodiment, the ribozyme is selected from the group consisting of group I intron ribozyme, ribonuclease P ribozyme, hammerhead ribozyme, hairpin ribozyme and hepatitis delta virus ribozyme. In a preferred embodiment, the ribozyme is a hammerhead ribozyme comprising a first substrate binding region, a second substrate binding region and a catalytic region, and wherein the first and second binding regions consist of 8 nucleotides.

While not intending to restrict the three-dimensional configuration of the second DNA sequence in which the substrate cleavage sequence is contained, in one embodiment, the substrate cleavage sequence is contained in a loop structure in the second DNA sequence. In a particularly preferred embodiment, the loop structure is selected from the group consisting of a 9-nucleotide loop, a 12-nucleotide loop and a 14-nucleotide loop.

Without intending to limit the promoter sequence to any particular sequence, in one preferred embodiment, the promoter sequence comprises an adenovirus type 2-associated RNA I gene promoter sequence. In a yet more preferred embodiment, the promoter sequence further comprises a promoter sequence selected from the group consisting of tRNA, CMV, RSV, SV40, PEPCK, MT, SRα, P450 family, GAL7, $T_7$, $T_3$, SP6, K11 and heat shock protein promoter sequences. In an alternative preferred embodiment, the promoter sequence comprises a CMV promoter sequence, a $T_7$ promoter sequence, and a vaRNA I promoter sequence.

Although it is not intended that the scope of the invention be limited to any particular cell type, in one preferred embodiment, the derived cell is an embryonic cell.

Additionally, it is contemplated that the methods of the invention are not limited to any particular type of expression. In one preferred embodiment, expression is transient. In an alternative preferred embodiment the expression is stable.

The invention further provides a method for identifying one or more functions of a first DNA sequence comprised in a genome of a first organism, comprising: a) providing: i) an oocyte derived from a second organism, wherein the derived oocyte comprises a genome comprising a second DNA sequence homologous to the first DNA sequence, and wherein the second DNA sequence encodes an RNA sequence; and ii) a ribozyme sequence capable of cleaving the RNA sequence; b) introducing the ribozyme sequence into the derived oocyte to generate a manipulated oocyte, wherein the introducing is under conditions such that the RNA sequence is cleaved by the ribozyme sequence; and c) detecting one or more changes in the manipulated oocyte relative to the derived oocyte thereby identifying at least one function for the first DNA sequence in the first organism.

Also provided ny the present invention is a method for identifying one or more functions of a first DNA sequence comprised in a genome of a first organism, comprising: a) providing: i) a cell derived from a second organism, wherein the derived cell is transparent and comprises a genome comprising a second DNA sequence homologous to the first DNA sequence, and wherein the second DNA sequence encodes an RNA sequence; and ii) a ribozyme sequence capable of cleaving the RNA sequence; b) introducing the ribozyme sequence into the derived cell to generate a manipulated cell, wherein the introducing is under conditions such that the RNA sequence is cleaved by the ribozyme sequence; and c) detecting one or more changes in the manipulated cell relative to the derived cell thereby identifying at least one function for the first DNA sequence in the first organism.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 1A–1C show the nucleic acid sequence (SEQ ID NO:5) and predicted amino acid sequence (SEQ ID NO:6) of the zebra fish ntl cDNA.

FIGS. 3 (parts A–C) show a graphic representation of the secondary structure and nucleotide sequence of zebrafish ntl mRNA (A) loop 50, (B) loop 45 and (C) loop 65.

FIGS. 6A–D show phenotypes of zebrafish at 96 hours of embryogenesis from (a) wild-type zebrafish, (b) partial no tail from zebrafish developing from eggs injected with pT$_7$vaRz(ntl)$_{435}$, pT$_7$T$_7$ and T$_7$ RNAP, (c) no tail from zebrafish developing from eggs injected with pT$_7$vaRz(ntl)$_{435}$, pT$_7$T$_7$ and T$_7$ RNAP, (d) homozygous no tail mutant zebrafish (ntl$^{b195}$).

FIGS. 7A–B show an X-ray of a Northern blot of RNA isolated from fertilized zebrafish eggs injected with pT$_7$vaRz (ntl)$_{435}$, pT$_7$T$_7$ and T$_7$ RNA polymerase.

FIGS. 8A–8B show the nucleic acid sequence (SEQ ID NO:10) of the expression vector pGvaL.

FIGS. 9A–9D show the cDNA sequence (SEQ ID NO:27) for the mouse Notch 4 gene.

DEFINITIONS

Figure 2:
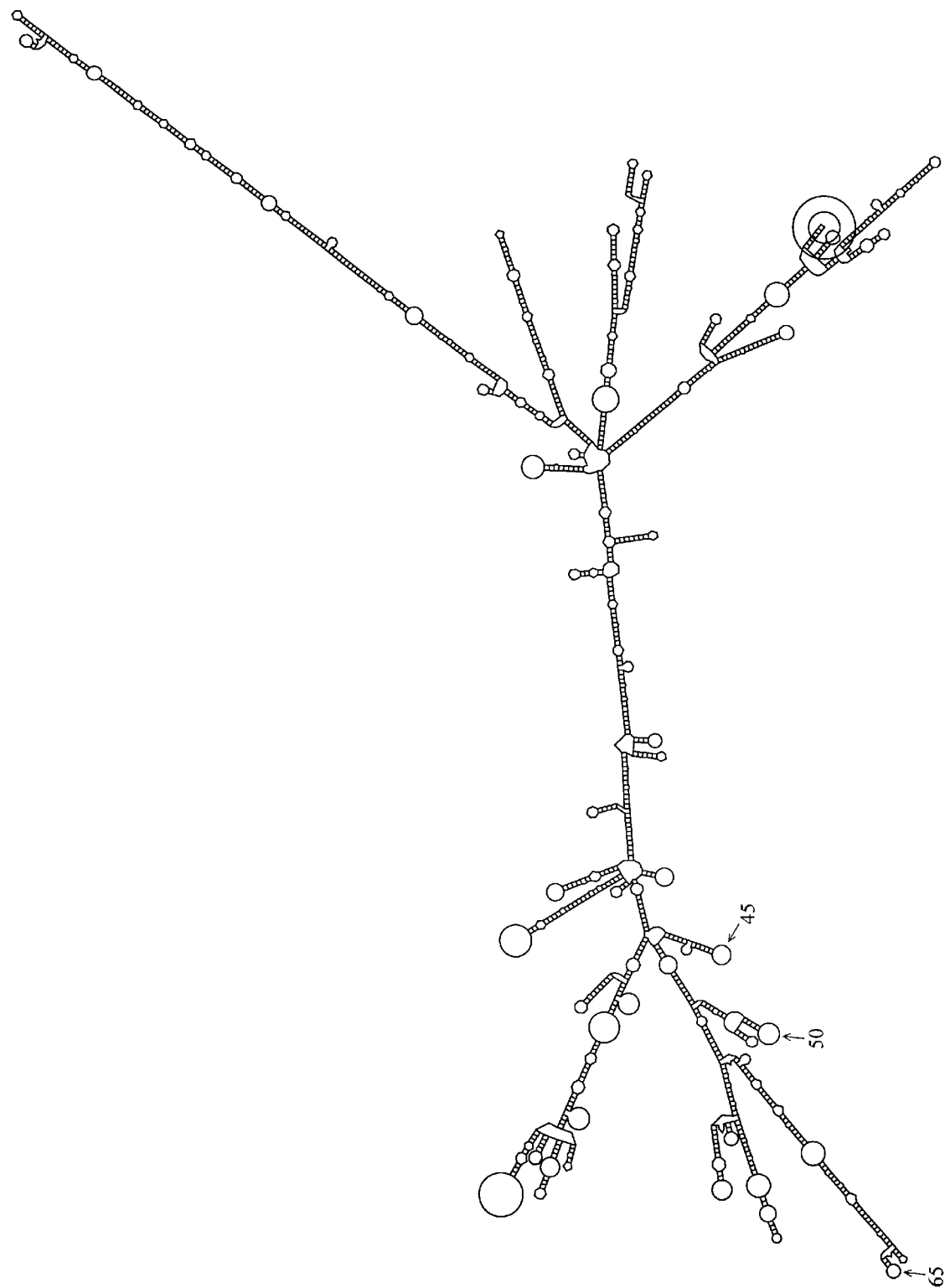
FIG. 2 shows a graphic representation of the secondary structure of zebrafish ntl mRNA obtained by the "RNADRAW" program.

To facilitate understanding of the invention, a number of terms are defined below.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "portion" when used in reference to a nucleotide sequence refers to fragments of that nucleotide sequence. The fragments may range in size from 5 nucleotide residues to the entire nucleotide sequence minus one nucleic acid residue.

The term "recombinant DNA molecule" as used herein refers to a DNA molecule which is comprised of segments of DNA joined together by means of molecular biological (i.e., non-naturally occurring) techniques.

As used herein, the terms "vector" and "vehicle" are used interchangeably in reference to nucleic acid molecules that transfer DNA segment(s) from one cell to another.

The term "expression vector" or "expression cassette" as used herein refers to a recombinant DNA molecule containing a desired coding sequence and appropriate nucleic acid sequences necessary for the expression of the operably linked coding sequence in a host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the terms "complementary" or "complementarity" are used in reference to "polynucleotides" and "oligonucleotides" (which are interchangeable terms that refer to a sequence of nucleotides) related by the base-pairing rules. For example. for the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml:5 g Ficoll (Type 400, Pharmacia), 5 g BSA (Fraction V; Sigma)] and 100 μg/ml denatured salmon sperm DNA followed by washing, in a solution comprising 5× SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or (genomic clone, the term "substantially homologous" refers to any probe which can hybridize to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) to the single-stranded nucleic acid sequence under conditions of low stringency as described above.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (as determined, e.g., by $C_0t$ or $R_0t$ analysis) or between one nucleic acid sequence present in solution and another nucleic acid sequence immobilized to a solid support [e.g, a nylon membrane or a nitrocellulose filter as employed in Southern and Northern blotting, dot blotting or a glass slide as employed in in situ hybridization, including FISH (fluorescent in situ hybridization)].

"Stringency" when used in reference to nucleic acid hybridization typically occurs in a range from about $T_m-5°$ C. (5° C. below the $T_m$ of the probe) to about 20° C. to 25° C. below $T_m$. The term "$T_m$" is used in reference to the "melting temperature." The melting temperature is the temperature at which a population of double-stranded nucleic acid molecules becomes half dissociated into single strands.

As will be understood by those of skill in the art, a stringent hybridization can be used to identify or detect identical polynucleotide sequences or to identify or detect similar or related polynucleotide sequences. Under "stringent conditions" a sequence or fragments thereof will hybridize to the sequence's exact complement and closely related sequences.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription [Maniatis, T. et al., Science 236:1237 (1987)]. Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest. The term "promoter sequence" as used herein refers to a single promoter sequence as well as to a plurality (i.e., one or more) of promoter sequences which are operably linked to each other and to at least one DNA sequence of interest. For example, one of skill in the art knows that it may be desirable to use a double promoter sequence (i.e., a DNA sequence containing two promoter sequences) or a triple promoter sequence (i.e., a DNA sequence containing three promoter sequences) to control expression of a DNA sequence of interest. Double promoters are exemplified, but not limited to, vaRNA I-tRNA, vaRNA I-CMV, vaRNA I-RSV, vaRNA I-SV40, vaRNA I-PEPCK, vaRNA I-MT, vaRNA I-SRα, vaRNA I-P450 family, vaRNA I-GAL7, $T_7$-vaRNA I, $T_3$-vaRNA, vaRNA I-SP6, vaRNA I-K11, and vaRNA I-heat shock protein double promoters, while triple promoters are exemplified, but not limited to, the C(MV-$T_7$-vaRNA I triple promoter.

The presence of "splicing signals" on an expression vector often results in higher levels of expression of the recombinant transcript. Splicing signals mediate the removal of introns from the primary RNA transcript and consist of a splice donor and acceptor site [Sambrook, J. et al., *Molecular Cloning: A Laboratory Manual*, 2nd ed., Cold Spring Harbor Laboratory Press, New York (1989) pp. 16.7–16.8]. A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The terms "cognate promoter" and "cognate promoter of RNA polymerase" refer to a promoter sequence which is a naturally occurring promoter sequence in a gene encoding the RNA polymerase. For example, the cognate promoter of $T_7$ RNA polymerase is the promoter which is derived from the gene encoding RNA polymerase in $T_7$ bacteriophage. The cognate promoter sequence may be cloned from the genome encoding the RNA polymerase. The location of a promoter may be identified by approaches and methods well known in the art, including DNase foot printing of the RNA polymerase-bound genome DNA, mutational analysis, etc. Alternatively, where the sequence of a cognate promoter is know, the promoter sequence may be synthesized.

The term "transfection" as used herein refers to the introduction of a transgene into a cell. The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is not endogenous to the cell into which it is introduced. Heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell into which it is introduced and which contains some modification relative to the naturally-occurring sequence. Generally, although not necessarily, heterologous DNA encodes RNA and proteins that are not normally produced by the cell into which it is introduced. Examples of heterologous DNA include reporter genes, transcriptional and translational regulatory sequences, DNA sequences which encode selectable marker proteins (e.g., proteins which confer drug resistance), etc. Yet another example of a heterologous DNA includes a nucleotide sequence which encodes a ribozyme which is found in the cell into which it is introduced, and which is ligated to a promoter sequence to which it is not naturally ligated in that cell.

Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

The term "stable transfection" or "stably transfected" refers to the introduction and integration of a transgene into the genome of the transfected cell. The term "stable transfectant" refers to a cell which has stably integrated one or more transgenes into the genomic DNA.

The term "transient transfection" or "transiently transfected" refers to the introduction of one or more transgenes into a transfected cell in the absence of integration of the transgene into the host cell's genome. The term "transient transfectant" refers to a cell which has transiently integrated one or more transgenes.

A "transgenic organism" as used herein refers to an organism in which one or more cells has been transiently transfected or stably transfected with a transgene by experimental manipulation. Trangenic organisms may be produced by several methods including the introduction of a "transgene" comprising nucleic acid (usually DNA) into an embryonic target cell or a somatic target cell of a non-human organism by way of human intervention.

The term "gene" refers to a DNA sequence that comprises control and coding sequences necessary for the production of RNA or a polypeptide.

The terms "gene of interest" and "nucleotide sequence of interest" refer to any gene or nucleotide sequence respectively, the manipulation of which may be deemed desirable for any reason, by one of ordinary skill in the art.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of ribonucleotides along the RNA chain. The DNA sequence thus codes for the RNA sequence.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be denatured prior to or during transfer to the solid support. Southern blots are a standard tool of molecular biologists [J. Sambrook et al. (1989) *Molecular Cloning: A Laboratory Manual*, Cold Spring Harbor Press, N.Y., pp 9.31–9.58].

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists [J. Sambrook, J. et al. (1989) supra, pp 7.39–7.52].

The term "isolated" when used in relation to a nucleic acid, as in "an isolated oligonucleotide" refers to a nucleic acid sequence that is identified and separated from at least one component or contaminant with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. The isolated nucleic acid or oligonucleotide may be present in single-stranded or double-stranded form. When an isolated nucleic acid or oligonucleotide is to be utilized to express RNA, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein, the term "purified" or "to purify" refers to the removal of undesired components from a sample thereby increasing the percent of a desired component in the sample.

As used herein, the term "substantially purified" refers to molecules, whether nucleic or amino acid molecules, that are removed from their natural environment, isolated or separated, and are at least 60% free, preferably at least 75% free, and more preferably at least 90% free from other components with which they are naturally associated. An "isolated polynucleotide" is therefore a substantially purified polynucleotide.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products (e.g. transcription factors) which control the expression of other genes.

As used herein, the term "gene" means the deoxyribonucleotide sequences comprising the coding region of a structural gene and including sequences located adjacent to the coding region on both the 5' and 3' ends on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript: introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain enhancer sequences and other sequences which direct the termination of transcription, post-transcriptional cleavage and polyadenylation.

The term "ribozyme" refers to an RNA sequence that hybridizes to a complementary sequence in a substrate RNA and cleaves the substrate RNA in a sequence specific manner at a substrate cleavage site. Typically, a ribozyme contains a "catalytic region" flanked by two "binding regions." The ribozyme binding regions hybridize to the substrate RNA, while the catalytic region cleaves the substrate RNA at a "substrate cleavage site" to yield a "cleaved RNA product." The nucleotide sequence of the ribozyme binding regions may be completely complementary or partially complementary to the substrate RNA sequence with which the ribozyme binding regions hybridize. Complete complementarity is preferred in order to increase the specificity, as well as the turnover rate (i.e., the rate of release of the ribozyme from the cleaved RNA product), of the ribozyme. Partial complementarity, while less preferred, may be used to design a ribozyme binding region containing more than about 10 nucleotides. While contemplated to be within the scope of the claimed invention, partial complementarity is generally less preferred than complete complementarity since a binding region having partial complementarity to a substrate RNA exhibits reduced specificity and turnover rate of the ribozyme when compared to the specificity and turnover rate of a ribozyme which contains a binding region having complete complementarity to the substrate RNA. A ribozyme may hybridize to a partially or completely complementary DNA sequence but cannot cleave the hybridized DNA sequence since ribozyme cleavage requires a 2'—OH on the target molecule, which is not available on DNA sequences.

As used herein, "substrate RNA" refers to a ribonucleotide sequence with which a ribozyme is capable of hybridizing and cleaving. Substrate RNA includes, but is not limited to, messenger RNA (mRNA) (including, for example, eukaryotic mRNA and prokaryotic polycistronic mRNA), transfer RNA (tRNA) and ribosomal RNA (rRNA), heterogeneous nuclear (also known as pre-messenger) RNA (hnRNA), small nuclear RNA (snRNA), genomic RNA (e.g., in retroviruses), and chemically synthesized ribonucleotide sequences. RNA may be encoded by a complementary DNA template or RNA template.

The term "substrate cleavage site" and "substrate cleavage sequence" refer to a sequence in an RNA molecule at or near which a ribozyme cleaves the RNA molecule.

The terms "specific binding" or "specifically binding" when used in reference to the interaction of a ribozyme and a substrate RNA means that the interaction is dependent upon the presence of a particular sequence on the substrate RNA with which the binding regions of the ribozyme hybridize; in other words the ribozyme is recognizing and hybridizing with a specific nucleotide sequence rather than to nucleotides in general.

The term "endogenous ribozyme" refers to a ribozyme which is naturally found in the cell into which it is introduced so long as it does not contain some modification (e.g., deletion, insertion or substitution of a nucleotide, the presence of a ligated nucleotide sequence, etc.) relative to the naturally-occurring ribozyme. The term "heterologous ribozyme" refers to a ribozyme which is not endogenous to the cell into which it is introduced. Heterologous ribozyme includes a ribozyme which is ligated to, or is manipulated to become ligated to, a nucleotide sequence to which it is not ligated in nature, or to which it is ligated at a different location in nature. Heterologous ribozyme also includes a ribozyme which is naturally found in the cell into which it is introduced and which contains some modification relative to the naturally-occurring ribozyme.

As used herein, the term "oocyte" refers to a female gamete cell and includes primary oocytes, secondary oocytes, and mature, unfertilized ova. An oocyte is a large cell having a large nucleus (i.e., the germinal vesicle) surrounded by ooplasm. The ooplasm contains non-nuclear cytoplasmic contents including mRNA, ribosomes, mitochondria, yolk proteins, etc. The membrane of the oocyte is referred to herein as the "plasma membrane."

The term "transparent" when used herein in reference to a cell refers to the ability of the cell to transmit light such that organelles enclosed within the cell membrane may be visualized using visible light waves (e.g., by the naked eye or under a light microscope). A transparent cell includes a translucent cell (i.e., a cell which is capable of transmitting visible light and which causes sufficient diffusion of transmitted light to prevent visualization of distinct images), and is distinguished from an opaque cell (i.e., a cell which does not reflect visible light).

DESCRIPTION OF THE INVENTION

The present invention provides methods for the identification of one or more functions of a nucleotide sequence in an organism. In contrast to traditionally used "gene knockout" methods used for the determination of gene function in which the targeted gene is deleted or disrupted, the methods of the invention selectively destroy or diminish the RNA encoded by the targeted coding sequence in order to render the RNA non-functional while the targeted gene in the host remains intact. The methods disclosed herein thus employ a "knockdown" strategy rather than the commonly used "knockout" strategy. The invention is useful for the rapid identification of, for example, disease related genes which may be targeted for the treatment or prevention of disease.

In another embodiment, the invention discloses recombinant expression vectors which encode ribozyme sequences, as well as host cells and embryos comprising such expression vectors. The ribozyme sequences, recombinant expression vectors, host cells and embryos provided by the present invention are useful in identifying the function of any sequence of interest in an organism.

In yet another aspect, the invention provides transgenic organisms which express a ribozyme sequence that is capable of cleaving mRNA encoded by the nucleotide sequence whose function is sought to be determined. In one embodiment, the present invention provides transgenic zebrafish embryos and fry which transiently express one or more hammerhead ribozymes which specifically cleave mRNA encoded by the ntl gene which is responsible for notochord formation in zebrafish.

The methods of the invention are useful for the determination of the function of a DNA sequence in an organism by observing the effects of reducing expression of this DNA sequence in the organism or of a homologous DNA sequence in another organism. For example, data presented herein demonstrates that the function of the T gene in mouse may be determined by ribozyme cleavage of a transcript of the homologous ntl gene in zebrafish. The determination of function of a gene in one organism by reducing expression of a homologous gene in another organism is desirable, for example, where one organism is more readily available and easier to manipulate than the organism of interest. For example, as disclosed herein, fish (such as zebrafish) may be used as a model to determine the function of a homologous gene from mouse because (a) zebrafish can be inexpensively maintained in large numbers, (b) their fertilized eggs are larger and easier to microinject with a transgene than mouse fertilized eggs, (c) the zebrafish embryos are transparent thus allowing continued non-invasive observation of the effects of ribozyme, and (d) zebrafish reach full development within 96 hours of fertilization compared to several weeks for mouse (and longer for other organisms).

Alternatively, the function of a gene of interest in a first organism may be determined by reducing expression of a gene in a second organism using the methods of the invention where ethical considerations preclude experimentation on the first organism of interest. Thus, while ethical considerations preclude depleting, gene expression in humans in order to determine the function of that gene in a human individual, the ability to reduce expression of a gene sequence, which is homologous to the human gene sequence, in a model organism (e.g., fish, mouse, etc.) permits an initial determination of the function of the gene sequence in humans without resort to experimentation on human subjects. The function of the gene may then be further investigated in other model organisms and/or in clinical trials with human subjects.

The description of the invention is divided into descriptions of (A) Ribozymes. (B) Expression Vectors and Host Cells, and (C) Determination of Gene Function.

A. Ribozymes

The present invention provides methods for determining the function of any gene or sequence of interest in any organism. More specifically, the methods provided herein involve expression of a ribozyme sequence capable of reducing expression of the mRNA encoded by the sequence of interest, in combination with observation of the effect of such reduction of expression on the cell in which expression is reduced. In one embodiment, this is accomplished by introducing into an organism an expression vector which contains a sequence that encodes a hammerhead ribozyme which cleaves specifically the RNA encoded by the sequence of interest. In a preferred embodiment, the effect of reduction or ablation of RNA expression on the morphology of the host cell or host containing the expression vector is observed, thereby determining the function of the sequence of interest in the organism, or the function of a homologous sequence in another organism. These steps are further described below for specific embodiments.

i. Ribozyme type and structure

In one embodiment of the methods of the present invention for determining the function of a genomic DNA sequence, a ribozyme sequence is introduced into a cell in order to reduce the amount of RNA expressed by that genomic DNA sequence.

In a preferred embodiment, the ribozyme is a hammerhead ribozyme. The first hammerhead ribozyme was discovered in viroids (which are helper virus found in plants) and was found to cleave the polycistronic message RNA into individual RNA transcripts. The structure and design of hammerhead ribozymes is known in the art [see, e.g., Reddy et al., U.S. Pat. No. 5,246,921; Taira et al., U.S. Pat. No. 5,500,357; Goldberg et al., U.S. Pat. No. 5,225,347, the contents of each of which are herein incorporated by reference]. While the invention is not limited to a particular ribozyme, a hammerhead ribozyme was selected as one embodiment of the methods of the present invention since it requires the least constraints on the sequence of substrate RNA and is the best characterized ribozyme type with respect to optimized substrate cleavage site sequence, conserved nucleotide sequence, and the kinetic parameters [Sullivan (1994) J. Investig. Dermatol. 103:85S–89S].

Typically, a hammerhead ribozyme is composed of an RNA "catalytic region" which is flanked by two "binding regions." The ribozyme hybridizes to the substrate RNA via Watson-Crick base pairing between sequences on the substrate RNA and the binding regions of the ribozyme. This binding results in the orientation of the ribozyme's catalytic region within the substrate RNA in a manner such that the substrate RNA is cleaved at a "substrate cleavage site" by the catalytic region of the ribozyme. After cleavage of the substrate RNA, the cleavage products dissociate from the ribozyme, thus making the same ribozyme molecule available to hybridize to, and cleave, another substrate RNA sequence.

The catalytic region contains two "unpaired nucleotide sequences," a "stem structure" and a "loop." The term "unpaired nucleotide sequence" refers to a single-stranded sequence which flanks the stem structure of a ribozyme. Each of the unpaired nucleotide sequences flanking the stem structure contains several conserved sequences. On the 5'-end of the stem the conserved sequence is 5'-CUGANGA-3', while on the 3'-end of the stem, the conserved sequence is 5'-GAAA-3', where N can be any nucleotide (Xing et al. (1992) J. Virol. 66:1361–1369) and frequently is a U. Any mutation in those conserved sequences abolishes the ribozyme activity. For example, a mutant ribozyme with a A→G mutation in the 3' region is known to abolish cleavage activity completely in vitro (Puttaraju et al. (1993) Nucleic Acid Res. 21: 4253–4258) and in vivo (Steinecke et al. (1992) EMBO J. 11:1525–1530) and is commonly used as a negative control (Lieber and Strauss (1995) Mal. Cell. Biol. 15(1): 540–551).

In a preferred embodiment, the sequence of the unpaired nucleotide sequence of the ribozyme on the 5'-end of the stem is 5'-CUGAUGA-3'. Also in a preferred embodiment the sequence of the unpaired nucleotide sequence of the ribozyme on the 3'-end of the stem is 5'-GAAA-3'. However, the ribozymes of the invention are not limited to ribozymes which contain an unpaired nucleotide sequence of the sequence 5'-CUGAUGA-3' located at the 5'-end of the stem, and/or an unpaired nucleotide sequence of the sequence 5'-GAAA-3' located at the 3'-end of the stem. Rather, unpaired nucleotide sequences of any length and any sequence are contemplated to be within the scope of this invention so long as the ribozyme is capable of cleaving at a substrate cleavage site. The ability of a ribozyme to cleave at a substrate cleavage site may readily be determined using methods known in the art. These methods include, but are not limited to, the detection (e.g., by Northern blot analysis as described herein, reverse-transcription polymerase chain reaction (RT-PCR), in situ hybridization and the like) of reduced in vitro or in vivo levels of RNA which contains a ribozyme substrate cleavage site for which the ribozyme is specific, compared to the level of RNA in controls (e.g., in the absence of ribozyme, or in the presence of a ribozyme sequence which contains a mutation in one or both unpaired nucleotide sequences which renders the ribozyme incapable of cleaving a substrate RNA).

The term "stem structure" refers to a double-stranded nucleotide sequence which is flanked by unpaired nucleotide sequences and in which the nucleotides of each strand are hybridized in accordance with the base-pairing rules. In a preferred embodiment the stem is a four-pair stem with a high GC content. In yet a more preferred embodiment, the sequence of the double-stranded stem is:

5'-GUCC-3'
3'-CAGG-5'

The invention is not limited to ribozymes which contain four-pair stems. Stem structures of any length and any sequence are contemplated to be within the scope of this invention so long as the ribozyme is capable of cleaving at a substrate cleavage site.

The stem is contiguous (i.e. ligated directly) to a "loop" of a single-stranded nucleotide sequence. In a preferred embodiment, the loop consists of a tetra-nucleotide sequence having the sequence 5'-GUGA-3'. A loop of any sequence and of any length is included within the scope of the invention so long as the ribozyme in which the loop is contained is capable of cleaving at a substrate cleavage site.

The mechanism of cleavage by a hammerhead ribozyme has been characterized in the art [Sullivan (1994), supra]. While an understanding of the precise mechanism of the invention is not necessary, it is believed that the ribozyme is attached to the substrate RNA molecule by forming two paired regions vica Watson-Crick pairing between the RNA substrate sequence and the two binding regions of the ribozyme. The first deprotonation reaction takes place in the 2' sugar at the 3' side of the substrate cleavage site. This deprotonation causes nucleophilic attack of the adjacent phosphodiester bond and subsequently protonation of the 5 oxyanion cleaving group thereby generating, 2',3'-cyclic phosphate and a 5' hydroxyl terminus. Thus the 2' hydroxyl of the nucleotide adjacent to the substrate cleavage site in the substrate RNA is required for cleavage. The ribozyme is then released from the cleaved products and reused to attack another substrate. Kinetic studies have shown that the length and nucleotide composition of the binding regions play very important roles by controlling the rates of hybridization of the ribozyme to the RNA substrate, dissociation of the ribozyme from the substrate, as well as dissociation of the ribozyme from the cleaved products. It is within the skill of the art to determine an optimum nucleotide composition and length of the binding regions of a ribozyme to achieve desired rates of hybridization and dissociation.

The methods of the invention are not limited to hammerhead ribozymes. Any ribozyme is contemplated to be within the scope of the invention so long as it is capable of cleaving a substrate RNA. Ribozymes contemplated to be within the scope of this invention include, but are not restricted to, Group I intron ribozyme, ribonuclease P, hairpin ribozyme and hepatitis delta virus ribozyme.

Group I intron ribozyme was the first known ribozyme which was described by Dr. Cech and colleagues in tetrahymena in 1982 (Kruger et al. (1992) Cell 31: 147–157). This ribozyme was found to be involved in the processing of ribosomal RNA (rRNA) through a unique self-splicing manner. The self-splicing of rRNA occurs by a two step mechanism. First, a guanine nucleotide is added to the 5' end of the intron as the introyexon junction is being cleaved. Then the freed 5' intron with guanine attacks at the 3' introyexon junction to release the intron and generate spliced exons [Zaug et al. (1986) Nature 324:429–433]

Ribonuclease P contains a catalytic RNA and a small subunit protein. It was discovered in bacteria and is able to generate a mature 5' end of tRNA by endonucleocatalytic cleavage of precursor transcripts (Guerrier-Takada et al. (1983) Cell 35: 849–857).

Hairpin ribozyme was also found in plant viroids, and it plays a role similar to that of hammerhead ribozyme (Feldstein et al. (1989) Gene 82:53–61). The design and use of hairpin ribozymes for cleaving an RNA substrate has been described in the art [Hampel et al., U.S. Pat. No. 5,527,895 incorporated by reference].

Hepatitis delta virus ribozyme was discovered by Dr. Wu and colleagues in 1989 [Wu et al. (1989) Science 243:652–655], who found that the RNA of the hepatitis delta virus has autocatalytic RNA processing activity similar to that of hammerhead and hairpin ribozyme, and defined the ribozyme cleavage points of both delta strands and the domains containing them.

ii. Design and selection of ribozyme

A ribozyme may be designed to cleave at a substrate cleavage site in any substrate RNA so long as the substrate RNA contains one or more substrate cleavage sequences, and the sequences flanking the substrate cleavage site are known. Expression in vivo of such ribozymes and the resulting cleavage of RNA transcripts of a gene of interest would in effect reduce or ablate expression of the corresponding gene.

For example, where the ribozyme is a hammerhead ribozyme, the basic principle of a hammerhead ribozyme design involves selection of a region in the substrate RNA which contains a substrate cleavage sequence, creation of two stretches of antisense oligonucleotides (i.e., the binding regions) which hybridize to sequences flanking the substrate cleavage sequence, and placing a sequence which forms a hammerhead catalytic region between the two binding regions.

In order to select a region in the substrate RNA which contains candidate substrate cleavage sites, the sequence of the substrate RNA needs to be determined. The sequence of the RNA encoded by a genomic sequence of interest is readily determined using methods known in the art. For example, the sequence of an RNA transcript may be arrived at either manually, or using available computer programs (e.g., CENEWORKS, from IntelliGenctic Inc., or RNADRAW available from the internet at ole@mango.mef.ki.se), by changing the T in the DNA sequence encoding the RNA transcript to a U. Since mRNA is transcribed from the antisense strand DNA of a gene, its sequence is exactly the same as the sense strand of the gene sequence except that there is a U in the mRNA at the position of a T in the sense strand of the gene. When a DNA sequence is input into the RNADRAW program, the program automatically switches all T's to U's. The DNA sequence may be determined using art-known methods which employ such enzymes as the Klenow fragment of DNA polymerase I, Sequenase® (US Biochemical Corp, Cleveland Ohio), Tacq DNA polymerase (Perkin Elmer, Norwalk Conn.), thermostable $T_7$ polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Having determined the RNA sequence, substrate cleavage sequences may by located by searching the RNA sequence for substrate cleavage sequences using available computer programs. For example, where the ribozyme is a hammerhead ribozyme, it is known in the art that the catalytic region of the hammerhead ribozyme cleaves only at a substrate cleavage site which contains a NUH, where N is any nucleotide. U is a uridine, and H is a cytosine (C), uridine (U), or adenine (A) but not a guanine (G). The U—H doublet in the NUH cleavage site does not include a U—G doublet since a G would pair with the adjacent C in the ribozyme and prevent ribozyme cleavage. Typically, N is a G and H is a C. Consequently, GUC has been found to be the most efficient substrate cleavage site for hammerhead ribozymes, although ribozyme cleavage at CUC is also efficient.

In a preferred embodiment, the substrate cleavage sequence is located in a loop structure or in an unpaired region of the substrate RNA. The term "loop structure" refers to a secondary structure in an RNA sequence in which a single-stranded RNA sequence is flanked by RNA sequences which are capable of pairing with each other to form a "stem" structure. The term "unpaired region" when made in reference to RNA refers to a secondary structure in an RNA sequence in which RNA is single-stranded and is flanked by RNA sequences which are incapable of pairing with each other, but which are capable of pairing with other sequences. Without intending to limit the invention to any particular mechanism, loop structures and unpaired regions are preferred locations for substrate cleavage sequences because it is the inventors' consideration that these regions make substrate cleavage sequences on an RNA substrate more accessible than if such substrate cleavage sequences were embedded within the double-stranded RNA secondary structure. Computer programs for the prediction of RNA secondary structure formation are known in the art and include, for example, "RNADRAW" which may be unloaded from the InterNet at ole@mango.mef.ki.se, "RNAFOLD" [described in Hofacker et al. (1994) Monatshefte F. Chemie 125:167–188; McCaskill (1990) Biopolymers 29:1105–1119]. "DNASIS" (Hitachi), and The Vienna Package obtainable from the InterNet at ftp://nrcbsa.bio.nrc.ca/pub and ftp://ftp.itc.univie.ac.at. In yet a further preferred embodiment, the substrate cleavage sequence is located in a loop of between about 7 nucleotides and about 9 nucleotides, more preferably of between about 10 nucleotides and about 12 nucleotide, and most preferably of between about 13 nucleotides and about 15 nucleotides. Data presented herein demonstrates that a ribozyme sequence which cleaves at a substrate cleavage sequence located in a 12-nucleotide (12-nt) loop results in a greater reduction in RNA expression than a ribozyme sequence which cleaves at a substrate cleavage sequence located in a 9-nt loop. Similarly, data disclosed herein also demonstrates that a ribozyme which cleaves at a substrate cleavage sequence located in a 14-nt loop results in a greater reduction in RNA expression than a ribozyme which targets a substrate cleavage sequence located in a 12-nt loop.

The invention is not limited to substrate cleavage sequences located in unpaired regions or loop structure, or to the number of ribonucleotide in these regions and structures. Cleavage sequences of any length may be located anywhere in a substrate RNA so long as a ribozyme is capable of cleaving at or near the substrate cleavage site.

Alternative strategies for determining accessible substrate cleavage sequences and for producing ribozymes which are capable of cleaving these sequences in vivo are known in the art. For example, Lieber and Strauss used a strategy of randomly mutating a ribozyme library in combination with transfecting cell lines as well as creating gene-specific primers to locate accessible substrate cleavage sites on human growth hormone RNA [Lieber and Strauss (1995) Molec. Cell. Biol. 15:540–5511. Briefly, a ribozyme catalytic sequence is designed and a pool of randomly mutated ribozyme genes is synthesized by randomly selecting a number of nucleotides (e.g., 11-nt and 13-nt) as the two binding regions which flank this unique hammerhead structure. A ribozyme expression library containing plasmid clones with different sequences is then established by cloning the randomly mutated ribozyme genes into an expression vector and transforming bacteria (e.g., E. coli). To test for the overall ribozyme activity of this library, the total ribozyme plasmid library is transcribed in vitro, and the transcripts (i.e., ribozymes) are incubated with either total-cell RNA or a cytoplasmic RNA-protein fraction isolated from a cell which expresses the gene whose expression is sought to be reduced by the ribozymes. RNAs from various incubations are analyzed by the technique of rapid amplification of cDNA ends (RACE). RACE involves purification of the 3'-end of mRNA fragments by using an oligo(dT) column and reverse transcription with oligo(dT) as a primer. The 5'-end of cDNA is tailed with dG and then double-stranded cDNA is generated by using oligo(dC) as a primer. The cDNA pool is then amplified with oligo(dC) primer and a downstream primer which is specific for the gene whose expression is sought to be reduced by the ribozymes. The amplified cDNA is separated by gel electrophoresis. The observation of DNA gel bands from cDNA recovered from incubation of ribozyme library with total cell RNA shows the presence of accessible substrate cleavage sites on the target gene's nuclear RNA or mRNA in the incubation system. The absence of these bands in incubations of ribozyme library with the cytoplasmic RNA-protein preparation shows that the absent bands are inaccessible for ribozyme cleavage. The next step involves isolating the ribozymes in the library which have produced a particular fragment. This can be achieved by PCR amplification using the sequence flanking that fragment as two primers. The term "polymerase chain reaction" ("PCR") refers to the method of K. B. Mullis, U.S. Pat. Nos. 4,683,195 and 4,683,202, hereby incorporated by reference. PCR methods are well known in the art [Dieffenbach and Dveksler (1995) PCR Primer, a Laboratory Manual, Cold Spring Harbor Press, Plainview, N.Y.].

In addition to the desirability of selecting substrate cleavage sequences which are located in a loop structure or an unpaired region of the substrate RNA, it is also desirable, though not required, that the substrate cleavage sequence be located downstream (i.e., at the 3'-end) of the translation start codon (AUG or GUG) such that the translated truncated polypeptide is not be biologically functional.

Having selected a substrate cleavage sequence on the substrate RNA, a ribozyme can be engineered that base pairs with the RNA substrate and mediates a cleavage at the substrate cleavage sequence. In other words, a ribozyme can be engineered that will cleave any RNA substrate having a substrate cleavage sequence. This can be achieved by determining the sequence of the regions flanking the substrate cleavage sequence, and engineering the ribozyme such that it does not base-pair with the substrate cleavage sequence but does base-pair with a sufficient number of flanking bases upstream and downstream of the substrate cleavage sequence in order to optimize specificity.

It is known in the art that the specificity of ribozyme cleavage for a substrate RNA molecule is determined by the sequence of nucleotides which flank the substrate cleavage site and which hybridize with the ribozyme binding regions. Thus, ribozymes can be designed to cleave at different locations within a substrate RNA molecule by altering the sequence of the binding regions that surround the ribozyme catalytic region of the ribozyme such that the binding regions hybridize with any known sequence on the substrate RNA.

In addition to varying the sequence of the binding regions to effect binding to different locations on the RNA substrate, the number of nucleotides in each of the ribozyme binding regions may also be altered in order to change the specificity of the ribozyme for a given location on the RNA substrate. The number of nucleotides in a binding region is preferably between about 25 and about 25 nucleotides, more preferably between about 11 and about 15 nucleotides, yet more preferably between about 7 nucleotides and about 10 nucleotides.

In one embodiment, each binding region contains 8 nucleotides. However, the length of the binding region is not limited to 8 nucleotides. Additionally, it is not necessary that the two binding regions which flank the ribozyme catalytic region be of equal length. Binding regions which contain any number of nucleotides are contemplated to be within the scope of this invention so long as the desirable specificity of the ribozyme for the RNA substrate and the desirable cleavage rate of the RNA substrate are achieved. One of skill in the art knows that binding regions of longer nucleotide sequence, while increasing the specificity for a particular substrate RNA sequence, may reduce the ability of the ribozyme to dissociate from the substrate RNA following cleavage to bind with another substrate RNA molecule, thus reducing the rate of cleavage. On the other hand, though binding regions with shorter nucleotide sequences may have a higher rate of dissociation and cleavage, specificity for a substrate cleavage site may be compromised.

It is well within the skill of the art to determine an optimal length for the binding regions of a ribozyme such that a desirable specificity and rate of cleavage are achieved. Both the specificity of a ribozyme for a substrate RNA and the rate of cleavage of a substrate RNA by a ribozyme may be determined by, for example, kinetic studies in combination with Northern blot analysis or nuclease protection assays.

In a preferred embodiment, the complementarity between the ribozyme binding regions and the substrate RNA is complete. However, the invention is not limited to ribozyme sequences in which the binding regions show complete complementarity with the substrate RNA. Complementarity may be partial so long as the desired specificity of the ribozyme for a substrate cleavage site, and the rate of cleavage of the substrate RNA are achieved. Thus, base changes may be made in one or both of the ribozyme binding regions as long as substantial base pairing with the substrate RNA in the regions flanking the substrate cleavage sequence is maintained and base pairing with the substrate cleavage sequence is minimized. The term "substantial base pairing" means that greater than about 65%, more preferably greater than about 75%, and yet more preferably greater than about 90% of the bases of the hybridized sequences are base-paired.

iii. Nuclease stability of the ribozyme

Ribozymes are RNA molecules and are therefore susceptible to degradative ribonucleases. The half-life time ($t_{1/2}$) of some ribozymes is less than 1 minute in serum. It is desirable to increase a ribozymes' ribonuclease resistance in order to increase the $t_{1/2}$ as well as the rate of accumulation of ribozyme within the cell, thereby decreasing the required dose level of ribozyme.

In a preferred embodiment, the intracellular stability of ribozymes expressed by an expression vector may be increased by designing the expressed ribozyme such that it contains a secondary structure within the ribozyme molecule. Secondary structures which are suitable for stabilizing ribozymes include, but are not limited to, stem-loop structures formed by intrastrand base pairs. In one embodiment, the ribozymes of the present invention are stabilized against ribonuclease attack by designing the ribozyme sequence to reside in a loop structure which is flanked by sequences which hybridize to each other to form a stem structure (FIG. 5B).

Yet another example of the use of a stem-loop structure to protect ribozymes against ribonuclease degradation is by the insertion of a stem loop at each end of the ribozyme sequence. Such methods are known in the art. For example, a ribozyme containing a stem loop at each end of the ribozyme sequence has been shown to reduce the rate of degradation of the ribozyme [Sioud and Drlica (1991) Proc. Natl. Acad. Sci. USA 88:7303–7307]. The effect of a secondary structure on the rate of ribozyme degradation by ribonucleases may be determined by comparing the levels of reduced expression of the substrate RNA in the presence of the unmodified ribozyme and the ribozyme modified with the secondary structure. A greater reduction in the level of substrate RNA expression in the presence of the modified ribozyme as compared to the level of substrate RNA expression in the presence of the unmodified ribozyme indicates that the secondary structure is effective in increasing the ribozyme's resistance to ribonuclease degradation.

The invention is not limited to the use of stem-loop structures for the stabilization of ribozymes expressed by expression vectors. Other secondary structures which are useful in reducing the susceptibility of a ribozyme to ribonuclease degradation include hairpin, bulge loop, interior loop, multibranched loop, and pseudoknot structure as described in "Molecular and Cellular Biology," Stephen L. Wolfe (Ed.), Wadsworth Publishing Company (1993) p. 575.

Another strategy of expressing ribozymes which are resistant to ribonuclease degradation is to circularize the ribozyme molecule. Circularization protects against ribonuclease degradation since exonuclease degradation is initiated at either the 5'-end or 3'-end of the RNA. Methods of expressing a circularized RNA are known in the art [see, e.g., Puttaraju et al. (1993) Nucl. Acids Res. 21:4253–4258].

Once a ribozyme with desirable binding regions, a catalytic region and nuclease stability has been designed, the ribozyme may be produced by any known means including chemical synthesis. Chemically synthesized ribozymes may be introduced into a cell by, for example, microinjection electroporation, lipofection, etc. In a preferred embodiment, ribozymes are produced by expression from an expression vector which contains a gene encoding the designed ribozyme sequence, as described in the following sections.

B. Expression Vectors and Host Cells

In order to express a ribozyme, a nucleotide sequence encoding the ribozyme is inserted into an appropriate expression vector, i.e., a vector which contains the necessary elements for the transcription of the inserted coding sequence. The expression vector is then transfected into a host cell in order to effectuate expression of the ribozyme-encoding sequence and to determine the effect of ribozyme on expression of the substrate RNA and on gene function in the transfected cell and/or its progeny.

Methods which are well known to those skilled in the art can be used to construct expression vectors containing a sequence which encodes a ribozyme and appropriate transcriptional controls. These methods include in vitro recombinant DNA techniques, synthetic techniques and in vivo recombination or genetic recombination. Such techniques are described in Sambrook et al. (1989) *Molecular Cloning, A Laboratory Manual*, Cold Spring Harbor Press, Plainview N.Y. and Ausubel F M et al. (1989) *Current Protocols in Molecular Biology*, John Wiley & Sons, New York N.Y.

i. Promoters

It is desirable to express a sufficient amount of ribozyme such that substantially all the substrate RNA is cleaved. Such substantial abrogation of substrate RNA expression would facilitate the observation of the effect of depletion of gene function in the organism wherein the ribozyme is expressed. While desirable, complete elimination of the substrate RNA is not required by the methods ol the invention. Any level of ribozyme expression is deemed to be within the scope of the methods disclosed herein, so long as the expressed ribozyme results in a reduced level of substrate RNA relative to a control. The term "reduced level of substrate RNA relative to a control" refers to a quantity of substrate RNA which is less than, preferably at least 10% less than, more preferably at least 50% less than, yet more preferably at least 90% less than the quantity of substrate RNA in a control (i.e., a corresponding sample in the absence of ribozyme, or in the presence of an RNA sequence which is incapable of cleaving at or near the substrate cleavage site), and most preferably is at the background level of, or is undetectable by, Northern blot hybridization as described herein. When a background level or undetectable level of substrate RNA is measured, this may indicate that the substrate RNA is cleaved. A "reduced level of substrate RNA" need not, although it may, mean an absolute absence of substrate RNA. The invention does not require, and is not limited to, methods in which substrate RNA is 100% ablated.

As demonstrated herein, partial reduction in expression of zebrafish ntl RNA by a ribozyme was sufficient for the determination of a function for the zebrafish ntl DNA sequence, Ribozyme$_{435}$, Ribozyme$_{365}$ and Ribozyme$_{564}$ which reduced ntl RNA expression compared to controls in the absence of ribozyme resulted in partial no tail mutant zebrafish, thus confirming a role for the zebrafish ntl DNA in tail formation.

Ribozyme expression levels may be controlled in various ways in order to achieve a desirable ribozyme expression level. For example, where ribozyme gene expression is designed such that the ribozyme gene is transcribed by the same RNA polymerase (e.g, RNA polymerase II) as the substrate RNA, ribozyme expression levels which are greater than the expression levels of the substrate RNA may be achieved by engineering the ribozyme gene (i.e., a DNA sequence encoding a ribozyme) such that it is driven by a promoter which is stronger (i.e., which directs expression of a greater number of transcripts in a given time) than that which drives the expression of the substrate RNA. In one embodiment, the promoter is a RNA polymerase III promoter derived from the adenovirus type 2-associated RNA I (vaRNA I) gene and is an internal (i.e., intragenic) promoter contained inside the vaRNA I gene at positions +10 to +16 and +58 to +68 of the vaRNA I gene which has the sequence (SEQ ID NO:]):
5' -GGCACTCTTCCGTGGTCTGGTGGATAAATTCGCA AGGGTATCATGGCGG ACGACCGGGGTTCGAAC- CCCGGATCGGCCGTCCGCCGTGATCCATGCGGTT ACCGCCCGCGTGTCGAACCCAGGTGTGC- GACGTCAGACAACGGGGGAGCGCT CCTTTT-3'

The invention is not limited to the vaRNA I gene promoter. Other promoters which are included within the scope of the invention include, but are not limited to, tRNA promoter, 5S rRNA promoters, histone gene promoters, CMV promoter (located between positions +1 to +596 in vector plasmid pCR3 from Invitrogen), RSV promoter (can be isolated from vector plasmid pRc/RSV from Invitrogen), SV40 promoter (located between positions +3530 to +3192 in vector plasmid pCR3 from Invitrogen), PEPCK promoter, MT promoter, SRα promoter, P450 family promoters, GAL7 promoter, $T_7$ promoter having the 23-bp sequence (SEQ ID NO:2) 5'-TAATACGACTCACTATAGGGCGA-3'), $T_3$ promoter having the 24-bp sequence (SEQ ID NO:3) 5'-TTATTAACCCTCACTAAAGGGAAG-3', SP6 promoter having the 23-bp sequence (SEQ ID NO:4) 5'-ATTTAGGTGACACTATAGAATAC-3', and K11 promoter. The T7 promoter, $T_3$ promoter, SP6 promoter and $K_{11}$ promoter have been described in U.S. Pat. No. 5,591,601, the entire contents of which are incorporated by reference.

Alternatively, ribozyme expression levels which are sufficient to reduce the level of substrate RNA may be achieved by expressing multiple ribozyme genes which encode ribozymes that cleave at the same, or different, locations in the substrate RNA under the control of a single promoter. As exemplified herein, each ribozyme gene may be individually expressed under the control of a promoter on a separate expression vector. In the alternative, ribozyme genes ligated in tandem may be operably linked to a promoter sequence on a single expression vector.

Yet another alternative to expressing sufficient levels of ribozyme to reduce the level of substrate RNA is by expression of the ribozyme gene under the control of a double promoter. In a preferred embodiment, the double promoter is a $T_7$ promoter and a vaRNA I promoter. However, the invention is not restricted to a $T_7$-vaRNA I double promoter. Any double promoter which expresses ribozyme levels which are sufficient to reduce the level of a substrate RNA are contemplated to be within the scope of this invention. Such double promoters are exemplified by, but not limited to, vaRNA I-RSV double promoter and vaRNA I-CMV double promoter. The vaRNA I-CMV double promoter is particularly preferred since the CMV promoter is one of the strongest promoters in zebrafish. Other double promoters which are contemplated to fall within the scope of this invention include double promoters in which at least one of the promoters is inducible, e.g., vaRNA I-MT double promoter, vaRNA I-heat shock protein double promoter, and vaRNA I-P450 family double promoters. Double promoters containing at least one inducible promoter may be desirable where regulation of ribozyme expression is advantageous. For example, ribozyme expression under the control of a vaRNA I-MT double promoter may be regulated by changing the concentration of heavy metal ions in the incubation solution, while ribozyme expression under the control of a vaRNA I-heat shock protein double promoter may be regulated by changing the incubation temperature.

In a yet another alternative, sufficiently high levels of ribozyme may be expressed under the control of a triple promoter. In a preferred embodiment, the triple promoter is a CMV-$T_7$-vaRNA I promoter and has the following configuration from the 5'- to the 3'-end of the construct: $P_{CMV}$-$P_{T7}$-$P_{vaRNAI}$-Ribozyme gene-$T_{vaRNAI}$-$T_7$-bGH poly(A), where P is a promoter, T is a transcription termination signal, and bGH poly(A) is the transcription termination signal for the CMV promoter. One of the advantages of this triple promoter is that it is capable of utilizing three different RNA polymerases, thus increasing the expression level of the transcribed ribozyme: the CMV promoter is a RNA polymerase II promoter which is recognized and transcribed by endogenous RNA polymerase II and which has been shown to exhibit very strong promoter activity in zebrafish; the $T_7$ promoter is recognized and transcribed by introduced $T_7$ RNA polymerase; and the vaRNA I promoter is recognized and transcribed by the endogenous RNA polymerase III.

A further method for expressing ribozyme levels which are sufficient to reduce substrate RNA levels is by inclusion of enhancer sequences in the expression vector. Enhancer sequences are cis-acting regulatory sequences involved in the transcription activation of eukaryotic genes. Enhancers can operate when located either 5' or 3' to the transcription start site, can function in either orientation, and can operate even when placed at a distance of greater than 3 kb from the transcription start site. Enhancer sequences are known in the art, as exemplified by the SV40 viral enhancer, histone gene enhancer, hemoglobin gene enhancer and U snRNA gene enhancer.

Promoters contemplated to be within the scope of the invention include "cytoplasmic promoters" and "nuclear promoters." A "cytoplasmic promoter" as used herein refers to a promoter which is recognizable by an RNA polymerase that is located in the cytoplasm. It is believed in the art that plasmid DNA introduced into the cytoplasm migrates into the nucleus over time. Thus, in order to prolong expression of a ribozyme gene, it is preferred, though not necessary, that the double and triple promoters of the invention comprise a combination of cytoplasmic and nuclear promoters. Cytoplasmic promoters are exemplified by the $T_7$ promoter (described herein) and the SP6 promoter. The term "nuclear promoter" as used herein refers to a promoter which is recognizable by an RNA polymerase that is located in the nucleus. Examples of nuclear promoters include the va RNA I promoter (described herein) and the promoters for RNA polymerases I, II, and III. The activity of cytoplasmic and nuclear promoters may be determined using methods known in the art, e.g., Northern blot analysis. Data presented herein shows that ribozymes which were expressed under the control of either the nuclear vaRNA I promoter alone, or the $T_7$/vaRNA I double-promoter resulted in a reduced expression of the target ntl mRNA as well as in a phenotypic alteration in the progeny which expressed the ribozymes.

ii. Introduction of vectors into host cells

Once a ribozyme expression vector is constructed, it may be introduced into a host cell to effectively express the ribozyme gene. In a preferred embodiment, a plasmid containing a ribozyme gene under the control of a $T_7$/vaRNA double promoter is transiently expressed by microinjection into a zebrafish fertilized egg cell. The expression of ribozyme gene in the zebrafish fertilized egg cell is transcriptionally controlled by both the $T_7$ and va RNA I promoters (when co-injected with $T_7T_7$ plasmid which can supply $T_7$ RNA polymerase) or by the vaRNA I promoter alone (without the co-injection of $T_7T_7$ plasmid).

Introduction of an expression vector into a host cell is not limited to microinjection. Any of a number of standard and routine methods known to those skilled in the art may be used to transfect an expression vector into the desired cell [see, e.g., Sambrook, et al., *Molecular Cloning A Laboratory Manual*, 2nd ed., Cold Spring Harbor Laboratory Press, N.Y. Cold Spring Harbor Laboratory (1989)]. For example, expression vectors may be introduced by DEAE-dextran, calcium phosphate co-precipitation, cell fusion, electroporation, biolistics, lipofection, DNA viruses, and RNA viruses, or retrovirus-mediated transduction.

Where the host cell is a plant cell, expression vectors may be introduced by particle mediated gene transfer. Particle mediated gene transfer methods are known in the art, are commercially available, and include, but are not limited to, the gas driven gene delivery instrument described in McCabe, U.S. Pat. No. 5,584,807, incorporated by reference. Alternatively, an expression construct may be inserted into the genome of plant cells by infecting plant cells with a bacterium, including but not limited to an Agrobctcterizim strain previously transformed with the expression vector which contains the ribozyme gene. Generally, disarmed Agrobacterium cells are transformed with recombinant Ti plasmids of *Agrobacterium tumefaciens* or Ri plasmids of *Agrobacterium rhizogenes* (such as those described in U.S. Pat. No. 4,940,838, herein incorporated by reference) which are constructed to contain the nucleic acid sequence of interest using methods well known in the art (Sambrook, J. et al., (1989) supra). The nucleic acid sequence of interest is then transiently or stably transfected into the plant genome by infection with the transformed Agrobacterium strain. For example, heterologous nucleic acid sequences have been introduced into plant tissues using the natural DNA transfer system of *Agrobacterium tumefaciens* and *Agrobacterium rhizogenes* bacteria (for review, see Klee et al. (1987) Ann. Rev. Plant Phys. 38:467–486). The efficiency of transformation by Agrobacterium may be enhanced by, for example, the inclusion of a natural wound response molecule such as acetosyringone (AS) to the Agrobacterium culture. Alternatively, transformation efficiency may be enhanced by wounding the target tissue to be transformed. Wounding of plant tissue may be achieved, for example, by punching, maceration, bombardment with microprojectiles, etc.

Other methods are also available for the introduction of expression constructs into plant tissue, e.g., electroinjection (Nan et al. (1995) In "Biotechnology in Agriculture and Forestry," Ed. Y. P. S. Bajaj, Springer-Verlag Berlin Heidelberg, Vol 34:145–155: Griesbach (1992) HortScience 27:620); fusion with liposomes, lysosomes, cells, minicells or other fusible lipid-surfaced bodies (Fraley et al. (1982) Proc. Natl. Acad. Sci. USA 79:1859–1863; polyethylene glycol (Krens et al. (1982) nature 296:72–74); chemicals that increase force DNA uptake; transformation using virus, and the like.

Transfection is not limited to the use of plasmids as vectors. Other expression vectors contemplated to be within the scope of the invention include, but are not limited to, recombinant bacteriophage, cosmid DNA expression vectors, yeast expression vectors, virus expression vectors and the like.

iii. Transient and stable expression

In one embodiment of the invention, the expression vectors are introduced into a host cell to bring about transient ribozyme expression. When transient expression cells are to be employed, expression vectors may be introduced into the host cell using any of the above-described techniques (i.e., DEAE-dextran mediated transfection. calcium phosphate-DNA co-precipitation, electroporation, lipofection, liposome fusion, protoplast fusion, microinjection, etc.)

The methods of the present invention are not limited to the use of transiently transfected cells. Stably transfected cells are included within the scope of this invention. When stably transfected cells are employed, expression vectors may be introduced into the recipient cell using any suitable technique (as described above). The expression vector which contains the ribozyme-encoding sequence may also contain a selectable marker gene. Alternatively, a second vector encoding a selectable marker may be co-transfected with the expression vector encoding the ribozyme into the recipient cell. Following the introduction of the DNA sequences, the cells are grown in medium which requires the recipient cells to express the selectable marker. Cells which express the selectable marker after a number of cell division cycles are stably transfected.

Where stably transfected cells are capable of generating a multicellular organism, stably transfected multicellular transgenic organisms may be generated using methods known in the art. For example, where the stably transfected cell is an embryonic stem (ES) cell of an animal, several ES cells may be introduced into the blastocoel cavity of intact blastocysts, or alternatively sandwiched between two eight-cell embryos, before introduction into a pseudopregnant female for further development into an animal. Similarly, where a stably transfected zygote is used to generate a stably transfected multicellular animal, the zygote may be introduced into a recipient pseudo-pregnant female to permit development of an animal. Likewise, a stably transfected oocyte or sperm cell may be used to generate a stably transfected transgenic animal following fertilization and introduction of the fertilized oocyte into a recipient female for gestation and delivery of an animal.

Where stably transfected callous and protocorm-like bodies are selected, these structures may be used to generate stably transfected transgenic plants by growth in appropriate media in the presence of growth regulators using methods known in the art.

iv. Host cells

In one embodiment of the methods of the invention, zebrafish fertilized eggs which are transiently transfected with expression vectors that express ribozyme sequences are used to determine the function of DNA sequences in zebrafish and in mammals, such as humans and rodents.

The invention is, however, not limited to the type of organism or type of cell in which ribozyme is expressed. Any organism in which the function of a DNA sequence is sought to be determined is contemplated to be within the scope of the invention. Such organisms include, but are not restricted to, animals (e.g., vertebrates, invertebrates, etc.), plants (e.g., monocotyledon, dicotyledon, vascular, non-vascular, seedless, seed plants, etc.), protists (e.g., algae, citliates, diatoms, etc.), fungi (including multicellular forms and the single-celled yeasts), bacteria (prokaryotic, eukaryotic, archaebacteria, etc.), and viruses.

In addition, any type of cell into which an expression vector may be introduced is expressly included within the scope of this invention. Such cells are exemplified by embryonic cells (e.g., oocytes, sperm cells, embryonic stem cells, 2-cell embryos, protocorm-like body cells, callous cells, etc.), adult cells (e.g., brain cells, fruit cells etc.), undifferentiated cells (e.g., fetal cells, tumor cells, etc.), differentiated cells (e.g., skin cells, liver cell, etc.), dividing cells, senescing cells, cultured cells, and the like.

In a preferred embodiment, the cell is a zebrafish fertilized egg cell. Zebrafish are a preferred model for the determination of DNA function in mammals for several reasons. First, zebrafish is a complex vertebrate species which contains a majority of those genes found in higher vertebrates such as man. Moreover, nucleotide sequences are highly conserved between analogous zebrafish and mammalian genes [Schulte-Merker et al (1992) *Development* 116:1021–1032; Hermann et al (1990) *Nature* 343:617–622; Smith et al(1990) *Cell* 67:79–87; Blum et al (1992) *Cell* 69:1097–1106; Izpisua-Belmonte et al (1993) *Cell* 76:645–659; Blumberg et al (1991) *Science* 253:194–196; Stachel et al (1993) *Development* 117:1261–1274].

In addition, zebrafish are readily and inexpensively available from commercial sources, and can be maintained in a laboratory at a large number at a relatively small expense. The suitability of the zebrafish as a model organism for mammalian gene function is further enhanced by the early expression (within 4 hours after transfection) of expression vectors which are transiently transfected into fertilized zebrafish eggs.

Furthermore, transgenic zebrafish are easier to generate than transgenic mammalian animals because of a number of unique characteristics of this fish. Zebrafish are oviparous, utilize external fertilization and produce a large number of eggs, thus facilitating collection of a large number of eggs as hosts for heterologous nucleic acid sequences. Fish eggs are readily fertilized and cultured in vitro, and their development requires no attention from the parental fish. Fish eggs are transparent and their development can be monitored throughout embryogenesis. Heterologous DNA may be introduced by microinjection into the cytoplasm instead of into nuclei in mammalian eggs. Since fish eggs are much larger than mammalian eggs, microinjection can be accomplished in fish by using simple equipment. Typically, $10^6$ copies of foreign DNA in the form of either linear fragments or circular plasmid are microinjected into the cytoplasm of fish fertilized eggs, resulting in 20–80% survival. Approximately 1–50% of the surviving fertilized eggs are transgenic as determined by Southern blot analysis of DNA extracted from either the blood or fin of the host. Expression of transgenes is generally detected at various levels in 0–50% of the transgenic fish. Alternatively, transgenic fish may be produced by microinjection of foreign DNA into oocyte nuclei instead of into the cytoplasm of fertilized eggs [e.g., Inoue et al. (1989) Cell Differen. & Develop. 27:57–68], by electroporation of fertilized eggs with foreign DNA [Xie et al. (1989) Acta Hydrobiol. Sin. 13(40):387–389; Xie et al. (1993) Aquaculture 111: 207–213] or electroporation of sperm with foreign DNA followed by in vitro fertilization [Muller et al. (1993) FEBS Lett. 324:27–32; Patil et al. (1996) J. Exp. Zool. 274:121–129], or by microinjection of a pseudotyped retrovirus carrying a foreign gene into blastula-stage zebrafish embryos [Lin et al. (1994) Science 265, 666–669); Gaiano et al. (1996) Proc. Natl. Acad. Sci. USA 93, 7777–7782].

An additional advantage to the use of zebrafish in the methods of the invention is that zebrafish embryos are transparent and complete their embryonic development within 96 hours of fertilization. The transparency of the embryos facilitates continuous visual observation (e.g., under the microscope) of cells, tissues and organs in the developing embryo, as well as allows cell lineage analysis by dye tracing. The rapid development into an adult (within two months) allows observation of the effect of depleting the expression of genes which function during embryogenesis as well as in adulthood.

Additionally, cell replication of zebrafish embryos is much faster than that of any mammalian embryo cultured cell. When incubated at 28.5° C., the first cleavage takes about 45 minutes and after that the cells duplicate once every 15 minutes. As a result, the cell number exceeds 1000 at 3 hr post fertilization. This characteristic makes it possible to detect the expression of a foreign gene within a single egg shortly after injection. Expression of a luciferase gene driven by either a CMV promoter or a $T_7$ promoter in the host zebrafish embryos has been detected as early as 4 hr post fertilization, with a maximal expression level at 24 to 48 hr.

Yet another advantage of using zebrafish as host cells for expressing ribozyme sequences to determine gene function is that transient expression of ribozyme-encoding sequences in zebrafish yields results much more rapidly (i.e., within 96 hours required for completion of embryonic development) than using a transgenic mouse system (which requires several weeks to complete embryonic development).

Furthermore, the use of a zebrafish fertilized egg as host for ribozyme expression is superior to the use of cultured cells in that the fertilized egg is a living in vivo system in which the behavior of a foreign gene much more closely resembles that in a living organism as compared to in vitro cultured cells.

The methods of the invention exploit a unique aspect of gene transfer in fish eggs which is distinct from gene transfer in mice and other mammalian species. Whereas a very high percentage of mammalian fertilized eggs microinjected with DNA sequences integrates these sequences into the mammalian chromosome, in fish such stable chromosomal integration is rare [Zhu et al (1986) Kexue Tongbao Acad. Sin. 31:988–990; Zhu et al (1989) *Sci. Sin.* 2:147–155; Xie et al (1993) *Aquaculture* 111:207–213]. Nevertheless, in fish, a large number of injected DNA sequences is maintained and expressed in a transient fashion for prolonged time periods as episomal genetic elements [Zhu et al (1989) *Sci. Sin.* 2:147–155; Xie et al (1993) *Aquaculture* 111:207–213]. This is in contrast to mammalian embryonic gene transfer in which prolonged maintenance and expression of microinjected heterologous DNA sequences is not usually observed. Therefore, while the generation of stable transgenic fish or gene knockout fish (e.g., by integration or by homologous recombination of heterologous DNA sequences into the genome) is extremely difficult, fish species are highly suited for transient expression of high levels of a transgene product during embryogenesis and for much of the remainder of the first week of life, from the multiple episomal genetic elements still present following egg microinjection.

Zebrafish are commercially available from pet store shops and may be maintained using protocols well known in the art [see, e.g., Westerfield (1993) The zebrafish book: A guide for the laboratory use of zebrafish (*Brachidanio rerio*), Eugene: University of Oregon Press]. Development of a fully developed zebrafish from a fertilized egg occurs over a 96 h period of time during which time the developing embryo is transparent, thus facilitating observation of its tissues and organs. At 28.5° C., the following developmental period and events are observed beginning at the following times measured from fertilization: the zygote period at 0 hr; cleavage period at ¾ hr (the first 6 cleavages occur); blastula period at 2¼ hr (cleavages continues and epiboly begins); gastrula period at 5¼ hr (morphogenetic cell movements of involution; convergence and extension through the end of epiboly); segmentation period at 10 hr (tail forms; somites and other primary organs arise); straightening period at 24 hr (body axis straightens from its early curvature about the yolk sac); hatching period at 48 hr (natural escape from the chorion occurs synchronously); early larva period after 72 hr (swim bladder develops; food-seeking behavior appears). Following completion of embryogenesis over a 96 h period, sexually mature adult zebrafish may develop at the age of two-months, depending oil their nutritional condition. The well characterized zebrafish developmental periods and events occurring therein facilitate the detection of alterations in these events by the expression of ribozymes which target expression products of a gene of interest, thus allowing a determination of gene function.

C. Determination of Gene Function

Once an expression vector which encodes ribozyme is transiently or stably transfected into a host cell, the effect of ribozyme expression on the transfected cell (e.g., fertilized egg cell, cell derived from a cell line, plant protoplast, callous cell, protocorm-like body cell, etc.) and/or progeny (e.g., embryo, fetus, adult animal, plant, subsequent generations of a cell line, etc.) derived from this cell is determined in relation to controls which are not transfected with the expression vector, or which are transfected with an expression vector that encodes an RNA which does not cleave the substrate RNA. For example, morphological and pathological changes may be determined using methods known in the art such as by visual inspection, histological staining, electron microscopy, magnetic resonance imaging (MRI), computerized tomography (CT) scans and the like. Morphological changes as a result of ribozyme expression indicate that the gene whose transcript is cleaved by the ribozyme is important in the formation of the structure whose morphology is altered by ribozyme expression. In a preferred embodiment, the observed change is morphological. The zebrafish no tail (ntl) gene [Schulte-Merker et al (1992) supra; Schulte-Merker et al (1994) *Development* 120:1009–1015] was selected by the inventors as a target to "knockdown" it's expression since homozygous mutant fish lacking this functional gene do not form a tail [Halpern et al (1993) *Cell* 75:99–111] and this phenotype is easily observable and provides a convenient assay for the disruption of a specific gene function. Data presented herein show that the knockdown of ntl expression in zebrafish as a result of cleavage with one or more ribozymes directed to the mRNA product of the ntl gene successfully resulted in a no tail phenotype which was identical to that observed in zebrafish having a homozygous mutation in the ntl gene.

Alternatively, changes may be biochemical. Biochemical changes may be determined by, for example, changes in the activity of known enzymes, rate of accumulation or utilization of certain substrates, protein patterns on two-dimensional polyacrylamide gel electrophoresis, etc. Such changes in response to ribozyme expression suggest that the gene whose transcript is targeted by the ribozyme acts in the same pathway as the enzymes whose activity is altered, or in a related pathway which either supplies substrate to these pathways, or utilizes products generated by them.

Yet another alternative is to determine molecular biological changes using, for example, subtractive hybridization to produce a "subtracted cDNA library," or differential display reverse transcription-PCR (DDRT-PCR). A subtracted cDNA library contains cDNA clones corresponding to mRNAs present in one sample (i.e., a control sample) and not present in another (i.e., a sample in which mRNA expression has been "knocked down" as a result of treatment with ribozyme). See generally, *Current Protocols in Molecular Biology*, Section 5.8.9 (1990). In the protocol, cDNA containing the gene(s) of interest ["+cDNA"] (i.e., control sample not treated with ribozyme) is prepared with EcoRI ends and the cDNA not containing the gene(s) of interest ["–cDNA"] (i.e. sample treated with ribozyme) is prepared with blunt ends. The +cDNA is mixed with a 50-fold excess of –cDNA inserts and the mixture is heated to make the DNA single-stranded. Thereafter, the mixture is cooled to allow hybridization. Annealed cDNA inserts are ligated to a vector and transfected. In theory, the only +cDNA likely to be double-stranded with an EcoRI site at each end are those not hybridized to something in the –cDNA preparation; in other words, where a complementary sequence is in the –cDNA preparation, the sequence will not be transfected. Thus, only sequences unique to the +cDNA preparation will be cloned and amplified. Following sequence determination of these unique sequences, a function of the knocked down mRNA expression on transcription of these sequences may be ascertained.

The DDRT-PCR method is based on the polymerase chain reaction, which is described by Mullis, et al., in U.S. Pat. Nos. 4,683,195, 4,683,202 and 4,965,188, hereby incorporated by reference. Briefly, the PCR process consists of introducing a molar excess of two oligonucleotide primers to the DNA mixture containing the desired target sequence. The two primers are complementary to their respective strands of the double-stranded sequence. The mixture is denatured and then allowed to hybridize. Following hybridization, the primers are extended with a thermostable DNA polymerase so as to form complementary strands. The steps of denaturation, hybridization, and polymerase extension can be repeated as often as needed to obtain a relatively high concentration of a segment of the desired target sequence.

In the case of DDRT-PCR, the target is mRNA; the mRNA is, however, treated with reverse transcriptase in the presence of oligo(dT) primers to make cDNA prior to the PCR process. The PCR is carried out with random primers in combination with the oligo(dT) primer used for cDNA synthesis. In theory, since only mRNA is (indirectly) amplified, only the expressed genes are amplified. Where two samples are to be compared, the amplified products are placed in side-by-side lanes of a gel; following electrophoresis, the products can be compared or "differentially displayed."

Improved DDRT-PCR methods have been described in the art, including for example, the improvements described by E. Haag, et al, "Effects of Primer Choice and Source of Taq DNA Polymerase on the Banding Patterns of Differential Display RT-PCR," *Biotechniques* 17:226–228 (1994), whereby the use of the standard oligo-dT primer in the PCR step is omitted to decrease the faint banding at essentially every position of the electrophoresis gel. Instead, a second arbitrary primer was utilized in PCR. Another example is O.C. Ikonomov, et al, "Differential Display Protocol With Selected Primers That Preferentially Isolate mRNAs of Moderate to Low Abundance in a Microscopic System," *Biotechniques* 20:1030–1042 (1996); this paper describes the use of a modified DDRT-PCR protocol to increase bias towards moderate to low abundance transcripts, rather than towards high-coy number genes. The authors utilized experimentally selected primer pairs directed at known coding sequences that avoid amplification of highly abundant ribosomal and mitochondrial transcripts.

Yet another alternative is the determination of behavioral changes in an organism. Where the organism is unicellular e.g. yeast cell, or bacterium, such changes may include light tropism, chemical tropism and the like, and would suggest that the gene whose expression is reduced by ribozyme regulates these events. Where behavioral changes are observed in a multicellular organism, e.g., loss of spatial memory, aggressiveness, etc., such changes indicate that the gene whose transcript is targeted by the ribozyme functions in a neural pathway involved in controlling such behavior.

Other changes include molecular biological changes, e.g. in the levels of expression of genes as determined by, for example, subtraction hybridization. Such changes suggest that the gene whose transcript is targeted by the ribozyme encodes a transcriptional regulatory molecule such as a transcription factor.

EXPERIMENTAL

The following examples serve to illustrate certain preferred embodiments and aspects of the present invention and are not to be construed as limiting the scope thereof.

EXAMPLE 1

Knockdown of Zebrafish ntl gene Expression Using Ribozyme Sequences Expressed Under the Control of Adenovirus Polymerase III Promoter In order to determine the feasibility of using ribozymes which cleave a transcribed message encoded by a specific gene to determine gene function, ribozymes were designed to reduce expression of a gene of a unknown function in zebra fish, and the effect of this reduced gene expression on gene function was determined. The gene selected was the zebrafish ntl gene. The zebrafish ntl gene has been cloned, sequenced, and the amino acid sequence deduced [Schulte-Merker et al. (1994) supra, Schulte-Merker et al. (1992) supra] and found to be the homologue of the mouse T (Brachyury) gene and of the Xbra gene of Xenopus. Two zebrafish mutations in the ntl locus were each found to result in lack of differentiated notochord and the most posterior 11–13 of their normal 30 somites, resulting in no tail and death around day 5 [Halpern et al. (1993) supra]. The phenotype of the two zebrafish mutants resembled that of mouse T mutants, ntl was transcribed as early as 3.4 hr in zebrafish embryos. Because the ntl gene sequence and its function in zebrafish tail formation were known, the effect of knocking down ntl gene expression by ribozymes, which are designed to specifically cleave mRNA encoded by the zebrafish ntl gene, on the tail/no tail phenotype was investigated. This Example involved (A) Selection of Substrate Cleavage Sites on ntl mRNA, (B) Construction of ntl Ribozyme Expression Vectors Containing Ribozyme Genes Controlled by Adenovirus Polymerase III Promoter, (C) Maintenance of Zebrafish and Production of Fertilized Eggs. (D) Microinjection of Plasmids Into Fertilized Eggs, (E) Development of Zebrafish Embryos, and (F) Phenotype of Zebrafish Embryos Injected With Ribozyme Vectors.

A. Selection of Substrate Cleavage Sites On ntl mRNA

The sequence of the zebrafish ntl cDNA (FIG. 1) (SEQ ID NO:5) which has been previously described by Schulte-Merker et al. (1992) supra, was used in an "RNADRAW" program to generate a model of the secondary structure of the ntl mRNA. A graphic representation of the secondary mRNA structure obtained by "RNADRAW" is shown in FIG. 2. The secondary structure included information on possible stem and loop structures as well as unpaired sequence regions. All the GUC and CUC sites in this substrate mRNA molecule were determined manually (this takes only a few minutes) and localized to the loop structures or unpaired regions as such sites were hypothesized to be more likely to be attacked by ribozyme molecules.

A total of 160 loops and unpaired regions were detected. Three loop sequences which contained a GUC or CUC sequence were located within 600 nucleotides downstream of the start codon (AUG) and were selected as substrate cleavage sites for ribozyme cleavage as it was hypothesized that the resulting truncated protein product would be biologically inactive, based on the observation that a truncated ntl protein of 245 amino acids is biologically inactive in the ntl mutant zebrafish. The regions of complementarity flanking the GUC or CUC sites were 8-nt long.

The first loop sequence was loop 50 (FIG. 3A) which was 14-nt long and contained a substrate cleavage site of the sequence CUC at position 435 of the ntl mRNA. The position of the substrate cleavage site was based on a numbering system in which the transcription start sequence AUG was at position 1. Thus, position 435 on the ntl mRNA corresponded to position 516 on ntl cDNA of FIG. 1. A 17-nt target sequence 5'-AAU AAA CUC AAC GGA GG-3' (SEQ ID NO:7) was selected for cleavage by a ribozyme designated Ribozyme$_{435}$. The second loop sequence was loop 45 (FIG. 3B) which was 12-nt long and contained a target site of the sequence CUC at position 365 of the ntl mRNA (i.e., position 446 on ntl cDNA of FIG. 1). A 17-nt target sequence 5'-CCC GGA CUC ACC CAA CU-3' (SEQ ID NO:8) was selected for cleavage by a ribozyme designated Ribozyme$_{365}$. The third loop sequence was loop 65 (FIG. 3C) which was 9-nt long and contained a target site of the sequence GUC at position 564 of the ntl mRNA (i.e., position 645 of the ntl cDNA of FIG. 1). A 17-nt target sequence 5'-AUU GCA GUC ACA GCA UA-3' (SEQ ID NO:9) was selected for cleavage by a ribozyme designated Ribozyme$_{564}$.

B. Construction of ntl Ribozyme Expression Vectors Containing Ribozyme Genes Controlled by Adenovirus Polymerase III Promoter The expression construct for the ribozyme sequence was designed to result in high-level expression and stability of the expressed RNA (ribozyme) molecules. For high-level gene expression, the transcription of the ntl ribozyme gene was driven by a human adenovirus-associated type 2 virus RNA I gene (va RNAI) promoter sequence which is recognized by RNA polymerase III. This adenovirus promoter is an intragenic promoter which serves as a promoter as well as a part of the RNA I gene itself. An expression vector (pGvaL) (FIG. 8) (SEQ ID NO:10) was constructed by inserting downstream of the vaRNAI gene a DNA fragment whose transcript pairs with one part of the vaRNA I transcript and forms a double-stranded RNA structure. Briefly, the Aat II site in the pGEM7zf+ plasmid (Promega, Madison, Wis.) was deleted and the Xba I/Nsi I fragment containing the vaRNA I and vaRNA II genes was inserted into the Xba I/Pst I site of the pGEM7zf+. A double-stranded DNA fragment was obtained by annealing oligonucleotide I [5'-CGTCGACTGCGCAGTGCAGCGTGTGGA CCCAACGACACGCGGGCGGTAACCGACGT-3' (SEQ ID NO:11)] and oligonucleotide II [5'-

CGGTTACCGCCCGCGTGTCGTTGGGTCCACA CGCTGCACTGCAGCAGTCGACGACGT-3' (SEQ ID NO:12)] and inserting the annealed fragment into the At II site within the va gene. The recombinant ribozyme molecule expressed from a ribozyme gene embedded inside the vaRNA I gene in the pGvaL vector has a stem-loop structure with ribozyme located in the big loop and its flanking sequences on both ends forming a stem (double-stranded) structure. It has been shown that this stem-loop RNA secondary structure can significantly increase the stability and resistance of embedded ribozyme RNA molecules against degradation by nuclease [Lieber and Strauss (1995) Mol. Cell. Biol. 15:540–551].

Figure 4:
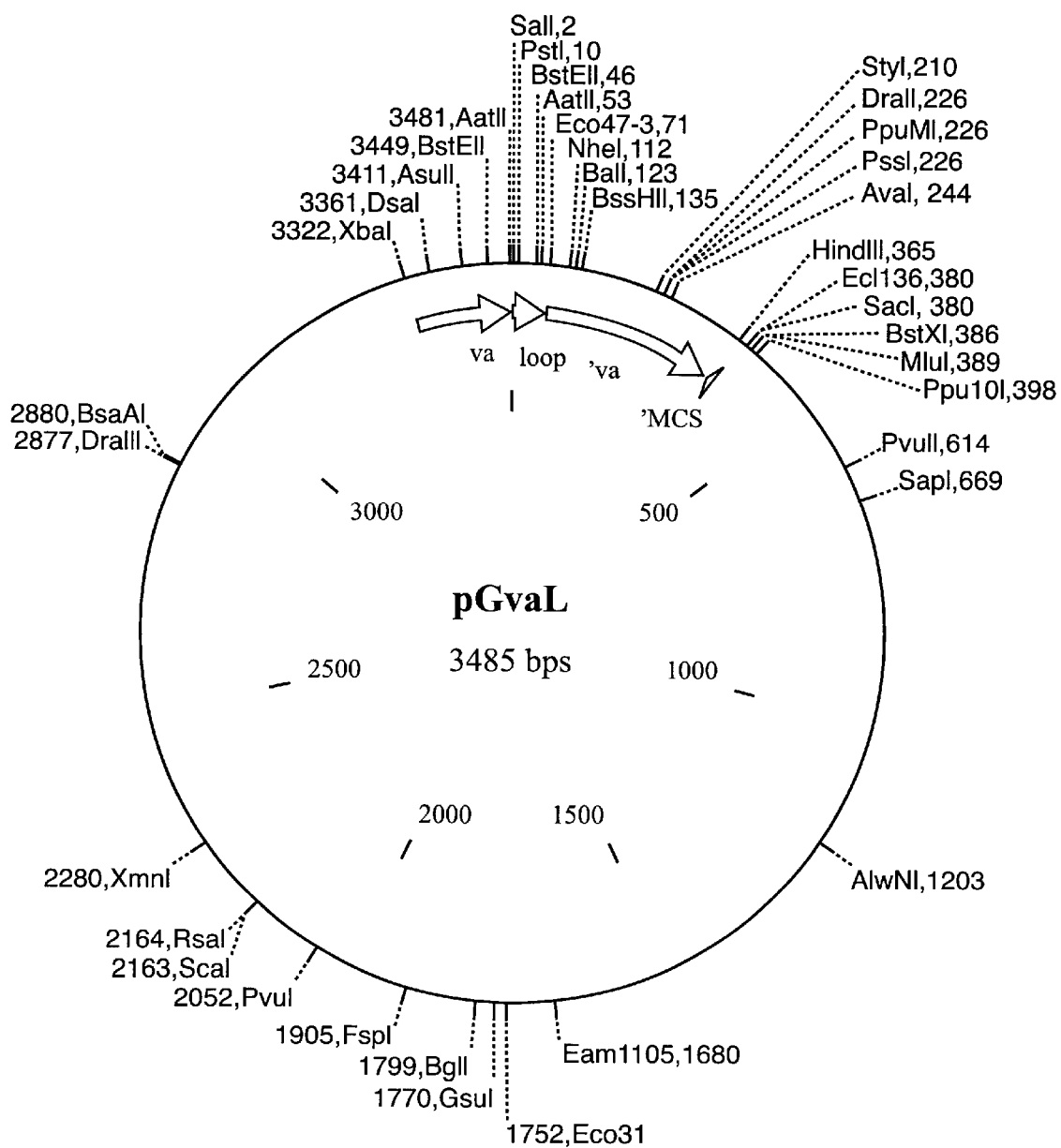
FIG. 4 shows the structure of pGVaL.

In lytic viral infections, vaRNA accumulates at high concentrations in the cytoplasm, and is synthesized by RNA pol III from a promoter within the transcribed sequence with characteristic and essential elements for transcriptional initiation in the regions at positions +10 to +16 and +58 to +68. The RNA pol III promoter is active in all cell types. Transcription by RNA pol III terminates at an oligo(dT) tract. Ribozymes were designed to be expressed as part of vaRNA since they were expected to be expressed in a stable form and to be transported to the cytoplasm in a manner similar to that for spliced mRNA. To this end, plasmid pGvaL (FIG. 4) which has been previously described [Lieber and Strauss (1995) supra] was used. The ribozyme gene was positioned within the loop to allow the structure of the ribozyme to form independently of the sequence of flanking regions.

Ribozyme genes were synthesized as two complementary single-stranded oligonucleotides containing the catalytic core, 8 nt long binding regions on both sides of the catalytic core, a Sal I site at the 5'-end, and a Pst I site at the 3'-end. All oligonucleotides were synthesized by Oligos Terapeutics, Inc., and all enzymes were purchased from New England Biolabs. Ribozyme$_{435}$ oligonucleotide #1 (47 mer) 5'-TCGACCTCCGTTCTGATGAGTCCGTGAGGACG AAAGTTTATTCTGCA-3' (SEQ ID NO:13) and oligonucleotide #2 (39 mer) 5'-GAATAAACTTTCGTCCTC ACGGACTCATCAGAACGGAGG-3' (SEQ ID NO:14) were designed to cleave at site 1. Ribozyme$_{365}$ oligonucleotide #3 (48 mer) 5'-TCGACAGTTGGGTCTGATGA GTCCGTGAGGACGAAAGTCCGGGCTGCA-3' (SEQ ID NO:15) and oligonucleotide #4 (40 mer) 5'-GCCCGGACTTTCGTCCTCACG GACTCATCAGACCCAACTG-3' (SEQ ID NO:16) were designed to cleave at site 2. Ribozyme$_{564}$ oligonucleotide #5 (48 mer) 5'-TCGACTATGCTGTCTGATGAGTCCGTGAGGAC GAAACTGCAA TCTGCA-3' (SEQ ID NO:17) and oligonucleotide #6 (40 mer) 5'-GATTGCAGTTTCGTCCTCACGGACTCATCAGA CAGCATAG-3' (SEQ ID NO:18) were designed to cleave at site 3. 1000 ng of each oligonucleotide pair were annealed in in 1X annealing buffer in a total volume of 20 µl (heated to 75° C. and allowed to slowly cool to 25° C. to form a double-stranded DNA fragment with a Sal I end at the 5'-end and a Pst I end at the 3'-end. This Sal I/Pst I fragment was then inserted into the Sal I/Pst I sites of plasmid pGval, [Lieber and Strauss (1995) supra] to produce plasmids pGvaRz$_{365}$, pGvaRz$_{435}$, and pGvaRz$_{564}$ which encoded, respectively, Ribozyme$_{365}$, Ribozyme$_{435}$ and Ribozyme$_{564}$. In the pGvaRz vectors, the ribozyme gene(s) was under the control of an adenovirus va promoter which is an RNA polymerase III promoter.

FIG. 5b shows the ribozyme sequence of Ribozyme$_{435}$ (Rz(ntl)$_{435}$) [5'-CCUCCGUUCUGAUGAGUCCGUGAGGACGAAA GUUUAUU-3' (SEQ ID NO:19)] embedded within the va RNA loop and the sequences flanking the ribozyme. The sequences flanking Rz(ntl) were designed such that the 5' and 3' flanking regions of the ntl ribozyme form a stable stem structure [Lieber and Strauss (1995), supra] with the ntl ribozyme located in the center of the loop which can attack the target ntl mRNA sequence shown in FIG. 5b [5'-AAUAAACUCAACGGAGG-3' (SEQ ID NO:7)]. Both the ribozyme and its targeted, complementary ntl mRNA sequences, as well as the cleavage site (435) are also shown. The ribozyme sequence of Ribozyme$_{365}$ (Rz(ntl)$_{365}$) is 5'-GGGCCUGAAAGCAGGAGUGCCUGA GUAGUCUGGGUUGA-3' (SEQ ID NO:20) which targets SEQ ID NO:8, while the ribozyme sequence of Ribozyme$_{564}$ (Rz(ntl)$_{564}$) is 5'-UAACGUCAAAGCAGGA GUGCCUGAGUAGUCUGUCGUAU-3' (SEQ ID NO:21) which targets SEQ ID NO:9.

C. Maintenance of Zebrafish And Production of Fertilized Eggs

Zebrafish were maintained essentially as previously described [Westerfield (1993) supra] with the following modifications. Up to 50 fish were maintained in 5 gallon aquaria heated to 28.5° C. Two-thirds of the water in the tanks was replaced every 5 days by siphoning off debris from the bottom of the tank. Filtered tap water was left exposed for at least one day to release chlorine before it was used to refill the tanks. Zebrafish were obtained from the University of Oregon and were fed twice a day with flake in the morning and live brine shrimp in the evening.

Zebrafish are photoperiodic in their breeding and the production of eggs starts shortly after sunrise (i.e., about 15 minutes after the light is turned on in the morning in the laboratory). The day-night cycle was controlled by an automatic timer (15 hours light/9 hours dark). Depending on their nutritional condition, zebrafish became sexually mature when they were 3 to 4 months old. However, breeding fish between 5 and 18 months of age were used in order to obtain high quality eggs.

One week before eggs were collected, male breeding fish were separated from females and kept in separate tanks with up to 30 fish per 5 gallon tank with normal maintenance. On the day before collection of eggs, 1–3 hr before the light were turned off, the fish were fed with live brine shrimp for 30 minutes, and 3 males and 5 females were transferred into a covered 2 gallon tank filled with fresh water. The entire bottom of the tank was covered with a single layer of marbles to keep the fish from eating the newly spawned eggs. The fish started to spawn 15 to 30 minutes after the beginning of the next light cycle. To obtain fertilized eggs at the one-cell stage, the eggs were collected every 20 minutes by siphoning them up from among the marbles at the bottom of the tank through a medium-mesh screen. The eggs were washed off the screen into a petri dish by inverting the screen and washing with salted water (60 mg instant ocean salt in 1 liter distilled water). Typically, 500 to 800 eggs were obtained from each tank within a 2–3 hours period.

D. Microinjection of Plasmids Into Fertilized Eggs

Whole plasmid DNA was used for microinjection since there is evidence in the art that circular plasmid DNA can persist and be expressed in the fish embryos longer than the linear form [Zhu et al. (1989) supra, Xie et al. (1993) supra].

For injection of pGvaRz vectors, a DNA solution containing equal concentration (100 μg/ml) in LST buffer [44 mM NaCl, 5 mM Tris.HCl, pH 7.0] of each of the three pGvaRz vectors was used for microinjection.

Microinjection was performed using methods known in the art [Zhu et al. (1986) supra, Xie et al. (1993) supra]. Each fertilized egg at the single cell stage, 0.5 hr. post fertilization, received about 2 nl of microinjection solution after chorion removal by treatment with a 0.25% trypsin solution. After microinjection, the injected embryos were maintained in HS solution (0.35% NaCl, 0.01% KCl and 0.01% $CaCl_2$) at 28.5° C.

E. Development of Zebrafish Embryos

Manipulated eggs which were injected with foreign DNA were raised at a density of 100 embryos per 90 mm petri dish in IIS solution containing 50 μg/ml ampicillin, at 28.5° C. in a water bath incubator. Embryos typically completed their embryonic development at day 3 post fertilization when untreated embryos normally hatched but did not need to be fed until day 4 after fertilization. At that time, 50 larvae were transferred to a 200 ml beaker filled with 150 ml salted water, and the larvae were fed with live paramecia. The phenotype can be observed under the microscope as early as 24 hr post fertilization, and was macroscopically visible after 48 hr and until the fish died (up to 10 days).

F. Phenotype of Zebrafish Embryos Injected With Ribozyme Vectors

Microinjection of a mixture of the three plasmids $pGvaRz_{435}$, $pGvaRz_{365}$ and $pGvaRz_{564}$ which encoded $Ribozyme_{435}$, $Ribozyme_{365}$ and $Ribozyme_{564}$, respectively, resulted in "partial no tail" mutants (i.e., had shorter and/or mishapen tails (FIG. 6b) compared to wild-type controls which had been injected with a vector lacking a ribozyme gene) at an early developmental stage. The mutation was observed in embryos at a rate of approximately 5% as early as 24 h post-transfection.

Since three expression vectors were simultaneously transfected, these results showed that at least one of the three expressed ribozymes was effective in cleaving the zebrafish ntl gene thus resulting in reduced ntl mRNA expression together with the expression of a phenotype (i.e., "partial no tail" phenotype) which partially resembled that of the previously reported ntl mutants [Halpern et al. (1993) supra] which lacked a tail (FIG. 6d). These results also show that expression of ribozymes in the nucleus is sufficient for their function in cleaving substrate RNA sequences, and that it is not necessary to express ribozymes in the cytoplasm of a cell in order for the ribozyme to be active.

These results demonstrate that reducing the expression of a gene in zebrafish by ribozyme cleavage coupled with the observation of a resulting altered phenotype is useful in determining the function of the gene whose expression is reduced.

EXAMPLE 2

Knockdown of Zebrafish ntl gene Expression Using Ribozyme Sequences Expressed Under the Control of a $T_7$/Adenovirus Polymerase III Double-Promoter Because the no tail phenotype was not observed in zebrafish in which ntl ribozyme was expressed under the control of the vaRNA I promoter, it was hypothesized that the expression level of the ribozymes was not sufficiently high to completely knock down the expression of the ntl gene. Thus, vectors which expressed higher levels of ribozyme sequence than those expressed under the control of the adenovirus polymerase III promoter were designed. A double-promoter vector was designed in which transcription of ribozymes was driven by cooperation of an adenovirus promoter sequence with endogenous polymerase III as well as by interaction of the $T_7$ promoter sequence with exogenous $T_7$ polymerase. A previously described expression system was used in which the $T_7$ polymerase gene is operably linked to its cognate $T_7$ promoter (in a $T_7T_7$ plasmid) and in which $T_7$ polymerase is co-delivered with the expression system to initiate transcription [Wagner et al., U.S. Pat. No. 5,591,601]. This example involved (A) Construction of Helper Plasmid $pT_7T_7$, (B) Construction of ntl Ribozyme Expression Vectors Containing Ribozyme Genes Controlled By a Double Promoter ($T_7$-Va promoter), (C) Microinjection Of Plasmids Into Fertilized Eggs, (D) Phenotype Of Zebrafish Embryos Injected With Ribozyme Vectors, and (E) Northern Blot Analysis.

A. Construction of helper plasmid $pT_7T_7$

Plasmid $pT_7T_7$ was used to provide a $T_7$ polymerase gene controlled by $T_7$ promoter. $pT_7T_7$ was constructed as previously described by Wagner et al., U.S. Pat. No. 5,591,601, the entire contents of which are incorporated by reference. Briefly, a fragment of pAR1173 containing a $T_7$ gene was inserted into pTM-1 vector [Wagner et al., (1994) Nucleic Acids Research 22: 2114–2120, Moss et al. (1990) Nature 348:91–92; and Wagner et al., U.S. Pat. No. 5,591,601], a cytoplasmic expression vector which contains a $T_7$ promoter connected at its 3' end to an EMC capping independent sequence into which was inserted a Lac I repressor gene and an operator sequence which provides the biding site for the Lac I repressor. The Shine-Delgarno sequence of the $T_7$ gene was removed. A NcoI site was added to the $T_7$ gene and the ATG codon of the $T_7$ gene was adjusted in a manner such that translation of the $T_7$ gene would be initiated from the ATG in the NcoI site.

B. Construction of ntl ribozyme expression vectors containing ribozyme genes controlled by a double promoter ($T_7$-Va promoter)

Figure 5:
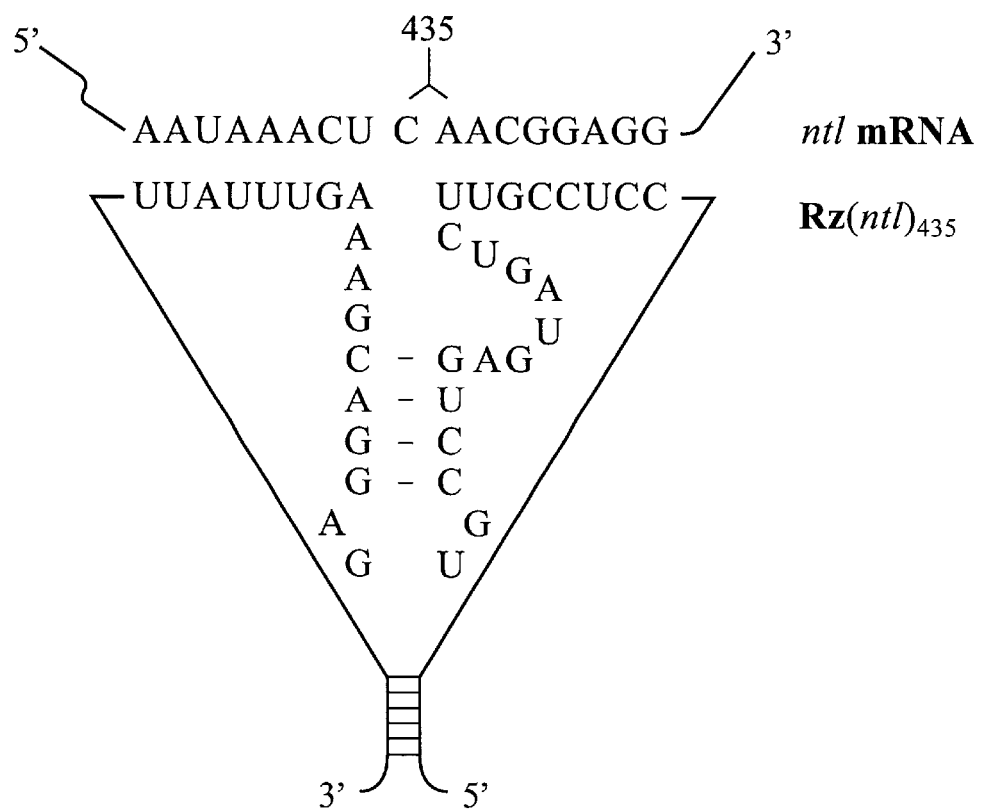
FIGS. 5 (parts A–B) show the structure of (A) the pT$_7$vaRz(ntl) ribozyme expression vector, and (b) a schematic secondary structure of ntl ribozyme RNA.

In order to generate a construct in which the ribozyme gene was controlled by a double promoter, each of the pGvaRz plasmids described above was subjected to Xba I/Sac I digestions and a 579 bp ($pGvaRz_{435}$,) or 580 bp ($pGvaRz_{365}$ and $pGvaRz_{564}$) (see FIG. 8 for the sequence of pGvaL,) fragment containing the va promoter and ribozyme sequences was generated and inserted into the EcoR I/Sac I sites of a modified pTM-1 vector (pTM-2) in which the EMC sequence has been removed [Moss et al. (1990) supra] which lacks the EMC sequence (both of the Xba I and EcoR I sites were blunt ended by Klenow filling-in before Sac I cleavage). The resulting plasmids were named $pT_7vaRz(ntl)_{365}$, $pT_7vaRz(ntl)_{435}$, and $pT_7vaRz(ntl)_{564}$ ribzyme expression vectors which encoded, respectively, $Ribozyme_{365}$, $Ribozyme_{435}$ and $Ribozyme_{564}$. Expression of the ribozyme sequences in these plasmids was under the control of the two tandemly arranged $T_7$ and vaRNA I promoters as shown in FIG. 5.

FIG. 5a shows the ntl ribozyme expression vector pT$_7$vaRz. The vector pT$_7$vaRz(ntl) was constructed first by an insertion of a ribozyme sequence (Rz) against the ntl mRNA into a vaRNA I expression cassette [Lieber and Strauss (1995) supra]. The cassette containing the va promoter and ribozyme sequence (va-Rz-loop-va') was subsequently cloned into a modified pTM-1 expression vector which lacks the EMC sequence in such a way that the expression of ribozyme is under the control of both a T$_7$ promoter (P$_{T7}$) and an adenovirus va I internal promoter, a polymerase III promoter (upstream va). The EMC sequence is a Cap-independent sequence which allows transcription of mRNA by T$_7$ RNA polymerase in the cytoplasm where mRNA does not have a Cap structure. The P$_{T7}$-driven transcription stops at the T$_7$ terminator (T$_{17}$), whereas the va I-driven transcription terminates at the multiple T at the 3' end of the va gene.

C. Microinjection of plasmids into fertilized eggs pT$_7$vaRz ribozyme expression vectors were injected into fertilized zebrafish eggs at the one-cell stage as described above. For injection of pT$_7$vaRz ribozyme expression vectors, the three pT$_7$vaRz ribozyme expression vectors were injected into the eggs either singly or as a mixture of the three pT$_7$vaRz ribozyme expression vectors. A 2 nl DNA solution containing a final concentration of 90 ng/µl of pT$_7$vaRz ribozyme expression vector DNA, with or without, 10 ng/µl of pT$_7$ plasmid DNA [Chen et al (1994) Nucleic Acids Res. 22:2114–2120] and 2.5 unit/µl of T$_7$ RNA polymerase (New England Biolab) was microinjected into each egg. Each egg thus received a final amount of approximately 200 pg or 180 pg pT$_7$vaRz DNA and 20 pg pT$_7$T$_7$ DNA.

D. Phenotype of zebrafish embryos injected with ribozyme vectors

Microinjection of a mixture of the three ribozyme expression plasmids pT$_7$vaRz$_{435}$, pT$_7$vaRz$_{365}$, and pT$_7$vaRz$_{564}$ together with the helper plasmid pT$_7$T$_7$ and pre-bound T$_7$ RNA polymerase resulted in a phenotypic change of host zebrafish embryos at an early developmental stage. The phenotypic change included no tail and partial no tail (FIG. 6). The no tail phenotype was identical to that observed in spontaneous no tail mutants in which the ntl gene was mutated [Halpern et al. (1993) supra]. The partial no tail mutants had shortened and mis-shape tails as compared to uninfected embryos or the controls which were injected with a control pT$_7$va vector that was produced by deletion of the ribozyme coding sequence from pT$_7$vaRz ribozyme expression vector. Approximately 3% of the embryos injected with a mixture of the three plasmids had a no tail phenotype, 10% had a partial no tail phenotype and the remaining 87% had a wild-type phenotype.

Microinjection of each individual pT$_7$vaRz ribozyme expression plasmid with the helper plasmid pT$_7$T$_7$ and pre-bound T$_7$ RNA polymerase resulted in different intron proportions of no tail and partial no tail phenotypes. While ribozyme expression plasmids pT$_7$vaRz(ntl)$_{365}$ and pT$_7$vaRz(ntl)$_{564}$ co-injected with the pT$_7$T$_7$ plasmid system showed the no tail phenotype to a limited extent, only ribozyme expression plasmid pT$_7$vaRz(ntl)$_{435}$ showed the full no tail phenotype. The results from a combination of four separate experiment showed that 7% of fry developing from zebrafish fertilized eggs which were co-injected with pT$_7$vaRz(ntl)$_{435}$ ribozyme expression plasmid and pT$_7$T$_7$ plasmid pre-bound to T$_7$ RNA polymerase had a phenotype indistinguishable from the ntl mutant line of zebrafish (FIG. 6 and Table 1).

TABLE 1

Zebrafish egg injections and resulting phenotypic change[a]

| Injected material | Egg injected | Egg survived 96 hr. post fertilization | Phenotype[b] | | |
|---|---|---|---|---|---|
| | | | Normal | Partial no tail | Full no tail |
| Uninjected | — | 501 | 501 | 0 | 0 |
| pT$_7$va[c] + pT$_7$T$_7$ + T$_7$ RNAP | 508 | 211 | 211 | 0 | 0 |
| pT$_7$vaRz(ntl)$_{435}$ + pT$_7$T$_7$ + T$_7$ RNAP | 799 | 316 | 256 (81%)[d] | 38 (12%)[d] | 22 (7%)[d] |

[a]Values show the number of fish.
[b]The phenotypes are shown in FIG. 6.
[c]pT$_7$va is a control plasmid produced by deletion of ribozyme coding sequences from pT$_7$vaRz.
[d]The percentage is calculated by dividing the number of the fish with a phenotypic change by the number of surviving fish.

FIG. 6 shows the phenotypic changes following development of zebrafish eggs which had been injected with ribozyme expression plasmid pT$_7$vaRz(ntl)$_{435}$, pT$_7$T$_7$ and T$_7$ RNA polymerase. FIG. 6a shows normal zebrafish at 96 hours of embryogenesis. FIG. 6b shows two examples of partial no tail phenotypic changes at 96 hours of embryogenesis in zebrafish developing from eggs injected with ribozyme expression plasmid pT$_7$vaRz(ntl)$_{435}$, pT$_7$T$_7$ and T$_7$ RNA polymerase. FIG. 6c shows an example of full no tail phenotypic changes at 96 hours of embryogenesis in zebrafish developing from eggs injected with ribozyme expression plasmid pT$_7$vaRz(ntl)$_{435}$, pT$_7$T$_7$ and T$_7$ RNA polymerase. FIG. 6d shows an example of a previously described [Halpern et al. (1993) Cell 75:99–111] homozygous no tail mutant zebrafish (ntl$^{b195}$) at 96 hours of embryogenesis.

In addition to the full no tail phenotype, a higher percentage (12%) of the fry developing from these injected eggs showed a degree of the no tail phenotype (partial) sufficient to indicate the function of the ntl gene (FIG. 6 and Table 1).

The results from at least eight (8) experiments showed that the development of a partial no tail phenotype and full no tail phenotype was reproducible. At 96 hours of embryogenesis, fish which developed from eggs injected with pT$_7$vaRz(ntl)$_{435}$ ribozyme expression plasmid and pT$_7$T$_7$ plasmid pre-bound to T$_7$ RNA polymerase were 5–15% no tail phenotype and 5–20% partial no tail phenotype, and about 80% wild-type phenotype; fish which developed from eggs injected with pT$_7$vaRz(ntl)$_{365}$ ribozyme expression plasmid and pT$_7$T$_7$ plasmid pre-bound to T$_7$ RNA polymerase were 5–20% partial no tail phenotype with the remaining fish showing a wild-type phenotype; fish which developed from eggs injected with pT$_7$vaRz(ntl)$_{564}$ ribozyme expression plasmid and pT$_7$T$_7$ plasmid pre-bound to T$_7$ RNA polymerase were 5–10% of partial no tail phenotype with the remaining fish showing a wild-type phenotype. Neither of the ribozyme expression plasmids pT$_7$vaRz(ntl)$_{365}$ or pT$_7$vaRz(ntl)$_{564}$ alone resulted in a no tail phenotype.

In order to determine whether the observed effect of ribozyme expression was the result of cleavage of the target ntl mRNA by the ribozyme rather than the result of antisense binding of the ribozyme to the ntl mRNA in the absence of cleavage, the effect of ntl antisense on phenotype was investigated. 300 fertilized zebrafish eggs were injected with a 21 base antisense deoxyoligonucleotide sequence (SEQ ID NO:22) 5'-CTGTCATGAGACGCAAGACTT-3' complementary to the Rz(ntl)$_{435}$ target sequence at molar concentrations 200 fold higher than the injected pT$_7$vaRz(ntl)$_{435}$ ribozyme expression plasmid. No phenotype other than wild-type was observed in the resulting 150 fry. These results demonstrate the specificity of the ribozyme sequences. In addition, without limiting the invention to a particular theory or mechanism, these results also demonstrate that the ribozymes operated not simply by antisense binding to the target mRNA sequence, but by cleaving the target mRNA.

In order to determine if cytoplasmic or nuclear ribozyme expression was most effective at disrupting gene expression, duplicate experiments with and without 20 pg of pT$_7$T$_7$ plasmid with pre-bound T$_7$ RNA polymerase were carried out for each of the ribozyme encoding ribozyme expression plasmids pT$_7$vaRz(ntl)$_{435}$, and pT$_7$vaRz(ntl)$_{564}$. It was hypothesized that since cytoplasmic expression driven by the T$_7$ promoter of each of the pT$_7$vaRz(ntl) ribozyme expression plasmids requires co-injection with a pT$_7$T$_7$ plasmid pre-bound to T$_7$ RNA polymerase [Chen et al. (1994) Nucl. Acids Res. 22:2114–2120], the presence or absence of this source of T$_7$ RNA polymerase would determine whether or not cytoplasmic ribozyme expression was present within the developing zebrafish egg. Of the six separate experiments, only the three which included the 20 pg of pT$_7$T$_7$ plasmid with pre-bound T$_7$ RNA polymerase resulted in fry with any evidence of the no tacil phenotype (data not shown).

These results demonstrate that while nuclear expression of ribozyme is sufficient to determine gene function (Example 1), the combination of nuclear expression and cytoplasmic expression of ribozyme can significantly increase the expression level of ribozyme and the ability of this zebrafish embryo transient expression system to identify gene function.

E. Northern Blot Analysis

In order to confirm both the presence of the ntl targeted ribozyme and the destruction of ntl mRNA in zebrafish embryos injected with the ribozyme expressing pT$_7$vaRz (ntl)$_{435}$/pT$_7$T$_7$ plasmid combination, Northern analysis of the RNA complement of these embryos was performed. RNA was isolated from injected zebrafish embryos at 5.2 hours after fertilization, the time period when ntl message is reported to be at it's highest level [Schulte-Merker et al. (1992) Development 116:1021–1032], as well as at 12 and 24 hours post fertilization and used for a Northern hybridization experiment using a labeled probe specific for the ntl message.

1. DNA fragments and probe preparation

For ntl mRNA detection, a 900 bp ntl cDNA fragment (114–1014) was amplified from zebrafish embryo total RNA by RT-PCR using a pair of primers [the 5'-primer (21nt) (SEQ ID NO:23) 5'-GGAATCATCTCCTTAGCCCCGT-3', and the 3'-primer (21nt) (SEQ ID NO:24) 5'-CTGTCATGAGACGCAAGACTT-3']. For RT-PCR, all components except RNA template and primers were supplied by a RT-PCR kit (Promega), and the reaction included 0.1 µg total RNA from 24 hr zebrafish embryos and 0.5 ug of each primer, in a 50 ul reaction volume. For RT-PCR reaction, the mixture was incubated at 94° C. for 2 min, then at 48° C. for 10 min, 1 µl of RTase was added to each sample, incubated at 48° C. for 45 min. The samples were then subjected to 40 PCR cycles as follows: 94° C. for min, 55° C. for 1 min, and 72° C. for 2 min. The samples were then incubated at 72° C. for 6 min. The amplified fragment was then cloned into the EcoRV sites of the pCR-3 vector (Promega) to generate plasmid pCRntl. A 900 bp fragment was recovered after EcoR I/Xho I cleavage of pCRntl and used as the template for production of the ntl gene probe. For ribozyme RNA detection, an approximately 600 bp fragment containing the vaRNA I promoter and the ribozyme gene was recovered after EcoR I/Mlu I digestion of pT$_7$vaRz ribozyme expression plasmid and used as a probe. An approximately 2 kb fragment of the mouse β-actin mRNA served as an internal control for quantitation of the total RNA of each sample in Northern blots. The probes were $^{32}$P-labeled using a random-primer kit (Gibco-BRL) following the manufacturer's instructions and used for hybridization as described in the following section.

2. RNA preparation and Northern blotting analyses

Total RNA from 50 injected or uninfected zebrafish embryos at 5.2 hr, 12 hr, and 24 hr post fertilization was isolated by using the RNAzol method (Chomcynski and Sacchi (1987) Anal. Biohem. 162:156–159). After ethanol precipitation and drying, total RNA was dissolved in DEPC water and its concentration was spectrophotometrically quantitated. Northern blotting was performed using a NorthernMax Kit (Ambion, Austin, Tex.). Eight µg of the RNA from each sample was loaded onto a 1% agarose-formaldehyde gel. After gel transfer and washing, the nylon membrane was hybridized with ntl probe (prepared as described above) following the manufacturer's instructions, and exposed to X-ray film for 72 hours. Subsequently the membrane was re-hybridized with the β-actin and ribozyme probes and was exposed to X-ray films for 12 hours. The results of the Northern hybridization are shown in FIG. 7.

FIG. 7 shows Northern blot analysis of fertilized zebrafish eggs which had been injected with ribozyme expression plasmid pT$_7$vaRz(ntl)$_{435}$, pT$_7$T$_7$ and T$_7$ RNA polymerase. In FIG. 7a, the Northern blot was hybridized with the ntl probe. Lane Rz contains RNA isolated from the injected embryos; Lane C contains RNA isolated from control uninfected embryos. FIG. 7b shows the same membrane as in FIG. 7b which was stripped and re-hybridized sequentially with ribozyme and actin probes FIG. 7a clearly shows a marked decrease in the ntl mRNA in the injected embryos as compared to the non-injected control embryos. Since ntl message appears and directs it's function principally at 5.2 hours into development [Schulte-Merker et al. (1992) supra], well before the occurrence of its phenotypic manifestation (i.e., tail formation), it was not possible to perform Northern hybridization analysis on only those 7% of the embryos which showed the complete no tail phenotype at approximately 24 hours into development. Therefore, since all injected embryos including those which eventually showed the normal phenotype (approximately 81%) and those which only showed partial no tail phenotype (approximately 12%) were included in the embryos from which the mRNA was isolated, a complete loss of the ntl mRNA was not expected. The approximate 30–50% decrease (normalized to equal loading of RNA of 8 µg/lane) in ntl mRNA at 5 hours (when ntl mRNA expression reaches its peak value) shown in FIG. 7a for injected embryos is consistent with the phenotypic observations of later stage injected zebrafish fry.

In order to determine whether and how early ribozyme was expressed in injected embryos, a probe specific for the $ntl_{435}$ ribozyme in zebrafish embryos was used to detect the presence of $Ribozyme_{435}$ at various times during their development. FIG. 7b shows large amounts of $ntl_{435}$ ribozyme in injected zebrafish embryos as early as 5.2 post-fertilization. High levels of ribozyme were detectable for at least 24 hours after fertilization, clearly indicating the presence of substantial amounts of ribozyme during the period of embryogenesis of the zebrafish.

These results demonstrate that the expression of a ribozyme within the developing zebrafish embryo, targeted against a messenger RNA encoding a specific gene product, can effectively "knockdown" the level of that message to a level which is sufficient to block the action of the targeted gene product.

The observation of an altered phenotype (i.e., no tail and/or partial no tail) following treatment with each individual ntl ribozyme together with the observation that ntl mRNA levels were reduced in embryos injected with each ribozyme vector demonstrates that each ribozyme was active in cleaving ntl mRNA and that such cleavage was associated with a phenotypic alteration that reflected the function of the ntl gene in tail formation.

The results also demonstrated that ribozymes targeted to different regions of the ntl mRNA had different effects on ablating mRNA expression levels and on phenotype expression. $Ribozyme_{435}$ which was targeted to a substrate cleavage site in a 14-nt loop resulted in the greatest reduction of ntl mRNA expression levels and generation of no tail mutants. $Ribozyme_{365}$ which was targeted to a substrate cleavage site in a 12-nt loop resulted in a lesser reduction in ntl mRNA expression levels than $Ribozyme_{365}$ and the generation of a partial no tail phenotype in the absence of a full no tail phenotype. $Ribozyme_{564}$ which was targeted to a cleave site in a 9-nt loop resulted in the lowest reduction of mRNA expression levels as compared to $Ribozyme_{435}$, and $Ribozyme_{365}$, as well as the lowest percentage of partial no tail phenotype in the absence of full no tail phenotype. These data suggest that ribozyme sequences targeted to a substrate cleavage site within a loop that is 14-nt long are more efficient at reducing substrate RNA expression than those ribozyme sequences with substrate cleavage sites in 12-nt loops, which in turn are more efficient than ribozymes which target cleavage sites in 9-nt loops.

EXAMPLE 3

Determination of the Function of the Notch 4 Gene by Knockdown of Expression of a Homologous Zebrafish Gene Using Ribozyme Sequences Expressed Under the Control of a Triple Promoter The int-3 oncogene is a frequent target in Mouse Mammary Tumor Virus (MMTFV)-induced mammary carcinomas and encodes the intracellular domain of the Notch 4 gene [Uyttendaele et al. (1996) Development 122:2251–2259]. To date, the function of the Notch 4 gene has not been definitively determined. In order to determine the function of the murine Notch 4 gene, two primers were designed based on the Notch 4 gene cDNA sequence (FIG. 9) (GenBank accession number U43691) using the "GENE-WORKS" program. A 468 bp Notch 4 cDNA fragment (52–519) will be amplified from zebrafish embryo total RNA by RT-PCR (as described above) using a pair of primers [the 5'-primer (21-nt) (SEQ ID NO:25) 5'-CAATCCCAGTTCTTT CATCTCC-3', and the 3'-primer (20-nt) (SEQ ID NO:26) 5'TGTCTCACCCAG AAATCCAGG-3']. For RT-PCR, all components except RNA template and primers will be supplied by a RT-PCR kit (Promega). The amplified fragment will then be cloned into the EcoRV sites of the pCR-3 vector (Promega) and the recovered 468 bp fragment will be sequenced, and used to replace the homologous 468 bp fragment in the mouse Notch 4 gene in order to generate a mouse-zebrafish chimeric gene sequence.

The secondary structure of this chimeric mRNA will be produced by using "RNADRAW" program described above, and the location of GUC and CUC sites on the mRNA encoded by the 468 bp zebrafish sequence, which are accessible to ribozyme digestion (i.e., GUC or CUC sites located on mRNA loops) will be determined as described above. Ribozymes targeted to these accessible GUC and CUC sites will be designed as described in Example 1 above.

For each of the designed ribozymes, a ribozyme gene will be synthesized as described in Example 1 by synthesizing two complementary single strands of the ribozyme gene sequence such that each oligonucleotide represents a strand of the sequence which should form a double stranded DNA when annealed to the complementary oligonucleotide single strand, and such that the resulting double-stranded DNA fragment contains a Sal I end at the 5'-end and a Pst I end at the 3'-end. The resulting double stranded DNA fragment is then inserted into the Sal I/Pst I sites of a $pCMVT_7VaT$ expression vector to generate the ribozyme expression vector $pCMVT_7vaRz7T$ such that the ribozyme gene in the ribozyme expression vector is under the transcriptional control of a triple $CMV-T_7$-vaRNA I promoter. The ribozyme expression vector $pCMVT_7vaRzT$ will have the following configuration from the 5'- to the 3'-end of the construct: $P_{CMV}$-$P_{T7}$-$P_{vaRNAI}$-Ribozyme gene-$T_{vaRNAI}$-$T_{T7}$-bGH poly(A), where P is a promoter, T is a transcription termination signal, and bGH poly(A) is the transcription termination signal for the CMV promoter.

The $pCMVT_7VaRzT$ ribozyme expression vector will be microinjected into zebrafish eggs (as described above) either alone, or in combination with coinjection of $pT_7T_7$ plasmid pre-bound with $T_7$ RNA polymerase. Microinjection of the $pCMVT_7VaRzT$ ribozyme expression vector alone is expected to result in high levels of ribozyme expression since the CMV promoter has been shown to result in high levels of expression in zebrafish of genes located downstream of the CMV promoter. This level of expression is expected to be further enhaced on coinjection of $pT_7T_7$ plasmid pre-bound with $T_7$ RNA polymerase since the $T_7$ promoter is recognized and transcribed by introduced $T_7$ RNA polymerase. The transgenic zebrafish embryos will be monitored both for resulting phenotypic changes as well as for the expression pattern of the tested gene as described in Examples 1 and 2, supra. Expression patterns will be determined by Northern blot analysis of total RNA prepared from different developmental stages of transgenic zebrafish embryos using the zebrafish 468 bp fragment as probe. The combination of observing both phenotypic changes between zebrafish embryos which are transgene for the ribozymes and control zebrafish embryos (either uninjected, or injected with the pCMVT$_7$VaT expression vector), as well expression patterns of the gene targeted by the ribozyme would acilitate determining a function for the targeted gene. In addition to phenotypic changes, biochemical, molecular biological and behavioral changes will be determined as described, supra.

The above-presented data shows that the expression of a ribozyme within the developing zebrafish embryo, targeted against a messenger RNA encoding a specific gene product, can effectively "knockdown" the level of that message to a level which is sufficient to block the function of the targeted gene product. This was demonstrated by targeting the message encoded by a zebrafish recessive dominant gene (ntl) with a known function contributing to the formation of the fish's tail and by showing complete blockage of tail formation in a significant percentage of fry hatched from embryos injected with plasmids encoding a ntl targeted ribozyme. These results demonstrate that a ribozyme "gene knockdown" strategy is useful for determining gene function and is more rapid than the traditional knockout methods used in the art.

What is claimed is:

1. A method for detecting changes in a zebrafish cell or in tissue obtained from a zebrafish cell, said changes caused by cleaving mRNA encoded by a gene of interest, comprising:
   a) providing:
      i) a zebrafish cell comprising a zebrafish genomic sequence having homology to a human genomic sequence, said zebrafish genomic sequence encoding an RNA sequence containing a substrate cleavage sequence; and
      ii) a ribozyme sequence capable of cleaving said RNA sequence;
   b) introducing said ribozyme sequence into said zebrafish cell to generate a manipulated cell, wherein said introducing is under conditions such that said RNA sequence is cleaved by said ribozyme sequence; and
   c) detecting one or more changes selected from morphological changes and behavioral changes in said manipulated cell relative to said zebrafish cell, or in tissue obtained from said manipulated cell relative to tissue obtained from said zebrafish cell, wherein said behavioral chantges are selected from light tropism and chemical tropism.

2. The method of claim 1, wherein said ribozyme is selected from the group consisting of group I intron ribozyme, ribonuclease P ribozyme, hammerhead ribozyme, hairpin ribozyme and hepatitis delta virus ribozyme.

3. The method of claim 1, wherein said ribozyme is a hammerhead ribozyme comprising a first substrate binding region, a second substrate binding region and a catalytic region, and wherein each of said first and second binding regions consists of 8 nucleotides.

4. The method of claim 1, wherein said substrate cleavage sequence is contained in a loop structure in said RNA sequence.

5. The method of claim 4, wherein said loop structure is selected from the group consisting of a 9-nucleotide loop, a 12-nucleotide loop and a 14-nucleotide loop.

6. The method of claim 1, wherein said ribozyme sequence is operably linked to a promoter sequence comprising an adenovirus type 2-associated RNA I gene promoter sequence.

7. The method of claim 6, wherein said promoter sequence further comprises a promoter sequence selected from the group consisting of tRNA, CMV, RSV, SV40, PEPCK, MT, SRα, P450 family, GAL7, $T_7$, $T_3$, SP6, K11 and heat shock protein promoter sequences.

8. The method of claim 1, wherein said promoter sequence comprises a CMV promoter sequence, a $T_7$ promoter sequence, and a vaRNA I promoter sequence.

9. The method of claim 1, wherein said zebrafish cell is an embryonic cell.

10. The method of claim 1, wherein the introduced ribozyme sequence is expressed in said manipulated cell, and wherein said expression is transient.

11. The method of claim 1, wherein the introduced ribozyme sequence is expressed in said manipulated cell, and wherein said expression is stable.

12. A method for detecting changes in a zebrafish oocyte or in tissue obtained from a zebrafish oocyte, said changes caused by cleaving mRNA encoded by a gene of interest, comprising:
  a) providing:
    i) a zebrafish oocyte comprising a zebrafish genomic sequence having homology to a human genomic sequence, said zebrafish genomic sequence encoding an RNA sequence; and
    ii) a ribozyme sequence capable of cleaving said RNA sequence;
  b) introducing said ribozyme sequence into said zebrafish oocyte to generate a manipulated oocyte, wherein said introducing is under conditions such that said RNA sequence is cleaved by said ribozyme sequence; and
  c) detecting one or more changes selected from morphological changes and behavioral changes in said manipulated oocyte relative to said zebrafish oocyte, or in tissue obtained from said manipulated oocyte relative to tissue obtained from said zebrafish oocyte, wherein said behavioral chances are selected from light tropism and chemical tropism.

13. The method of claim 12, wherein said ribozyme sequence is operably linked to a promoter sequence comprising an adenovirus type 2-associated RNA I gene promoter sequence.

14. The method of claim 13, wherein said promoter sequence further comprises a promoter sequence selected from the group consisting of tRNA, CMV, RSV, SV40, PEPCK, MT, SRα, P450 family, GAL7, $T_7$, $T_3$, SP6, K11 and heat shock protein promoter sequences.

15. The method of claim 12, wherein said promoter sequence comprises a CMV promoter sequence, a $T_7$ promoter sequence, and a vaRNA I promoter sequence.

16. The method of claim 12, wherein the introduced ribozyme sequence is expressed in said manipulated cell, and wherein said expression is transient.

17. The method of claim 12, further comprising step d) identifying at least one function for said zebrafish genomic sequence.

18. A method for detecting changes in a zebrafish cell or in tissue obtained from a zebrafish cell, said changes caused by cleaving mRNA encoded by a gene of interest, comprising:
  a) providing:
    i) a zebrafish cell, said zebrafish cell is transparent and comprises a zebrafish genomic sequence having homology to a human genomic sequence, said zebrafish genomic sequence encoding an RNA sequence; and
    ii) a ribozyme sequence capable of cleaving said RNA sequence;
  b) introducing said ribozyme sequence into said zebrafish cell to generate a manipulated cell, wherein said introducing is under conditions such that said RNA sequence is cleaved by said ribozyme sequence; and
  c) detecting one or more changes selected from morphological changes and behavioral changes in said manipulated cell relative to said zebrafish cell, or in tissue obtained from said manipulated cell relative to tissue obtained from said zebrafish cell, wherein said behavioral changes are selected from light tropism and chemical tropism.

19. The method of claim 18, wherein said ribozyme sequence is operably linked to a promoter sequence comprising an adenovirus type 2-associated RNA I gene promoter sequence.

20. The method of claim 19, wherein said promoter sequence further comprises a promoter sequence selected from the group consisting of tRNA, CMV, RSV, SV40, PEPCK, MT, SRα, P450 family, $GAL_7$, $T_7$, $T_3$, SP6, K11 and heat shock protein promoter sequences.

21. The method of claim 18, wherein said promoter sequence comprises a CMV promoter sequence, a $T_7$ promoter sequence, and a vaRNA I promoter sequence.

22. The method of claim 18, wherein the introduced ribozyme sequence is expressed in said manipulated cell, and wherein said expression is transient.

23. The method of claim 18, further comprising step d) identifying at least one function for said zebrafish genomic sequence.

24. The method of claim 1, further comprising step d) identifying at least one function for said zebrafish genomic sequence.

25. A method for detecting changes in zebrafish, said changes caused by cleaving mRNA encoded by a gene of interest, comprising:
  a) providing:
    i) a fertilized zebrafish oocyte, said fertilized oocyte comprising a zebrafish genomic sequence having homology to a human genomic sequence, said zebrafish genomic sequence encoding an RNA sequence containing a substrate cleavage sequence; and
    ii) a ribozyme sequence capable of cleaving said RNA sequence;
  b) introducing said ribozyme sequence into said fertilized oocyte to generate a manipulated fertilized oocyte, wherein said introducing is under conditions such that said RNA sequence is cleaved by said ribozyme sequence;
  c) permitting said manipulated fertilized oocyte to develop into a manipulated zebrafish offspring; and
  d) detecting one or more changes selected from morphological changes and behavioral changes in said manipulated zebrafish offspring relative to control zebrafish offspring, wherein said behavioral changes are selected from light tropism and chemical tropism.

26. A method for detecting changes in tissue obtained from a zebrafish cell, said changes caused by cleaving mRNA encoded by a gene of interest, comprising:
   a) providing:
      i) a zebrafish cell comprising a zebrafish genomic sequence having homology to a human genomic sequence, said zebrafish genomic sequence encoding an RNA sequence containing a substrate cleavage sequence; and
      ii) a ribozyme sequence capable of cleaving said RNA sequence;
   b) introducing said ribozyme sequence into said zebrafish cell to generate a manipulated cell, wherein said introducing is under conditions such that said RNA sequence is cleaved by said ribozyme sequence; and
   c) detecting one or more morphological changes in tissue obtained from said manipulated cell relative to tissue obtained from said zebrafish cell.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
        (A) LENGTH: 159 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:1:

```
GGCACTCTTC CGTGGTCTGG TGGATAAATT CGCAAGGGTA TCATGGCGGA CGACCGGGGT      60

TCGAACCCCG GATCCGGCCG TCCGCCGTGA TCCATGCGGT TACCGCCCGC GTGTCGAACC     120

CAGGTGTGCG ACGTCAGACA ACGGGGGAGC GCTCCTTTT                            159
```

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:2:

```
TAATACGACT CACTATAGGG CGA                                              23
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:3:

```
TTATTAACCC TCACTAAAGG GAAG                                             24
```

(2) INFORMATION FOR SEQ ID NO:4:

(i) SEQUENCE CHARACTERISTICS:
        (A) LENGTH: 23 base pairs

-continued

```
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:4:

ATTTAGGTGA CACTATAGAA TAC                                              23

(2) INFORMATION FOR SEQ ID NO:5:

(i) SEQUENCE CHARACTERISTICS:
        (A) LENGTH: 2238 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 84..1352

(xi) SEQUENCE DESCRIPTION: SEQ ID NO:5:

GAATTCCCGC TGTCAAAGCA ACAGTATCCA ACGGGAGTTA GTAGGATCGT CGGACTTATC       60

TCAAGCTTTA TTTGATCGGA AAT ATG TCT GCC TCA AGT CCC GAC CAG CGC          110
                         Met Ser Ala Ser Ser Pro Asp Gln Arg
                          1               5

CTG GAT CAT CTC CTT AGC GCC GTG GAG AGC GAA TTT CAG AAG GGC AGC        158
Leu Asp His Leu Leu Ser Ala Val Glu Ser Glu Phe Gln Lys Gly Ser
 10              15                  20                  25

GAG AAA GGG GAC GCG TCC GAG CGG GAT ATT AAA CTT TCG CTT GAA GAC        206
Glu Lys Gly Asp Ala Ser Glu Arg Asp Ile Lys Leu Ser Leu Glu Asp
                 30                  35                  40

GCG GAG TTG TGG ACC AAA TTT AAA GAG CTC ACC AAT GAA ATG ATT GTC        254
Ala Glu Leu Trp Thr Lys Phe Lys Glu Leu Thr Asn Glu Met Ile Val
             45                  50                  55

ACC AAG ACT GGG AGA CGA ATG TTT CCC GTG CTC AGA GCC AGT GTC ACC        302
Thr Lys Thr Gly Arg Arg Met Phe Pro Val Leu Arg Ala Ser Val Thr
         60                  65                  70

GGT CTC GAC CCT AAT GCA ATG TAC TCG GTC CTG CTG GAT TTT GTG GCG        350
Gly Leu Asp Pro Asn Ala Met Tyr Ser Val Leu Leu Asp Phe Val Ala
     75                  80                  85

GCC GAT AAT AAT CGG TGG AAA TAC GTG AAC GGT GAA TGG GTG CCC GGT        398
Ala Asp Asn Asn Arg Trp Lys Tyr Val Asn Gly Glu Trp Val Pro Gly
 90                  95                 100                 105

GGG AAA CCC GAA CCC CAA AGC CCG AGC TGC GTC TAC ATC CAC CCG GAC        446
Gly Lys Pro Glu Pro Gln Ser Pro Ser Cys Val Tyr Ile His Pro Asp
                110                 115                 120

TCA CCC AAC TTC GGC GCG CAC TGG ATG AAA GCA CCC GTA TCT TTC AGC        494
Ser Pro Asn Phe Gly Ala His Trp Met Lys Ala Pro Val Ser Phe Ser
            125                 130                 135

AAA GTC AAA CTC TCC AAT AAA CTC AAC GGA GGA GGA CAG ATT ATG TTA        542
Lys Val Lys Leu Ser Asn Lys Leu Asn Gly Gly Gly Gln Ile Met Leu
        140                 145                 150

AAC TCA TTG CAC AAA TAC GAA CCC AGG ATA CAC ATC GTG AAA GTC GGT        590
Asn Ser Leu His Lys Tyr Glu Pro Arg Ile His Ile Val Lys Val Gly
    155                 160                 165

GGG ATT CAG AAA ATG ATC AGC AGT CAG TCT TTT CCT GAG ACA CAG TTT        638
Gly Ile Gln Lys Met Ile Ser Ser Gln Ser Phe Pro Glu Thr Gln Phe
170                 175                 180                 185

ATT GCA GTC ACA GCA TAT CAG AAT GAA GAG ATT ACC GCT CTG AAA ATC        686
Ile Ala Val Thr Ala Tyr Gln Asn Glu Glu Ile Thr Ala Leu Lys Ile
```

|  |  |  |  |  |  |  |  |  |  |  |  |  |  |  |  |
|---|---|---|---|---|---|---|---|---|---|---|---|---|---|---|---|
|  |  |  |  | 190 |  |  |  |  | 195 |  |  |  |  | 200 |  |
| AAA | CAC | AAT | CCT | TTT | GCC | AAA | GCT | TTC | CTC | GAT | GCC | AAA | GAG | AGA | AGT | 734 |
| Lys | His | Asn | Pro | Phe | Ala | Lys | Ala | Phe | Leu | Asp | Ala | Lys | Glu | Arg | Ser |
|  |  |  | 205 |  |  |  |  | 210 |  |  |  |  | 215 |  |  |
| GAC | CAC | AAG | GAA | GTC | CCA | GAC | CAC | AGC | ACT | GAC | AAC | CAG | CAA | TCT | GGA | 782 |
| Asp | His | Lys | Glu | Val | Pro | Asp | His | Ser | Thr | Asp | Asn | Gln | Gln | Ser | Gly |
|  |  | 220 |  |  |  |  | 225 |  |  |  |  | 230 |  |  |  |
| TAT | TCA | CAA | CTC | GGT | GGC | TGG | TTC | CTG | CCC | AGT | AAC | GGC | CCC | ATG | GGC | 830 |
| Tyr | Ser | Gln | Leu | Gly | Gly | Trp | Phe | Leu | Pro | Ser | Asn | Gly | Pro | Met | Gly |
|  | 235 |  |  |  |  | 240 |  |  |  |  | 245 |  |  |  |  |
| CCC | AGC | AGC | AGC | CCT | CCT | CAG | TTC | ATT | GGG | GCC | CCT | GTT | CAC | TCC | TCG | 878 |
| Pro | Ser | Ser | Ser | Pro | Pro | Gln | Phe | Ile | Gly | Ala | Pro | Val | His | Ser | Ser |
| 250 |  |  |  |  | 255 |  |  |  |  | 260 |  |  |  |  | 265 |
| GGT | TCG | TAC | TGT | GAG | AGA | TAC | TCC | AGC | TTG | AGG | AAC | CAC | AGA | GCT | GCT | 926 |
| Gly | Ser | Tyr | Cys | Glu | Arg | Tyr | Ser | Ser | Leu | Arg | Asn | His | Arg | Ala | Ala |
|  |  |  |  | 270 |  |  |  |  | 275 |  |  |  |  | 280 |  |
| CCA | TAT | CCC | AGC | CAT | TAC | TCC | CAC | CGC | AGC | ACT | ACC | ACC | AAT | AAC | TAC | 974 |
| Pro | Tyr | Pro | Ser | His | Tyr | Ser | His | Arg | Ser | Thr | Thr | Thr | Asn | Asn | Tyr |
|  |  |  | 285 |  |  |  |  | 290 |  |  |  |  | 295 |  |  |
| ATG | GAC | AAC | TCT | TCC | GGA | AGT | CTT | GCG | TCT | CAT | GAC | AGC | TGG | TCA | GCC | 1022 |
| Met | Asp | Asn | Ser | Ser | Gly | Ser | Leu | Ala | Ser | His | Asp | Ser | Trp | Ser | Ala |
|  |  | 300 |  |  |  |  | 305 |  |  |  |  | 310 |  |  |  |
| CTG | CAG | ATC | CCC | AAC | TCC | AGC | GGG | ATG | GGA | ACC | CTG | GCC | CAC | ACC | ACA | 1070 |
| Leu | Gln | Ile | Pro | Asn | Ser | Ser | Gly | Met | Gly | Thr | Leu | Ala | His | Thr | Thr |
| 315 |  |  |  |  | 320 |  |  |  |  | 325 |  |  |  |  |  |
| AAC | ACT | ACC | TCC | AAC | ACC | AGT | CAG | TAC | CCA | AGT | CTG | TGG | TCA | GTT | GCA | 1118 |
| Asn | Thr | Thr | Ser | Asn | Thr | Ser | Gln | Tyr | Pro | Ser | Leu | Trp | Ser | Val | Ala |
| 330 |  |  |  |  | 335 |  |  |  |  | 340 |  |  |  |  | 345 |
| GGG | ACG | ACT | CTC | ACC | CCA | TCA | GGC | TCA | GCA | TCG | GGC | TCC | ATT | ACA | GGT | 1166 |
| Gly | Thr | Thr | Leu | Thr | Pro | Ser | Gly | Ser | Ala | Ser | Gly | Ser | Ile | Thr | Gly |
|  |  |  | 350 |  |  |  |  | 355 |  |  |  |  | 360 |  |  |
| GGC | CTG | ACA | TCT | CAG | TTC | CTA | CGC | GGT | TCT | TCG | ATG | TCC | TAC | TCG | GGT | 1214 |
| Gly | Leu | Thr | Ser | Gln | Phe | Leu | Arg | Gly | Ser | Ser | Met | Ser | Tyr | Ser | Gly |
|  |  | 365 |  |  |  |  | 370 |  |  |  |  | 375 |  |  |  |
| CTG | ACC | TCC | TCG | CTG | CCT | GTG | TCC | TCT | CCC | TCT | TCA | ATG | TAC | GAT | CCA | 1262 |
| Leu | Thr | Ser | Ser | Leu | Pro | Val | Ser | Ser | Pro | Ser | Ser | Met | Tyr | Asp | Pro |
|  | 380 |  |  |  |  | 385 |  |  |  |  | 390 |  |  |  |  |
| GGC | CTA | AGC | GAG | GTT | GGC | GTT | GGA | GAT | GCC | CAG | TTC | GAG | AGC | TCC | ATC | 1310 |
| Gly | Leu | Ser | Glu | Val | Gly | Val | Gly | Asp | Ala | Gln | Phe | Glu | Ser | Ser | Ile |
| 395 |  |  |  |  | 400 |  |  |  |  | 405 |  |  |  |  |  |
| GCC | CGG | CTC | ACA | GCA | TCA | TGG | GCG | CCT | GTG | GCT | CAG | AGC | TAC |  |  | 1352 |
| Ala | Arg | Leu | Thr | Ala | Ser | Trp | Ala | Pro | Val | Ala | Gln | Ser | Tyr |  |  |
| 410 |  |  |  |  | 415 |  |  |  |  | 420 |  |  |  |  |  |

TGAGATCGCT TCACATTTAA GGACTGATGC TGCAGTTATG GACTTGATCT TGGCTTCAGG    1412

AGGAAATCTA GAAGAGCTTC TTGATTTGAC AATCAGAAAA CGGGTTGATT TACTATAAAA    1472

GTCACATCTG TATCATACCG AGGCATACGT ATTTACAATC AAGATGAGAG ACAATCAATT    1532

AAAGGGTTAG TTCTTGCAAA AAAGAAAATT TTGACATCAT TTACTCACCT TTGTTTTAAA    1592

CATTGTTAAG TTTTTATTCT GTTAAACACA AAAGAAGATA TTTTGAAGAA TGTTCAAAAC    1652

TGGTAACCAT TGCATAGAAG CTGTTTTACT TATGGAAGTA AATGGTTACA GGTTATCAGC    1712

ATTTTTTTAA ATATATTTTT TAGTTCAACA GAAGAAAGAA ACTCTTTAAA GTTTGGAACA    1772

ACTTGAGGGT GAGTAAATTG AGTAAAAGTA CGTTTTTGGG TTAACTATCC CTTTAACTAT    1832

CAGATTTTAG CCATACATTT TGGGGCAATT ATAGTGTTTA TTCTTGATAA TATTATCTAA    1892

AAGATTAATA AAATCAAAAT TGTGCTGTTG ACTCACTAAA AGTGTATATG TGTGTAAATA    1952

AATAGAAATT AACGTCCGGT TTCATTGTAT CACAGAAGAA TGTAACAGTC TTACATGTGC    2012

-continued

```
TTTCTGTAGA ACGAGAGAAA GACAGACTTT GCTGTTTCGT TGAGAAAGT GAATACGCTT    2072

TGAAAAGTGA CCGTATAGTT TTGTCTGCTA TTCGTCCTAT AGAGAAACCA TTTGTACATA    2132

TCTATCTATT TGTATTTGTT GGGCTCTTTG AGTTTTATTT ATGTCATTTT AATAATAAAT    2192

TAAATTTCTT TTTTTTTTCT GTCAAAAAAA AGGAGTTCCG GAATTC                   2238
```

(2) INFORMATION FOR SEQ ID NO:6:

(i) SEQUENCE CHARACTERISTICS:
        (A) LENGTH: 423 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ser Ala Ser Ser Pro Asp Gln Arg Leu Asp His Leu Leu Ser Ala
  1               5                  10                  15

Val Glu Ser Glu Phe Gln Lys Gly Ser Glu Lys Gly Asp Ala Ser Glu
                 20                  25                  30

Arg Asp Ile Lys Leu Ser Leu Glu Asp Ala Glu Leu Trp Thr Lys Phe
             35                  40                  45

Lys Glu Leu Thr Asn Glu Met Ile Val Thr Lys Thr Gly Arg Arg Met
 50                  55                  60

Phe Pro Val Leu Arg Ala Ser Val Thr Gly Leu Asp Pro Asn Ala Met
 65                  70                  75                  80

Tyr Ser Val Leu Leu Asp Phe Val Ala Asp Asn Asn Arg Trp Lys
                 85                  90                  95

Tyr Val Asn Gly Glu Trp Val Pro Gly Gly Lys Pro Glu Pro Gln Ser
                100                 105                 110

Pro Ser Cys Val Tyr Ile His Pro Asp Ser Pro Asn Phe Gly Ala His
             115                 120                 125

Trp Met Lys Ala Pro Val Ser Phe Ser Lys Val Lys Leu Ser Asn Lys
130                 135                 140

Leu Asn Gly Gly Gly Gln Ile Met Leu Asn Ser Leu His Lys Tyr Glu
145                 150                 155                 160

Pro Arg Ile His Ile Val Lys Val Gly Gly Ile Gln Lys Met Ile Ser
                165                 170                 175

Ser Gln Ser Phe Pro Glu Thr Gln Phe Ile Ala Val Thr Ala Tyr Gln
             180                 185                 190

Asn Glu Glu Ile Thr Ala Leu Lys Ile Lys His Asn Pro Phe Ala Lys
         195                 200                 205

Ala Phe Leu Asp Ala Lys Glu Arg Ser Asp His Lys Glu Val Pro Asp
210                 215                 220

His Ser Thr Asp Asn Gln Gln Ser Gly Tyr Ser Gln Leu Gly Gly Trp
225                 230                 235                 240

Phe Leu Pro Ser Asn Gly Pro Met Gly Pro Ser Ser Pro Gln
                245                 250                 255

Phe Ile Gly Ala Pro Val His Ser Ser Gly Ser Tyr Cys Glu Arg Tyr
             260                 265                 270

Ser Ser Leu Arg Asn His Arg Ala Ala Pro Tyr Pro Ser His Tyr Ser
             275                 280                 285

His Arg Ser Thr Thr Thr Asn Asn Tyr Met Asp Asn Ser Ser Gly Ser
290                 295                 300

Leu Ala Ser His Asp Ser Trp Ser Ala Leu Gln Ile Pro Asn Ser Ser
```

```
305                 310                 315                 320
Gly Met Gly Thr Leu Ala His Thr Thr Asn Thr Thr Ser Asn Thr Ser
                325                 330                 335
Gln Tyr Pro Ser Leu Trp Ser Val Ala Gly Thr Thr Leu Thr Pro Ser
                340                 345                 350
Gly Ser Ala Ser Gly Ser Ile Thr Gly Gly Leu Thr Ser Gln Phe Leu
                355                 360                 365
Arg Gly Ser Ser Met Ser Tyr Ser Gly Leu Thr Ser Ser Leu Pro Val
                370                 375                 380
Ser Ser Pro Ser Ser Met Tyr Asp Pro Gly Leu Ser Glu Val Gly Val
385                 390                 395                 400
Gly Asp Ala Gln Phe Glu Ser Ser Ile Ala Arg Leu Thr Ala Ser Trp
                405                 410                 415
Ala Pro Val Ala Gln Ser Tyr
                420
```

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: mRNA (xi) SEQUENCE DESCRIPTION: SEQ ID NO:7:

AAUAAACUCA ACGGAGG                                            17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: mRNA (xi) SEQUENCE DESCRIPTION: SEQ ID NO:8:

CCCGGACUCA CCCAACU                                            17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: mRNA (xi) SEQUENCE DESCRIPTION: SEQ ID NO:9:

AUUGCAGUCA CAGCAUA                                            17

(2) INFORMATION FOR SEQ ID NO:10:

(i) SEQUENCE CHARACTERISTICS:
        (A) LENGTH: 3485 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "DNA"

(xi) SEQUENCE DESCRIPTION: SEQ ID NO:10:

```
CGTCGACTGC TGCAGTGCAG CGTGTGGACC CAACGACACG CGGGCGGTAA CCGACGTCAG       60
ACAACGGGGG AGCGCTCCTT TTGGCTTCCT TCCAGGCGCG GCGGCTGCTG CGCTAGCTTT      120
TTTGGCCACT GGCCGCGCGC GGCGTAAGCG GTTAGGCTGG AAAGCGAAAG CATTAAGTGG      180
CTCGCTCCCT GTAGCCGGAG GGTTATTTTC CAAGGGTTGA GTCGCAGGAC CCCCGGTTCG      240
AGTCTCGGGC CGGCCGGACT GCGGCGAACG GGGGTTTGCC TCCCCGTCAT GCAAGACCCC      300
GCTTGCAAAT TCCTCCGGAA ACAGGGACGA GCCCCTTTTT TGCTTTTCCC AGATGCAGGC      360
ATGCAAGCTT GGATCCGGAG AGCTCCCAAC GCGTTGGATG CATAGCTTGA GTATTCTATA      420
GTGTCACCTA AATAGCTTGG CGTAATCATG GTCATAGCTG TTTCCTGTGT GAAATTGTTA      480
TCCGCTCACA ATTCCACACA ACATACGAGC CGGAAGCATA AAGTGTAAAG CCTGGGGTGC      540
CTAATGAGTG AGCTAACTCA CATTATTTGC GTTGCGCTCA CTGCCCGCTT TCCAGTCGGG      600
AAACCTGTCG TGCCAGCTGC ATTAATGAAT CGGCCAACGC GCGGGAGAG GCGGTTTGCG       660
TATTGGGCGC TCTTCCGCTT CCTCGCTCAC TGACTCGCTG CGCTCGGTCG TTCGGCTGCG      720
GCGAGCGGTA TCAGCTCACT CAAAGGCGGT AATACGGTTA TCCACAGAAT CAGGGGATAA      780
CGCAGGAAAG AACATGTGAG CAAAAGGCCA GCAAAAGGCC AGGAACCGTA AAAAGGCCGC      840
GTTGCTGGCG TTTTTCGATA GGCTCCGCCC CCCTGACGAG CATCACAAAA ATCGACGCTC      900
AAGTCAGAGG TGGCGAAACC CGACAGGACT ATAAAGATAC CAGGCGGTTC CCCCTGGAAG      960
CTCCCTCGTG CGCTCTCCTG TTCCGACCCT GCCGCTTACC GGATACCTGT CCGCCTTTCT     1020
CCCTTCGGGA AGCGTGGCGC TTTCTCATAG CTCACGCTGT AGGTATCTCA GTTCGGTGTA     1080
GGTCGTTCGC TCCAAGCTGG GCTGTGTGCA CGAACCCCCC GTTCAGCCCG ACCGCTGCGC     1140
CTTATCCGGT AACTATCGTC TTGAGTCCAA CCCGGTAAGA CACGACTTAT CGCCACTGGC     1200
AGCAGCCACT GGTAACAGGA TTAGCAGAGC GAGGTATGTA GGCGGTGCTA CAGAGTTCTT     1260
GAAGTGGTGG CCTAACTACG GCTACACTAG AAGGACAGTA TTTGGTATCT GCGCTCTGCT     1320
GAAGCCAGTT ACCTTCGGAA AAAGAGTTGG TAGCTCTTGA TCCGGCAAAC AAACCACCGC     1380
TGGTAGCGGT GGTTTTTTTG TTTGCAAGCA GCAGATTACG CGCAGAAAAA AAGGATCTCA     1440
AGAAGATCCT TTGATCTTTT CTACGGGGTC TGACGCTCAG TGGAACGAAA ACTCACGTTA     1500
AGGGATTTTG GTCATGAGAT TATCAAAAAG GATCTTCACC TAGATCCTTT TAAATTAAAA     1560
ATGAAGTTTT TAATCAATCT AAAGTATATA TGAGTAAACT TGGTCTGACA GTTACCAATG     1620
CTTAATCAGT GAGGCACCTA TCTCAGCGAT CTGTCTATTT CGTTCATCCA TAGTTGCCTG     1680
ACTCCCCGTC GTGTAGATAA CTACGATACG GGAGGGCTTA CCATCTGGCC CCAGTGCTGC     1740
AATGATACCG CGAGACCCAC GCTCACCGGC TCCAGATTTA TCAGCAATAA ACCAGCCAGC     1800
CGGAAGGGCC GAGCGCAGAA GTGGTCCTGC AACTTTATCC GCCTCCATCC AGTCTATTAA     1860
TTGTTGCCGG GAAGCTAGAG TAAGTAGTTC GCCAGTTAAT AGTTTGCGCA ACGTTGTTGG     1920
CATTGCTACA GGCATCGTGG TGTCACGCTC GTCGTTTGGT ATGGCTTCAT TCAGCTCCGG     1980
TTCCCAACGA TCAAGGCGAG TTACATGATC CCCCATGTTG TGCAAAAAAG CGGTTAGCTC     2040
CTTCGGTCCT CCGATCGTTG TCAGAAGTAA GTTGGCCGCA GTGTTATCAC TCATGGTTAT     2100
GGCAGCACTG CATAATTCTC TTACTGTCAT GCCATCCGTA AGATGCTTTT CTGTGACTGG     2160
TGAGTACTCA ACCAAGTCAT TGTGAGAATA CCGCGCCCGG CGACCGAGTT GCTCTTGCCC     2220
GGCGTCAATA CGGGATAATA GTGTATGACA TAGCAGAACT TTAAAAGTGC TCATCATTGG     2280
```

| | |
|---|---|
| AAAACGTTCT TCGGGGCGAA AACTCTCAAG GATCTTACCG CTGTTGAGAT CCAGTTCGAT | 2340 |
| GTAACCCACT CGTGCACCCA ACTGATCTTC AGCATCTTTT ACTTTCACCA GCGTTTCTGG | 2400 |
| GTGAGCAAAA ACAGGAAGGC AAAATGCCGC AAAAAAGGGA ATAAGGGCGA CACGGAAATG | 2460 |
| TTGAATACTC ATACTCTTCC TTTTTCAATA TTATTGAAGC ATTTATCAGG GTTATTGTCT | 2520 |
| CATGAGCGGA TACATATTTG AATGTATTTA GAAAAATAAA CAAATAGGGG TTCCGCGCAC | 2580 |
| ATTTCCCCGA AAAGTGCCAC CTGTATGCGG TGTGAAATAC CGCACAGATG CTGAAGGAGA | 2640 |
| AAATACCGCA TCAGGCGAAA TTGTAAACGT TAATATTTTG TTAAAAATCG CGTTAAATAT | 2700 |
| TTGTTAAATC AGCTCATTTT TTAACCAATA GGCCGAAATC GGCAAAATCC CTTATAAATC | 2760 |
| AAAAGAATAG ACCGAGATAG GGTTGAGTGT TGTTCCAGTT TGGAACAAGA GTCCACTATT | 2820 |
| AAAGAACGTG GACTCCAACG TCAAAGGGCG AAAAACCGTC TATCAGGGCG ATGGCCCACT | 2880 |
| ACGTGAACCA TCACCCAAAT CAAGTTTTTT GCGGTCGAGG TGCCGTAAAG CTCTAAATCG | 2940 |
| GAACCCTAAA GGGAGCCCCC GATTTAGAGC TTGACGGGGA AAGCCGGCGA ACTGGGCGAG | 3000 |
| AAAGGAAGGG AAGAAAGCGA AAGGAGCGGG CGCTAGGGCG CTGGCAAGTG TAGCGGTCAC | 3060 |
| GCTGCGCTGA ACCACCACAC CCGCCGCGCT TAATTGCGCC GTACAGGGCG CGTCCATTCG | 3120 |
| CCATTCAGGC TGCGCAACTG TTGGGAAGGG CGATCGGTGC GGGCCTCTTC GCTATTACCC | 3180 |
| AGCTGGCCAA AGGGGGATGT GCTGCAAGGC GATTAAGTTG GGTAACGCCA GGGTTTTCCC | 3240 |
| AGTCACGACG TTGTAAAACGA CGGCCAGTGA ATTGTAATAC GACTCACTAT AGGGCGAATT | 3300 |
| GGGCCCGACG TCGCATGCTC CTCTAGACCG TGCAAAAGGA GAGCCTGTAA GGGCACTCTT | 3360 |
| CCGTGGTCTG GTGGATAAAT TCGCAAGGGT ATCATGGCGG ACGACCGGGG TTCGAACCCC | 3420 |
| GGATCCGGCC GTCCGCCGTG ATCCATGCGG TTACCGCCCG CGTGTCGAAC CCAGGTGTGC | 3480 |
| GACGT | 3485 |

(2) INFORMATION FOR SEQ ID NO:11:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:11:

| | |
|---|---|
| CGTCGACTGC TGCAGTGCAG CGTGTGGACC CAACGACACG CGGGCGGTAA CCGACGT | 57 |

(2) INFORMATION FOR SEQ ID NO:12:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:12:

| | |
|---|---|
| CGGTTACCGC CCGCGTGTCG TTGGGTCCAC ACGCTGCACT GCAGCAGTCG ACGACGT | 57 |

(2) INFORMATION FOR SEQ ID NO:13:

(i) SEQUENCE CHARACTERISTICS:
        (A) LENGTH: 47 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:13:

TCGACCTCCG TTCTGATGAG TCCGTGAGGA CGAAAGTTTA TTCTGCA                47

(2) INFORMATION FOR SEQ ID NO:14:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:14:

GAATAAACTT TCGTCCTCAC GGACTCATCA GAACGGAGG                         39

(2) INFORMATION FOR SEQ ID NO:15:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:15:

TCGACAGTTG GGTCTGATGA GTCCGTGAGG ACGAAAGTCC GGGCTGCA               48

(2) INFORMATION FOR SEQ ID NO:16:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:16:

GCCCGGACTT TCGTCCTCAC GGACTCATCA GACCCAACTG                        40

(2) INFORMATION FOR SEQ ID NO:17:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:17:

TCGACTATGC TGTCTGATGA GTCCGTGAGG ACGAAACTGC AATCTGCA               48

(2) INFORMATION FOR SEQ ID NO:18:

(i) SEQUENCE CHARACTERISTICS:

(A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:18:

GATTGCAGTT TCGTCCTCAC GGACTCATCA GACAGCATAG           40

(2) INFORMATION FOR SEQ ID NO:19:

(i) SEQUENCE CHARACTERISTICS:
        (A) LENGTH: 38 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "RNA"

(xi) SEQUENCE DESCRIPTION: SEQ ID NO:19:

CCUCCGUUCU GAUGAGUCCG UGAGGACGAA AGUUUAUU             38

(2) INFORMATION FOR SEQ ID NO:20:

(i) SEQUENCE CHARACTERISTICS:
        (A) LENGTH: 38 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "RNA"

(xi) SEQUENCE DESCRIPTION: SEQ ID NO:20:

GGGCCUGAAA GCAGGAGUGC CUGAGUAGUC UGGGUUGA             38

(2) INFORMATION FOR SEQ ID NO:21:

(i) SEQUENCE CHARACTERISTICS:
        (A) LENGTH: 38 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "RNA"

(xi) SEQUENCE DESCRIPTION: SEQ ID NO:21:

UAACGUCAAA GCAGGAGUGC CUGAGUAGUC UGUCGUAU             38

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:22:

CTGTCATGAG ACGCAAGACT T                              21

(2) INFORMATION FOR SEQ ID NO:23:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA"

(xi) SEQUENCE DESCRIPTION: SEQ ID NO:23:

GGATCATCTC CTTAGCGCCG T                                          21

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:24:

CTGTCATGAG ACGCAAGACT T                                          21

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:25:

CAATCCCAGT TCTTCATCTC C                                          21

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:26:

GTCTCACCCA GAAATCCAGG                                            20

(2) INFORMATION FOR SEQ ID NO:27:

(i) SEQUENCE CHARACTERISTICS:
        (A) LENGTH: 6677 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GGGAAAACAG GTGTGTTTCT GCCTTTTACT TCTAACTTGG AATACCTTAC CCAATCCCAG    60

TTCTTCATCT CCTCTGAGAA GTTATAGGGT TAAAAATATT GTCTTCTTAC ATCAGCAGAT   120

ATATGACAAG GGAAGAGATC CTTTGGTCAG CTCTAGTAAT CTGGCTTTGT CCCCCTTAGG   180

```
GAATAGACTT TGGCCTGAGG GAACAGCTCA GACTGAGGCG TGCAGCAGGC TCAGGAGGAA    240

GAAGGGCGGT AGAAGCAGAG GAAGTGGCCT TGCCTGGCCA CAAGGGCTCT GAGGGTCCCT    300

GCCTGAAGAG GGAGAGGAGA TCCGGGCCAG GGCAGGTGC TCTGGAATGC AGCCCCAGTT    360

GCTGCTGCTG CTGCTCTTGC CACTCAATTT CCCTGTCATC CTGACCAGAG AGCTTCTGTG    420

TGGAGGATCC CCAGAGCCCT GTGCCAACGG AGGCACCTGC CTGAGGCTAT CTCGGGGACA    480

AGGGATCTGC CAGTGTGCCC CTGGATTTCT GGGTGAGACT TGCCAGTTTC CTGACCCCTG    540

CAGGGATACC CAACTCTGCA AGAATGGTGG CAGCTGCCAA GCCCTGCTCC CCACACCCCC    600

AAGCTCCCGT AGTCCTACTT CTCCACTGAC CCCTCACTTC TCCTGCACCT GCCCCTCTGG    660

CTTCACCGGT GATCGATGCC AAACCCATCT GGAAGAGCTC TGTCCACCTT CTTTCTGTTC    720

CAACGGGGGT CACTGCTATG TTCAGGCCTC AGGCCGCCCA CAGTGCTCCT GCGAGCCTGG    780

GTGGACAGGT GAGCAATGCC AGCTCCGAGA CTTCTGCTCA GCCAACCCCT GTGCCAACGG    840

AGGCGTGTGC CTGGCCACAT ACCCCCAGAT CCAGTGCCGC TGTCCACCTG GGTTCGAGGG    900

TCACACCTGT GAACGCGACA TCAACGAGTG CTTCCTGGAG CCGGGACCCT GCCCTCAGGG    960

CACCTCCTGC CATAACACCT TGGGTTCCTA CCAGTGTCTC TGCCCTGTGG GGCAGGAAGG   1020

TCCCCAGTGC AAGCTCAGGA AGGGAGCCTG CCCTCCTGGA AGCTGTCTCA ATGGGGCAC   1080

CTGCCAGCTG GTCCCAGAGG GACACTCCAC CTTTCATCTC TGCCTCTGTC CCCCAGGTTT   1140

CACGGGGCTG GACTGTGAGA TGAACCCAGA TGACTGTGTC AGGCACCAGT GTCAGAACGG   1200

GGCCACCTGT CTGGATGGGC TGGATACCTA CACCTGCCCC TGCCCCAAGA CATGGAAGGG   1260

CTGGGACTGC TCTGAAGATA TAGATGAATG TGAAGCCCGG GGTCCCCCTC GCTGCAGGAA   1320

CGGTGGCACC TGCCAGAACA CAGCTGGCAG CTTTCACTGT GTGTGCGTGA GTGGCTGGGG   1380

AGGTGCAGGC TGTGAGGAGA ACCTGGATGA CTGTGCAGCT GCCACCTGTG CCCCGGGATC   1440

CACCTGCATC GACCGTGTGG GCTCTTTCTC CTGCCTCTGC CCACCTGGAC GCACAGGCCT   1500

CCTGTGCCAC CTGGAAGACA TGTGTTTGAG TCAGCCGTGC CACGTGAATG CCCAGTGCAG   1560

CACCAACCCT CTGACAGGCT CCACCCTCTG CATATGCCAG CCTGGCTACT CAGGATCCAC   1620

CTGTCACCAA GATCTGGATG AGTGCCAAAT GGCCCAGCAA GGACCCAGTC CTGCGAACA   1680

TGGGGGGTCC TGCATCAACA CCCCTGGCTC CTTCAACTGC CTCTGCCTGC CTGGTTACAC   1740

GGGCTCCCGC TGTGAAGCTG ACCACAATGA GTGCCTGTCA CAGCCCTGCC ACCCAGGCAG   1800

CACCTGCCTG GACCTGCTTG CAACCTTCCA CTGCCTCTGC CCACCAGGCT TGGAAGGGAG   1860

ACTCTGTGAG GTGGAGGTCA ATGAGTGCAC CTCTAATCCC TGCCTGAACC AAGCTGCCTG   1920

CCATGACCTG CTCAACGGCT TCCAGTGCCT CTGCCTTCCT GGATTCACCG GCGCCCGATG   1980

TGAGAAAGAC ATGGACAGAGT GTAGCAGCAC CCCCTGTGCC AATGGGGGGC GCTGCCGAGA   2040

CCAGCCTGGA GCCTTCTACT GCGAGTGTCT CCCAGGCTTT GAAGGGCCAC ACTGTGAGAA   2100

AGAAGTGGAC GAATGTCTGA GTGACCCCTG TCCCGTGGGA GCCAGCTGTC TTGATCTCCC   2160

CGGAGCATTC TTCTGTCTCT GCCGTCCTGG TTTCACAGGT CAACTTTGTG AGGTTCCCTT   2220

GTGCACCCCC AACATGTGCC AACCTGGACA GCAATGCCAA GGTCAGGAAC ACAGAGCCCC   2280

CTGCCTCTGC CCTGACGGAA GTCCTGGCTG TGTTCCTGCC GAGGACAACT GCCCCTGTCA   2340

CCATGGCCAT TGCCAGAGAT CCTTGTGTGT GTGTGATGAG GGCTGGACTG GACCAGAATG   2400

CGAGACAGAA CTGGGTGGCT GCATCTCCAC ACCCTGTGCC CATGGGGGGA CCTGCCACCC   2460

ACAGCCATCT GGCTACAACT GTACCTGCCC TGCAGGCTAC ATGGGGTTGA CCTGTAGTGA   2520
```

```
GGAGGTGACA GCTTGTCACT CAGGGCCCTG TCTCAATGGT GGCTCCTGCA GCATCCGTCC    2580

TGAGGGCTAT TCCTGCACCT GCCTTCCAAG TCACACAGGT CGCCACTGCC AGACTGCCGT    2640

GGACCACTGT GTGTCTGCCT CGTGCCTCAA TGGGGGTACC TGTGTGAACA AGCCTGGCAC    2700

TTTCTTCTGC CTCTGTGCCA CTGGCTTCCA GGGGCTGCAC TGTGAGGAGA AGACTAACCC    2760

CAGCTGTGCA GACAGCCCCT GCAGGAACAA GGCAACCTGC CAAGCACAC CTCGAGGGGC     2820

CCGCTGCCTC TGCAGCCCTG GCTATACAGG AAGCAGCTGC CAGACTCTGA TAGACTTGTG    2880

TGCCCGGAAG CCCTGTCCAC ACACTGCTCG ATGCCTCCAG AGTGGGCCCT CGTTCCAGTG    2940

CCTGTGCCTC CAGGGATGGA CAGGGGCTCT CTGTGACTTC CCACTGTCCT GCCAGAAGGC    3000

CGCGATGAGC CAAGGCATAG AGATCTCTGG CCTGTGCCAG AATGGAGGCC TCTGTATTGA    3060

CACGGGCTCC TCCTATTTCT GCCGCTGCCC TCCTGGATTC CAAGGCAAGT TATGCCAGGA    3120

TAATGTGAAC CCCTGCGAGC CCAATCCCTG CCATCACGGG TCTACCTGTG TGCCTCAGCC    3180

CAGTGGCTAT GTCTGCCAGT GTGCCCCAGG CTATGAGGGA CAGAACTGCT CAAAAGTACT    3240

TGACGCTTGT CAGTCCCAGC CCTGCCACAA CCACGGAACC TGTACCTCCA GGCCTGGAGG    3300

CTTCCACTGT GCCTGCCCTC CAGGCTTCGT GGGACTGCGC TGTGAGGGAG ATGTGGATGA    3360

GTGTCTGGAC CGGCCCTGTC ACCCCTCGGG CACTGCAGCT TGCCACTCTT TAGCCAACGC    3420

CTTCTACTGC CAGTGTCTGC CTGGGCACAC AGGCCAGCGG TGTGAGGTGG AGATGGACCT    3480

CTGTCAGAGC CAACCCTGCT CCAATGGAGG ATCCTGTGAG ATCACAACAG GGCCACCCCC    3540

TGGCTTCACC TGTCACTGCC CCAAGGGTTT TGAAGGCCCC ACCTGCAGCC ACAAAGCCCT    3600

TTCCTGCGGC ATCCATCACT GCCACAATGG AGGCCTATGT CTGCCCTCCC CTAAGCCAGG    3660

GTCACCACCG CTCTGTGCCT GCCTCAGTGG TTTTGGGGGC CCTGACTGTC TGACACCTCC    3720

AGCTCCACCG GGCTGCGGTC CCCCCTCACC CTGCCTGCAC AATGGTACCT GCACTGAGAC    3780

CCCTGGGTTG GGCAACCCGG GCTTTCAATG CACCTGCCCT CCTGACTCTC CAGGGCCCCG    3840

GTGTCAAAGG CCAGGGCAA GTGGGTGTGA GGGCCGAGGT GGTGATGGGA CCTGCGATGC     3900

TGGCTGCAGT GGCCCAGGAG GAGACTGGGA TGGAGGGGAC TGTTCCCTGG GGGTCCCAGA    3960

CCCCTGGAAG GGCTGTCCCC CGCATTCCCA GTGCTGGCTT CTGTTCCGGG ACGGACGGTG    4020

TCACCCGCAG TGTGACTCTG AGGAGTGTCT CTTTGATGGC TACGACTGTG AAATCCCTCC    4080

AACCTGCATC CCAGCCTATG ACCAGTACTG CCGAGATCAC TTCCACAACG GCACTGTGA    4140

GAAAGGCTGC AATAACGCTG AATGTGGCTG GGACGGGGA GACTGCAGAC CAGAAGGGGA     4200

AGACTCAGAG GGGAGGCCCT CCCTGGCCCT GCTGGTGGTG CTGAGGCCCC CAGCCCTGGA    4260

TCAGCAGCTG CTTGCCCTGG CACGAGTGCT GTCCCTGACT CTGAGGGTCG GTCTCTGGGT    4320

GAGGAAGGAC AGTGAAGGCA GGAACATGGT GTTCCCCTAT CCTGGGACCC GGGCCAAAGA    4380

GGAGCTGAGT GGAGCTAGGG ATTCCTCTTC ATGGGAAAGA CAAGCCCCTC CCACTCAGCC    4440

CCTGGGCAAG GAGACAGAGT CTCTTGGTGC AGGGTTTGTG GTAGTGATGG GAGTGGATCT    4500

GTCCCGCTGT GGTCCGGAAC ATCCTGCGTC CCGCTGCCCC TGGGACTCTG GACTCCTGCT    4560

GCGCTTCCTT GCAGCAATGG CAGCAGTGGG AGCTCTGGAG CCCCTGCTGC CTGGACCCTT    4620

GCTGGCGGCT CACCCTCAAG CAGGGACCAG GCCCCCTGCC AACCAGCTTC CCTGGCCCAT    4680

TCTATGTTCA CCAGTGGTTG GGGTGCTTCT CCTGGCCCTT GGGGCCCTTC TCGTCCTCCA    4740

GCTCATTCGG CGACGGCGAC GAGAACATGG GGCCCTGTGG CTGCCCCCTG GTTTCATTCG    4800

AAGGCCTCAG ACACAGCAGG CACCCCACCG GCGGAGGCCC CCACTGGGCG AGGACAACAT    4860

TGGTCTTAAG GCACTGAAGC CAGAGGCCGA AGTGGATGAG GATGGAGTGG CCATGTGCTC    4920
```

```
GGGCCCTGAA GAGGGAGAGG CTGAAGAAAC AGCCTCAGCC TCCAGGTGCC AGCTTTGGCC    4980

GCTCAACAGC GGCTGTGGAG AGCTCCCCCA GGCAGCCATG CTGACCCCTC CTCAGGAGTG    5040

TGAATCGGAG GTTCTGGATG TGGACACCTG TGGACCTGAT GGGGTGACAC CCCTGATGTC    5100

AGCCGTCTTC TGTGGGGAG TGCAGTCCAC GACTGGGGCT AGTCCACAGA GACTGGGGCT     5160

AGGAAATCTG GAACCCTGGG AACCACTGCT GGATAGAGGG GCCTGCCCCC AGGCTCACAC    5220

TGTGGGCACT GGAGAGACGC CTCTGCACCT AGCTGCCAGA TTCTCTCGGC CAACCGCTGC    5280

CCGCCGCCTC CTTGAGGCTG GAGCCAACCC CAACCAGCCA GACCGCGCTG GGCGCACCCC    5340

ACTTCACACT GCTGTGGCTG CCGACGCTCG GGAGGTTTGC CAGCTCCTAT TGGCCAGCAG    5400

ACAGACTACG GTGGACGCCC GCACAGAGGA CGGGACTACA CCTTTGATGC TGGCTGCCAG    5460

GCTGGCCGTG GAGGACCTGG TTGAAGAATT GATCGCAGCC CGAGCAGATG TAGGAGCCAG    5520

GGATAAAAGG GGAAAAACTG CACTGCACTG GGCCGCTGCT GTGAACAACG CCCGAGCCGC    5580

CCGCTCTCTC CTCCAGGCTG GAGCGGATAA AGATGCCCAG GACAGTAGGG AACAGACGCC    5640

GCTTTTCCTG GCAGCGCGCG AAGGAGCCGT GGAGGTGGCG CAGCTGTTGC TGGAGCTCGG    5700

GGCGGCCCGG GGACTGCGAG ACCAGGCCGG GCTGGCCCCA GGAGATGTGG CCCGCCAGCG    5760

CAGTCACTGG GACCTGCTAA CGCTGCTGGA AGGGGCTGGA CCGACTACGC AGGAGGCCCG    5820

TGCGCACGCA CGCACCACGC CGGGGGGCGG GTCCGCCCCG CGCTGCCGGA CGCTGTCTGC    5880

GGGAGCGCGC CCGCGCGGGG GCGGAGCCTG TCTGCAGGCT CGCACTTGGT CGGTGGACTT    5940

GGGAGCGCGC GGAGGGAAGG TGTATGCTCG CTGCCGGAGC CGATCTGGAA GCTGCGGAGG    6000

CCCCACCACG CGCGGCCGCA GGTTCTCCGC GGGCTCCCGT GGACGACGCG GGGCTAGGGC    6060

ATCACAGGAT GACTGGCCTC GCGACTGGGT GGCCCTGGAA GCCTGCGGCT CCGCCTGCAG    6120

TGCGCCGATC CCGCCTCCCA GCCTGACCCC GTCCCCAGAA CGTGGATCCC CTCAAGTTGC    6180

CTGGGGTCTT CCAGTTCACC AAGAGATTCC CTTAAACTCG GTTGTAAGAA ATCTGAACTA    6240

GGCAGCTGCG TGGAAGGAAG GAAGCGACAC GTACGAGTCT GGAAGACTCC GGACTTTTAA    6300

GGCCAAAATA ACCGTTAAGC TCACTTGTCT CCCCCATAGA GTATGCACAG CAATGGGAAG    6360

AGGGTTTAGG ATGTCCGGTT GAGATAGACC GTGATTTTCC TGGAAAATAG GGCAGCTTCA    6420

AGAGGACAAA GTTGATTTCG AGAATCCCTA AACTCTGGAA CCAAGAACTG TGGGCGAATT    6480

GGGTGTAAAA TGTTTCTTGT GTATGGTTTC CCAAAAGGAG CCTCTGCTAT CTACTGCCCA    6540

CAAGTAGCTG GCAACTATTT ATTAAGCACC TACGATGTGC CGGGTGTTGT GTAGATGAAC    6600

AGTAAGTAAC CAGTGGCCCA TCCAGCTGAT GACTCCTTGC CCTCTCTCTG CCTCCCCACA    6660

AGGACACTGG TGCAGGG                                                   6677
```